United States Patent
Wang et al.

(10) Patent No.: US 10,144,915 B2
(45) Date of Patent: Dec. 4, 2018

(54) REPROGRAMMING FIBROBLASTS INTO CARDIOMYOCYTES

(71) Applicant: The J. David Gladstone Institutes, a testamentary trust established under the Will of J. David Gladstone, San Francisco, CA (US)

(72) Inventors: Haixia Wang, San Francisco, CA (US); Sheng Ding, Orinda, CA (US)

(73) Assignee: THE J. DAVID GLADSTONE INSTITUTES, A TESTAMENTARY TRUST ESTABLISHED UNDER THE WILL OF J. DAVID GLADSTONE, San Francisco, CA (US)

( * ) Notice: Subject to any disclaimer, the term of this patent is extended or adjusted under 35 U.S.C. 154(b) by 0 days.

(21) Appl. No.: 15/030,911

(22) PCT Filed: Oct. 23, 2014

(86) PCT No.: PCT/US2014/061970
§ 371 (c)(1),
(2) Date: Apr. 21, 2016

(87) PCT Pub. No.: WO2015/061568
PCT Pub. Date: Apr. 30, 2015

(65) Prior Publication Data
US 2016/0251624 A1    Sep. 1, 2016

Related U.S. Application Data

(60) Provisional application No. 61/894,815, filed on Oct. 23, 2013.

(51) Int. Cl.
| | | |
|---|---|---|
| *A61K 48/00* | (2006.01) | |
| *C07H 21/02* | (2006.01) | |
| *C07H 21/04* | (2006.01) | |
| *C12N 5/077* | (2010.01) | |
| *A61K 35/34* | (2015.01) | |

(52) U.S. Cl.
CPC .......... *C12N 5/0657* (2013.01); *A61K 35/34* (2013.01); *C12N 2501/01* (2013.01); *C12N 2501/15* (2013.01); *C12N 2501/415* (2013.01); *C12N 2501/603* (2013.01); *C12N 2501/70* (2013.01); *C12N 2501/72* (2013.01); *C12N 2501/727* (2013.01); *C12N 2501/999* (2013.01); *C12N 2506/02* (2013.01); *C12N 2506/13* (2013.01); *C12N 2506/1307* (2013.01); *C12N 2510/00* (2013.01)

(58) Field of Classification Search
CPC ..................... C12N 15/113; C12N 2310/11
See application file for complete search history.

(56) References Cited

U.S. PATENT DOCUMENTS

| | | |
|---|---|---|
| 9,517,250 B2 | 12/2016 | Srivastava et al. |
| 9,517,251 B2 | 12/2016 | Srivastava et al. |
| 2005/0043260 A1 | 2/2005 | Schneider et al. |
| 2009/0275032 A1 | 11/2009 | Eilertsen et al. |
| 2010/0105100 A1 | 4/2010 | Sakurada et al. |
| 2010/0267141 A1 | 10/2010 | Shi et al. |
| 2012/0208278 A1 | 8/2012 | Yanik et al. |
| 2012/0214234 A1 | 8/2012 | Takamatsu et al. |
| 2013/0029866 A1 | 1/2013 | Sun et al. |
| 2013/0216503 A1 | 8/2013 | Srivastava et al. |
| 2013/0273536 A1 | 10/2013 | Shi et al. |
| 2014/0235526 A1 | 8/2014 | Srivastava et al. |
| 2014/0301991 A1 | 10/2014 | Srivastava et al. |

FOREIGN PATENT DOCUMENTS

| | | |
|---|---|---|
| WO | WO-2006/109170 A2 | 10/2006 |
| WO | WO-2009/117439 | 9/2009 |
| WO | WO-2010/007031 A2 | 1/2010 |
| WO | WO-2010/108126 A1 | 9/2010 |
| WO | WO-2011/139688 A2 | 11/2011 |
| WO | WO-2011/159726 A2 | 12/2011 |
| WO | WO-2013023982 A1 | 2/2013 |
| WO | WO-2013130769 A1 | 9/2013 |
| WO | WO-2015061568 A1 | 4/2015 |

OTHER PUBLICATIONS

Chambers et al. (Nat. Biotechnol, 2009, 27(3), 275-280).*
"International Application Serial No. PCT/US2014/061970, International Search Report dated Jan. 22, 2015", 2 pgs.
"International Application Serial No. PCT/US2014/061970, Written Opinion dated Jan. 22, 2015", 10 pgs.
Cao, Nan et al.; "Highly efficient induction and long-term maintenance of multipotent cardiovascular progenitors from human pluripotent stem cells under defined conditions," Cell Research, vol. 23, No. 9. Jul. 30, 2013.
Efe, Jem A., et al. "Conversion of mouse fibroblasts into cardiomyocytes using a direct reprogramming strategy", Nature Cell Biology, vol. 13, No. 3. Mar. 1, 2011.
Extended European Search Report and Opinion dated Jun. 12, 2017 in connection with Application No. EP14856409.9 filed Oct. 23, 2014. 5 pages.
Heallen, T. et al. Hippo pathway inhibits Wnt signaling to restrain cardiomyocyte proliferation and heart size. Science 332, 458-461 , doi:1 0.1 126/science.1 199010, 2011.
Ieda et al., "Direct reprogramming of fibroblasts into functional cardiomyocytes by defined factors", Cell, 2010, 142 (3):375-386.
International Search Report dated Oct. 5, 2017 for International Application No. PCT/US2017/025132.
Kwon C. et al. "Canonical Wnt signaling is a positive regulator of mammalian cardiac progenitors," Proc. Natl. Acad. Sci. 104 26 10894-10899 Jun. 26, 2007.

(Continued)

*Primary Examiner* — Amy Hudson Bowman
(74) *Attorney, Agent, or Firm* — Cooley LLP

(57) ABSTRACT

Compositions and methods are described herein for chemically inducing cells that express a single pluripotency transcription factor to change their differentiation state and become cardiac cells, cardiac progenitor cells, cardiomyocytes, or a combination thereof.

32 Claims, 15 Drawing Sheets

Specification includes a Sequence Listing.

(56) References Cited

OTHER PUBLICATIONS

Lian X. et al. "Directed cardiomyocyte differentiation from human pluripotent stem cells by modulating Wnt/β-catenin signaling under fully defined conditions," Nat Protoc 81: 162-175 2013.
Mohamed. et al. Abstract 1 1415: Enhancing Direct Cardiac Reprogramming Efficiency Using Small Molecules. Circulation. 2015. 2 pages.
Supplementary European Search Report dated Jun. 29, 2017 in connection with Application No. EP14856409.9 filed Oct. 23, 2014. 5 pages.
Qian et al. "In vivo reprogramming of murine cardiac fibroblasts into induced cardiomyocytes", Nature (May, 2012), 485(7400):593-598.
Wada, et al. Induction of Human Cardiomyocyte-like Cells From Fibroblasts by Defined Factors. PNAS. Jul. 30, 2013, vol. 1 10, pp. 12667-12672. 6 pages.
Written Opinion dated Oct. 5, 2017 for International Application No. PCT/US2017/025132.

\* cited by examiner

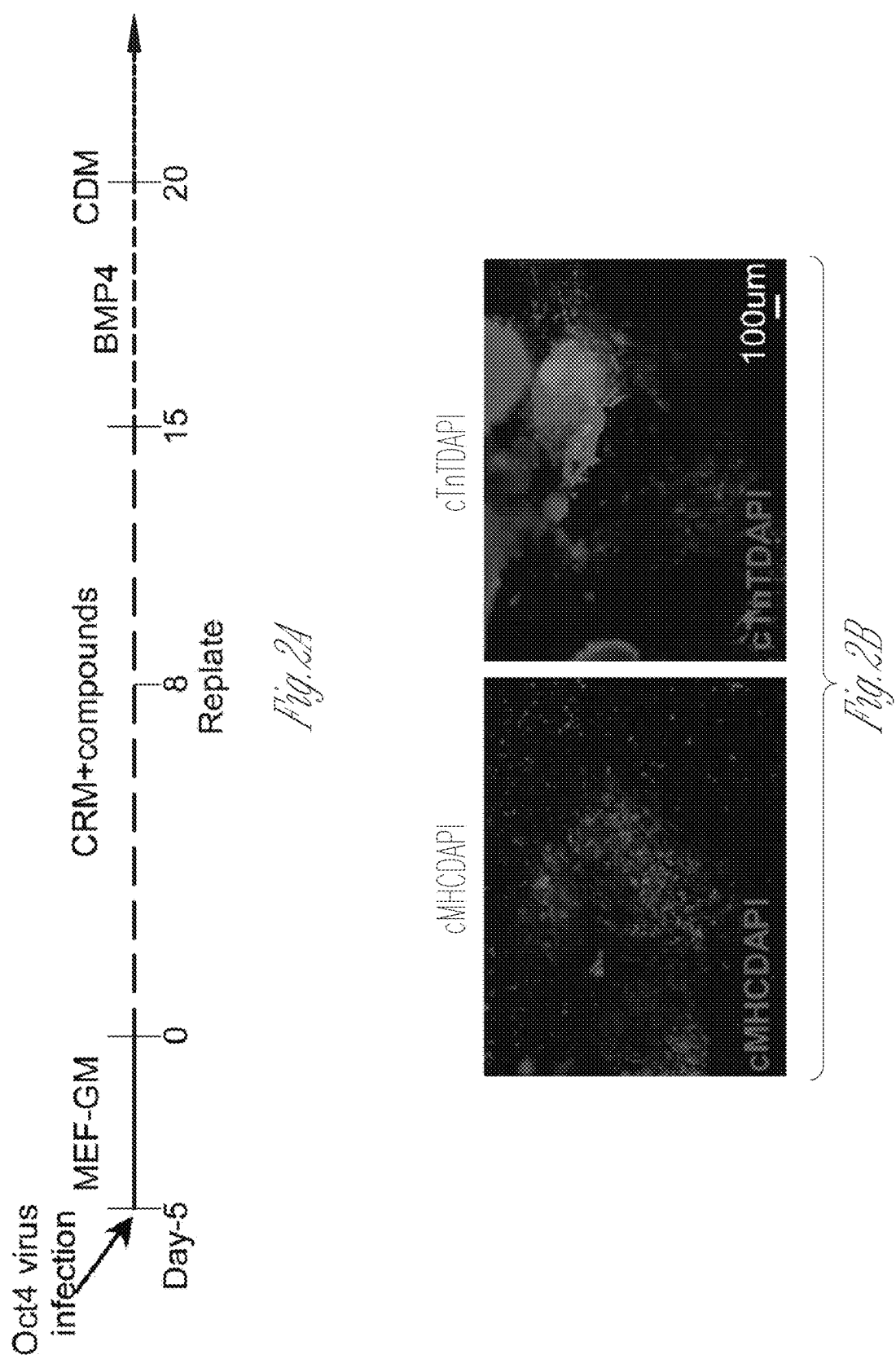

| | dv/dtMax | OSPc (mV) | MDPc (mV) | AP amp | APD50 (ms) | APD90 (ms) | Freq (Hz) |
|---|---|---|---|---|---|---|---|
| V-like (n=16) | 91.4±18.1* | 23.5±1.1** | −75.2±1.3** | 98.7±1.3* | 102.5±10.2* | 149.5±11.4 | 1.3±0.1 |
| A-like (n=3) | 25.7±5.7 | 13.9±1.1 | −67.8±1.0 | 81.8±2.0 | 62.3±6.2 | 173.3±18.0 | 1.0±0.1 |

SEQUENCE LISTING

```
<160> NUMBER OF SEQ ID NOS: 22

<210> SEQ ID NO 1
<211> LENGTH: 360
<212> TYPE: PRT
<213> ORGANISM: Homo sapiens

<400> SEQUENCE: 1

Met Ala Gly His Leu Ala Ser Asp Phe Ala Phe Ser Pro Pro Pro Gly
  1               5                  10                  15

Gly Gly Gly Asp Gly Pro Gly Gly Pro Glu Pro Gly Trp Val Asp Pro
                 20                  25                  30

Arg Thr Trp Leu Ser Phe Gln Gly Pro Pro Gly Gly Pro Gly Ile Gly
             35                  40                  45

Pro Gly Val Gly Pro Gly Ser Glu Val Trp Gly Ile Pro Pro Cys Pro
         50                  55                  60

Pro Pro Tyr Glu Phe Cys Gly Gly Met Ala Tyr Cys Gly Pro Gln Val
 65                  70                  75                  80

Gly Val Gly Leu Val Pro Gln Gly Gly Leu Glu Thr Ser Gln Pro Glu
                 85                  90                  95

Gly Glu Ala Gly Val Gly Val Glu Ser Asn Ser Asp Gly Ala Ser Pro
                100                 105                 110

Glu Pro Cys Thr Val Thr Pro Gly Ala Val Lys Leu Glu Lys Glu Lys
            115                 120                 125

Leu Glu Gln Asn Pro Glu Glu Ser Gln Asp Ile Lys Ala Leu Gln Lys
130                 135                 140

Glu Leu Glu Gln Phe Ala Lys Leu Leu Lys Gln Lys Arg Ile Thr Leu
145                 150                 155                 160

Gly Tyr Thr Gln Ala Asp Val Gly Leu Thr Leu Gly Val Leu Phe Gly
                165                 170                 175

Lys Val Phe Ser Gln Thr Thr Ile Cys Arg Phe Glu Ala Leu Gln Leu
            180                 185                 190

Ser Phe Lys Asn Met Cys Lys Leu Arg Pro Leu Leu Gln Lys Trp Val
        195                 200                 205

Glu Glu Ala Asp Asn Asn Glu Asn Leu Gln Glu Ile Cys Lys Ala Glu
210                 215                 220

Thr Leu Val Gln Ala Arg Lys Arg Lys Arg Thr Ser Ile Glu Asn Arg
225                 230                 235                 240

Val Arg Gly Asn Leu Glu Asn Leu Phe Leu Gln Cys Pro Lys Pro Thr
                245                 250                 255

Leu Gln Gln Ile Ser His Ile Ala Gln Gln Leu Gly Leu Glu Lys Asp
            260                 265                 270

Val Val Arg Val Trp Phe Cys Asn Arg Arg Gln Lys Gly Lys Arg Ser
        275                 280                 285

Ser Ser Asp Tyr Ala Gln Arg Glu Asp Phe Glu Ala Ala Gly Ser Pro
    290                 295                 300

Phe Ser Gly Gly Pro Val Ser Phe Pro Leu Ala Pro Gly Pro His Phe
305                 310                 315                 320

Gly Thr Pro Gly Tyr Gly Ser Pro His Phe Thr Ala Leu Tyr Ser Ser
```

325                 330                 335
Val Pro Phe Pro Glu Gly Glu Ala Phe Pro Pro Val Ser Val Thr Thr
                340                 345                 350

Leu Gly Ser Pro Met His Ser Asn
            355                 360

<210> SEQ ID NO 2
<211> LENGTH: 1411
<212> TYPE: DNA
<213> ORGANISM: Homo sapiens

<400> SEQUENCE: 2

| | | | | | |---:|
| ccttcgcaag | ccctcatttc | accaggcccc | cggcttgggg | cgccttcctt | ccccatggcg | 60 |
| ggacacctgg | cttcggattt | cgccttctcg | cccccctccag | gtggtggagg | tgatgggcca | 120 |
| ggggggccgg | agccgggctg | ggttgatcct | cggacctggc | taagcttcca | aggccctcct | 180 |
| ggagggccag | gaatcgggcc | ggggggttggg | ccaggctctg | aggtgtgggg | gattccccca | 240 |
| tgccccccgc | cgtatgagtt | ctgtgggggg | atggcgtact | gtgggcccca | ggttggagtg | 300 |
| gggctagtgc | cccaaggcgg | cttggagacc | tctcagcctg | agggcgaagc | aggagtcggg | 360 |
| gtggagagca | actccgatgg | ggcctccccg | gagccctgca | ccgtcacccc | tggtgccgtg | 420 |
| aagctggaga | ggagaagct | ggagcaaaac | ccggaggagt | cccaggacat | caaagctctg | 480 |
| cagaaagaac | tcgagcaatt | tgccaagctc | ctgaagcaga | gaggatcac | cctgggatat | 540 |
| acacaggccg | atgtggggct | caccctgggg | gttctatttg | gaaggtatt | cagccaaacg | 600 |
| accatctgcc | gctttgaggc | tctgcagctt | agcttcaaga | acatgtgtaa | gctgcggccc | 660 |
| ttgctgcaga | agtgggtgga | ggaagctgac | aacaatgaaa | atcttcagga | gatatgcaaa | 720 |
| gcagaaaccc | tcgtgcaggc | ccgaaagaga | aagcgaacca | gtatcgagaa | ccgagtgaga | 780 |
| ggcaacctgg | agaatttgtt | cctgcagtgc | ccgaaaccca | cactgcagca | gatcagccac | 840 |
| atcgcccagc | agcttgggct | cgagaaggat | gtggtccgag | tgtggttctg | taaccggcgc | 900 |
| cagaagggca | agcgatcaag | cagcgactat | gcacaacgag | aggattttga | ggctgctggg | 960 |
| tctcctttct | caggggggacc | agtgtccttt | cctctggccc | cagggcccca | ttttggtacc | 1020 |
| ccaggctatg | ggagccctca | cttcactgca | ctgtactcct | cggtcccttt | ccctgagggg | 1080 |
| gaagcctttc | ccctgtctc | cgtcaccact | ctgggctctc | ccatgcattc | aaactgaggt | 1140 |
| gcctgccctt | ctaggaatgg | gggacagggg | gaggggagga | gctagggaaa | gaaaacctgg | 1200 |
| agtttgtgcc | agggttttg | ggattaagtt | cttcattcac | taaggaagga | attgggaaca | 1260 |
| caaagggtgg | gggcagggga | gtttggggca | actggttgga | gggaaggtga | agttcaatga | 1320 |
| tgctcttgat | tttaatccca | catcatgtat | cactttttc | ttaaataaag | aagcctggga | 1380 |
| cacagtagat | agacacactt | aaaaaaaaaa | a | | | 1411 |

<210> SEQ ID NO 3
<211> LENGTH: 352
<212> TYPE: PRT
<213> ORGANISM: Mus musculus

<400> SEQUENCE: 3

Met Ala Gly His Leu Ala Ser Asp Phe Ala Phe Ser Pro Pro Pro Gly
  1               5                  10                  15

Gly Gly Asp Gly Ser Ala Gly Leu Glu Pro Gly Trp Val Asp Pro Arg
             20                  25                  30

Thr Trp Leu Ser Phe Gln Gly Pro Pro Gly Gly Pro Gly Ile Gly Pro 35                  40                  45
Gly Ser Glu Val Leu Gly Ile Ser Pro Cys Pro Ala Tyr Glu Phe
 50                  55                  60

Cys Gly Gly Met Ala Tyr Cys Gly Pro Gln Val Gly Leu Gly Leu Val
 65                      70                  75                  80

Pro Gln Val Gly Val Glu Thr Leu Gln Pro Glu Gly Gln Ala Gly Ala
                     85                  90                  95

Arg Val Glu Ser Asn Ser Glu Gly Thr Ser Ser Glu Pro Cys Ala Asp
                100                 105                 110

Arg Pro Asn Ala Val Lys Leu Glu Lys Val Glu Pro Thr Pro Glu Glu
                115                 120                 125

Ser Gln Asp Met Lys Ala Leu Gln Lys Glu Leu Glu Gln Phe Ala Lys
                130                 135                 140

Leu Leu Lys Gln Lys Arg Ile Thr Leu Gly Tyr Thr Gln Ala Asp Val
145                 150                 155                 160

Gly Leu Thr Leu Gly Val Leu Phe Gly Lys Val Phe Ser Gln Thr Thr
                    165                 170                 175

Ile Cys Arg Phe Glu Ala Leu Gln Leu Ser Leu Lys Asn Met Cys Lys
                180                 185                 190

Leu Arg Pro Leu Leu Glu Lys Trp Val Glu Glu Ala Asp Asn Asn Glu
                195                 200                 205

Asn Leu Gln Glu Ile Cys Lys Ser Glu Thr Leu Val Gln Ala Arg Lys
210                 215                 220

Arg Lys Arg Thr Ser Ile Glu Asn Arg Val Arg Trp Ser Leu Glu Thr
225                 230                 235                 240

Met Phe Leu Lys Cys Pro Lys Pro Ser Leu Gln Gln Ile Thr His Ile
                    245                 250                 255

Ala Asn Gln Leu Gly Leu Glu Lys Asp Val Val Arg Val Trp Phe Cys
                260                 265                 270

Asn Arg Arg Gln Lys Gly Lys Arg Ser Ser Ile Glu Tyr Ser Gln Arg
                275                 280                 285

Glu Glu Tyr Glu Ala Thr Gly Thr Pro Phe Pro Gly Gly Ala Val Ser
                290                 295                 300

Phe Pro Leu Pro Pro Gly Pro His Phe Gly Thr Pro Gly Tyr Gly Ser
305                 310                 315                 320

Pro His Phe Thr Thr Leu Tyr Ser Val Pro Phe Pro Glu Gly Glu Ala
                    325                 330                 335

Phe Pro Ser Val Pro Val Thr Ala Leu Gly Ser Pro Met His Ser Asn
                340                 345                 350

<210> SEQ ID NO 4
<211> LENGTH: 1353
<212> TYPE: DNA
<213> ORGANISM: Mus musculus

<400> SEQUENCE: 4
gaggtgaaac cgtccctagg tgagccgtct ttccaccagg cccccggctc ggggtgccca      60
ccttccccat ggctggacac ctggcttcag acttcgcctt ctcaccccca ccaggtgggg     120
gtgatgggtc agcagggctg gagccgggct ggtggatcc tcgaacctgg ctaagcttcc      180
aagggcctcc aggtgggcct ggaatcggac caggctcaga ggtattgggg atctccccat     240
gtccgcccgc atacgagttc tgcgaggga tggcatactg tggacctcag gttggactgg      300
gcctagtccc ccaagttggc gtggagactt tgcagcctga gggccaggca ggagcacgag     360

-continued

```
tggaaagcaa ctcagaggga acctcctctg agccctgtgc cgaccgcccc aatgccgtga        420
agttggagaa ggtggaacca actcccgagg agtcccagga catgaaagcc ctgcagaagg        480
agctagaaca gtttgccaag ctgctgaagc agaagaggat caccttgggg tacacccagg        540
ccgacgtggg gctcaccctg ggcgttctct ttggaaaggt gttcagccag accaccatct        600
gtcgcttcga ggccttgcag ctcagcctta agaacatgtg taagctgcgg cccctgctgg        660
agaagtgggt ggaggaagcc gacaacaatg agaaccttca ggagatatgc aaatcggaga        720
ccctggtgca ggcccggaag agaaagcgaa ctagcattga gaaccgtgtg aggtggagtc        780
tggagaccat gttctgaag tgcccgaagc cctccctaca gcagatcact cacatcgcca         840
atcagcttgg gctagagaag gatgtggttc gagtatggtt ctgtaaccgg cgccagaagg        900
gcaaaagatc aagtattgag tattcccaac gagaagagta tgaggctaca gggacacctt        960
tcccaggggg ggctgtatcc tttcctctgc ccccaggtcc ccactttggc accccaggct       1020
atggaagccc ccacttcacc acactctact cagtcccttt tcctgagggc gaggcctttc       1080
cctctgttcc cgtcactgct ctgggctctc ccatgcattc aaactgaggc accagccctc       1140
cctggggatg ctgtgagcca aggcaaggga ggtagacaag agaacctgga gctttggggt       1200
taaattcttt tactgaggag ggattaaaag cacaacaggg gtgggggtg ggatggggaa        1260 agaagctcag tgatgctgtt gatcaggagc ctggcctgtc tgtcactcat cattttgttc       1320
ttaaataaag actgggacac acagtagata gct                                    1353
```

<210> SEQ ID NO 5
<211> LENGTH: 21
<212> TYPE: DNA
<213> ORGANISM: Artificial Sequence
<220> FEATURE:
<223> OTHER INFORMATION: A synthetic oligonucleotide primer

<400> SEQUENCE: 5
cctggaagac accccaatct c         21

<210> SEQ ID NO 6
<211> LENGTH: 21
<212> TYPE: DNA
<213> ORGANISM: Artificial Sequence
<220> FEATURE:
<223> OTHER INFORMATION: A synthetic oligonucleotide primer

<400> SEQUENCE: 6
aggtagtgtc ccgtcccatc t         21

<210> SEQ ID NO 7
<211> LENGTH: 21
<212> TYPE: DNA
<213> ORGANISM: Artificial Sequence
<220> FEATURE:
<223> OTHER INFORMATION: A synthetic oligonucleotide primer

<400> SEQUENCE: 7
ggtctcaatg cctatggcta c         21

<210> SEQ ID NO 8
<211> LENGTH: 21
<212> TYPE: DNA
<213> ORGANISM: Artificial Sequence
<220> FEATURE:
<223> OTHER INFORMATION: A synthetic oligonucleotide primer

<400> SEQUENCE: 8
gccaaagttc acgaagttgc t                                              21

<210> SEQ ID NO 9
<211> LENGTH: 25
<212> TYPE: DNA
<213> ORGANISM: Artificial Sequence
<220> FEATURE:
<223> OTHER INFORMATION: A synthetic oligonucleotide primer

<400> SEQUENCE: 9
agatacccac aacacaccac gcgcc                                          25

<210> SEQ ID NO 10
<211> LENGTH: 29
<212> TYPE: DNA
<213> ORGANISM: Artificial Sequence
<220> FEATURE:
<223> OTHER INFORMATION: A synthetic oligonucleotide primer

<400> SEQUENCE: 10
cattatcctt cagagagtcg catgcgctt                                      29

<210> SEQ ID NO 11
<211> LENGTH: 22
<212> TYPE: DNA
<213> ORGANISM: Artificial Sequence
<220> FEATURE:
<223> OTHER INFORMATION: A synthetic oligonucleotide primer

<400> SEQUENCE: 11
acatcatgtt ttaccgcctg ag                                             22

<210> SEQ ID NO 12
<211> LENGTH: 23
<212> TYPE: DNA
<213> ORGANISM: Artificial Sequence
<220> FEATURE:
<223> OTHER INFORMATION: A synthetic oligonucleotide primer

<400> SEQUENCE: 12
tttgtggtta ttgaactctg gct                                            23

<210> SEQ ID NO 13
<211> LENGTH: 20
<212> TYPE: DNA
<213> ORGANISM: Artificial Sequence
<220> FEATURE:
<223> OTHER INFORMATION: A synthetic oligonucleotide primer

<400> SEQUENCE: 13
gatgcccaga tggctgactt                                                20

<210> SEQ ID NO 14
<211> LENGTH: 20
<212> TYPE: DNA
<213> ORGANISM: Artificial Sequence
<220> FEATURE:
<223> OTHER INFORMATION: A synthetic oligonucleotide primer

<400> SEQUENCE: 14
ggtcagcatg gccatgtcct                                                20

<210> SEQ ID NO 15
<211> LENGTH: 21
<212> TYPE: DNA

```
<213> ORGANISM: Artificial Sequence
<220> FEATURE:
<223> OTHER INFORMATION: A synthetic oligonucleotide primer

<400> SEQUENCE: 15
gcggaagagt gggaagagac a                                              21

<210> SEQ ID NO 16
<211> LENGTH: 20
<212> TYPE: DNA
<213> ORGANISM: Artificial Sequence
<220> FEATURE:
<223> OTHER INFORMATION: A synthetic oligonucleotide primer

<400> SEQUENCE: 16
ccacagctcc ttggccttct                                                20

<210> SEQ ID NO 17
<211> LENGTH: 21
<212> TYPE: DNA
<213> ORGANISM: Artificial Sequence
<220> FEATURE:
<223> OTHER INFORMATION: A synthetic oligonucleotide primer

<400> SEQUENCE: 17
tcttcctggt ccccacagtt t                                              21

<210> SEQ ID NO 18
<211> LENGTH: 23
<212> TYPE: DNA
<213> ORGANISM: Artificial Sequence
<220> FEATURE:
<223> OTHER INFORMATION: A synthetic oligonucleotide primer

<400> SEQUENCE: 18
gcaagaatag ttctcgggat gaa                                            23

<210> SEQ ID NO 19
<211> LENGTH: 21
<212> TYPE: DNA
<213> ORGANISM: Artificial Sequence
<220> FEATURE:
<223> OTHER INFORMATION: A synthetic oligonucleotide primer

<400> SEQUENCE: 19
ccctcgacag actgaccta a                                               21

<210> SEQ ID NO 20
<211> LENGTH: 22
<212> TYPE: DNA
<213> ORGANISM: Artificial Sequence
<220> FEATURE:
<223> OTHER INFORMATION: A synthetic oligonucleotide primer

<400> SEQUENCE: 20
tcggggctaa tctcactttc at                                             22

<210> SEQ ID NO 21
<211> LENGTH: 21
<212> TYPE: DNA
<213> ORGANISM: Artificial Sequence
<220> FEATURE:
<223> OTHER INFORMATION: A synthetic oligonucleotide primer

<400> SEQUENCE: 21
gtggcaaagt ggagattgtt g                                              21
```

```
<210> SEQ ID NO 22
<211> LENGTH: 20
<212> TYPE: DNA
<213> ORGANISM: Artificial Sequence
<220> FEATURE:
<223> OTHER INFORMATION: A synthetic oligonucleotide primer

<400> SEQUENCE: 22
ctcctggaag atggtgatgg                                              20
```

REPROGRAMMING FIBROBLASTS INTO CARDIOMYOCYTES

CROSS REFERENCE TO RELATED APPLICATIONS

This application is a U.S. National Stage Application filed under 35 U.S.C. § 371 from International Application No. PCT/US2014/061970, filed on Oct. 23, 2014, and published as WO 2015/061568 on Apr. 30, 2015, which application claims the benefit of priority to U.S. Provisional Patent Application Ser. No. 61/894,815 entitled "Reprogramming Cardiomyocytes with One Transcription Factor," filed Oct. 23, 2013, the complete disclosure of which applications are incorporated herein by reference in their entireties.

BACKGROUND

The differentiated cell state is often considered stable and resistant to changes in lineage identity. However, differentiated somatic cell types from humans and other organisms have been reprogrammed to the pluripotent state ("pluripotent reprogramming") by forced expression of a set of transcription factors (Takahashi, K. et al. Induction of pluripotent stem cells from adult human fibroblasts by defined factors, Cell 131, 861-872 (2007)), somatic cell nuclear transfer (Campbell et al., Sheep cloned by nuclear transfer from a cultured cell line, Nature 380: 64-66 (1996); Gurdon et al., Sexually mature individuals of Xenopus laevis from the transplantation of single somatic nuclei, Nature 182, 64-65 (1958)) or cell fusion (Cowan et al., Nuclear reprogramming of somatic cells after fusion with human embryonic stem cells, Science (New York, N.7309, 1369-1373 (2005); Tada et al., Nuclear reprogramming of somatic cells by in vitro hybridization with ES cells, Curr Biol 11, 1553-1558 (2001)). Additionally, a few studies have demonstrated that through ectopic expression of selected genes or by cell fusion, an adult cell type can be directly converted to another adult cell type (Cobaleda et al., Conversion of mature B cells into T cells by dedifferentiation to uncommitted progenitors, Nature 449, 473-477 (2007); Davis et al., Expression of a single transfected cDNA converts fibroblasts to myoblasts, Cell 51, 987-1000 (1987); Feng, et al. PU. 1 and C/EBPalpha/beta convert fibroblasts into macrophage-like cells, Proc. Nat. Acad. Sci. USA 105, 6057-6062 (2008); Ieda et al. Direct reprogramming of fibroblasts into functional cardiomyocytes by defined factors, Cell 142, 375-386 (2010); Zhou et al., In vivo reprogramming of adult pancreatic exocrine cells to beta-cells, Nature 455, 627-632 (2008); and Zhou, Q. & Melton, D. A. Extreme makeover: converting one cell into another, Cell Stem Cell 3: 382-388 (2008)). This process is termed trans-differentiation or lineage reprogramming.

However, major challenges remain due to the low efficiency and slow reprogramming process. A more significant challenge is how to accomplish cell reprogramming with minimal genetic changes in the reprogrammed cells, because such genetic changes give rise to concerns about introduced mutations at the insertion site of expression cassettes encoding pluripotency factors and other genetic material.

SUMMARY

The methods described herein can accomplish reprogramming of differentiated, non-cardiac cells to generate cardiac progenitor cells and cardiomyocytes by use of just one transcription factor, and without necessarily traversing the pluripotent state. Compositions are described herein to facilitate such reprogramming One aspect of the invention is a composition that includes one or more of the following agents: a WNT agonist, a GSK3 inhibitor, a TGF-beta inhibitor (e.g., an ALK4/5/7 inhibitor), an epigenetic modifier (e.g., an LSD1/KDM1 inhibitor), an adenylyl cyclase agonist, an agent that induces Oct polypeptide expression, and any combination thereof. For example, the composition can include one or more of the following agents: CHIR99021 (a GSK3 inhibitor), SB431542 (an ALK4/5/7 inhibitor), parnate (an LSD1/KDM1 inhibitor), forskolin (an adenylyl cyclase activator), and an agent that induces Oct expression, or a combination thereof.

Another aspect of the invention is a method of treating a subject that includes administering any of the compositions described herein.

Another aspect of the invention is a method of generating a cardiac progenitor cell, a cardiomyocyte, a cardiac cell, or a combination thereof that includes contacting one or more selected cells with any of the composition described herein, to thereby generate a cardiac progenitor cell, a cardiomyocyte, and/or a cardiac cell. The one or more selected cells can be non-cardiac cells such as partially or completely differentiated non-cardiac cells from a subject. The one or more selected cells can include Oct RNA molecules, Oct polypeptides, or a combination thereof. For example, the one or more selected cells can express Oct RNA molecules, Oct polypeptides, or a combination thereof.

Another aspect of the invention includes administering to a subject a cardiac progenitor cell, a cardiomyocyte, or a cardiac cell generated by the methods described herein. For example, the method can include administering to a subject a population of cardiac progenitor cells, cardiomyocytes, cardiac cells, or a combination thereof that have been generated by the methods described herein. The administered cells can, for example, transiently express an Oct polypeptide during the conversion method, but when administered, the cells no longer express Oct, and may no longer contain exogenous DNA encoding Oct.

DESCRIPTION OF THE FIGURES

FIG. 1A is a schematic timeline of direct cardiac reprogramming with Oct4, K1f4 and Sox2, showing when small molecules and BMP4 were added. As shown, cells were infected with a lentiviral vector that can express Oct4, K1f4, and Sox2, and incubated in mouse embryonic fibroblast growth medium (MEF-GM) for three days. Different media were then used as described in Example 1, including various small molecules that were added to the cardiac reprogramming media (CRM) from day 0 to day 6. FIG. 1B illustrates the relative expression of cTnT in cells on day 21 using whole-well imaging of cells grown in 12-well plates in the presence of various small molecules. S: SB431542; C: CHIR99021; P: parnate; and F: forskolin. Scale bar is 3 mm. As illustrated, the number of cells expressing cTNT is greater when the combination of SCP or SCPF is used. FIG. 1C graphically illustrates the number of spontaneously beating clusters generated with the different combinations of small molecules.

FIG. 2A-2H illustrates that a small molecule cocktail containing SB431542, CHIR99021, parnate; and Forskolin (SCPF) enabled cardiac reprogramming with a single transcription factor, Oct4. FIG. 2A is a schematic diagram of a timeline of direct cardiac reprogramming with a single factor, Oct4, and the small molecule cocktail containing SCPF. FIG. 2B shows beating clusters generated from mouse embryonic fibroblasts after 25 days (day 25) of treatment with SCPF and immunostaining for cTnT and cardiac MHC. FIG. 2C graphically illustrates expression of cardiac markers (Myh6, Tnnt2, Ryr2, Gata4, Nkx2-5) as detected by qPCR analysis in the induced cardiomyocytes (iCM) generated from mouse tail tip fibroblasts at day 30, compared to neonatal heart cells (abbreviated "H") and untreated mouse tail tip fibroblasts (TTFs). mRNA from untreated TTFs and neonatal heart were used as controls. FIG. 2D shows small clumps or single cells digested from beating clusters generated from mouse tail tip fibroblasts where the small clumps or single cells were immunostained for α-actinin or cTnT. Note that a clear striated pattern is visible (see area in box). FIG. 2E illustrates expression of various cardiac cell markers in small clumps or single cells digested from TTF-treated beating clusters generated by the compositions and methods described herein. Scale bar is 100 µm. As illustrated core transcription factors and peptides for cardiac development and function including Gata4, MEF2C, and Nkx2-5, as well as ANP, were highly expressed in the induced cardiomyocytes. Moreover, Connexin-43 (Cx43), which is a specific gap junction protein in cardiomyocytes, was also detected along the periphery of the induced cardiomyocytes, indicating the development of gap junction proteins involved in cell contact communication. The rightmost column of images shows the combined expression of the factors shown in the left three columns. FIG. 2F shows that few twitching/contracting cells that expressed cTnT, cMHC and α-Actinin were also observed in the control wells treated only with small molecules (e.g., the SCPF composition) without Oct4 transduction. FIG. 2G shows that cells treated only with small molecules (e.g., the SCPF composition) without Oct4 transduction lacked expression of core cardiac transcription factors such as Nkx2-5 and Gata4. FIG. 2H graphically illustrates the relative expression levels of several genes in cells treated only with small molecules (e.g., SCPF) without Oct4 transduction.

FIG. 3A shows phase-contrast (top) and fluorescence (bottom) microscopic images taken over illustrating induced cardiac colony formation in Oct4-GFP reporter mouse embryonic fibroblasts at the indicated days during the reprogramming process. An area of spontaneous contraction is encircled. No fluorescence (GFP expression) was detected on days 7, 12, 15, 18, 20, 23, and 25. FIG. 3B shows images of cells that were fixed and immunostained with an anti-cTnT antibody. Nuclei were stained with DAPI. FIG. 3C graphically illustrates Nanog expression over the time period of treatment, as measured by quantitative-PCR analysis. FIG. 3D graphically illustrates Rex1 expression over the time period of treatment, as measured by quantitative-PCR analysis. FIG. 3E graphically illustrates expression of cardiac lineage markers Gata4, Tnnt2, Myh6, and Ryr2 over the time period of treatment, as measured by quantitative-PCR analysis. Data shown are mean±standard deviation.

FIG. 4A shows representative spontaneous action potentials exhibiting the characteristics of ventricular or atrial-like morphology. The waveform of a single action potential is shown on the right (top) using an expanded time scale. Dotted lines indicate a resting potential of 0 mV. FIG. 4B shows a table of action potential parameters measured for the induced cardiomyocytes, including maximum upstroke velocity (dV/dt max), overshoot potential (OSP), minimum diastolic potential (MOP) AP amplitude and the APDs at 90 and 50% repolarization, and the beating frequency. *p<0.005, **p<0.001. FIG. 4C shows images of reprogrammed cells immunostained with cTnT, MLC2v, and MLC2a antibodies after treatment for 45 days (day 45) with the SCPF composition and expression of Oct4. FIG. 4D illustrates characteristic calcium transients ($[Ca^{2+}]_i$) recorded from the spontaneously contracting cardiomyocytes generated by the SCPF composition and expression of Oct4. FIG. 4E-4H illustrate the beating rates and calcium transients of reprogrammed cells after treatment with 1 µM Isoproterenol (Iso) (FIGS. 4E and 4G) or 25 µM carbachol (Cch) (FIGS. 4F and 4H). FIG. 4E shows the beating rates of control and Isoproterenol-treated cells. FIG. 4F illustrates calcium transients of reprogrammed cells before and after treatment with 1 µM Isoproterenol (Iso), where Isoproterenol was present during the period identified by the shaded box. FIG. 4G shows the beating rates of control and carbachol-treated cells. FIG. 4H illustrates calcium transients of reprogrammed cells before and after treatment with 25 µM carbachol (Cch), where carbachol was present during the period identified by the shaded box.

DETAILED DESCRIPTION

Figure 1A:
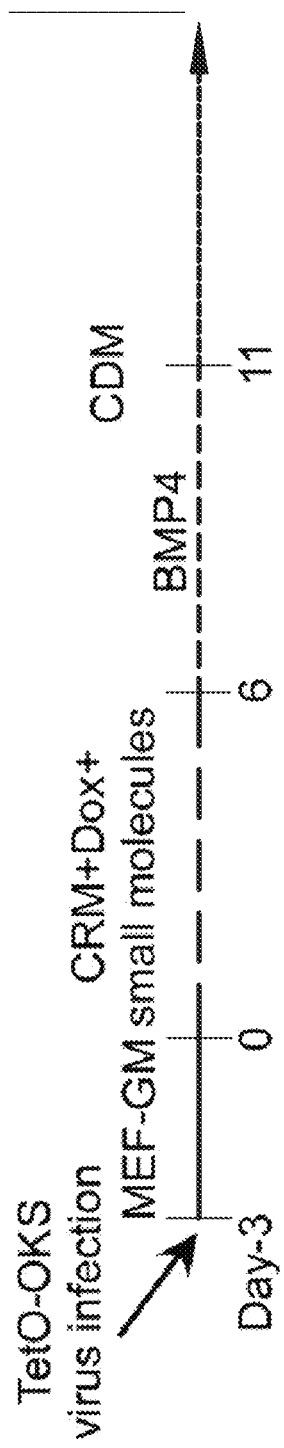
FIG. 1A-1C illustrates identification of small molecules that promoted direct conversion of mouse embryonic fibroblasts (MEFs) into beating cardiomyocytes with Oct4, K1f4 and Sox2 (OKS).

As described herein, differentiated mammalian cells can be reprogrammed to cross lineage boundaries and to directly convert to another cell type, for example a cardiac progenitor cell type or a cardiomyocyte, by inducing expression of one transcription factor (an Oct polypeptide) with exposure of cells to a chemical composition containing a variety of small molecules. Not only is such small molecule-enabled cardiac reprogramming more efficient with a drastically reduced number of genes (i.e., use of one transcription factor rather than four), the spontaneously beating cardiomyocytes generated by the compositions and methods described herein also exhibited a ventricular phenotype.

Reprogramming

Although more than one recombinantly introduced transcription factor can be used if desired, differentiated mammalian cells can be converted into the cardiac cell lineage by induction of expression of just one transcription factor (an Oct polypeptide) along with a composition of chemical agents. No exogenous K1f4, Myc, and/or Sox2 nucleic acids need be introduced to reprogram cells. Expression of an endogenous Oct gene can be induced in a selected cell or population of cells, while the cell(s) are contacted with the composition. Alternatively, a starting cell or population of cells can be engineered to include a heterologous expression cassette encoding an Oct polypeptide, where the nucleic acid segment encoding the Oct polypeptide is operably linked to regulatory elements such as a transcription promoter and a termination sequence. Reprogramming of a selected cell can be effected by expression of the Oct polypeptide while contacting the cell with the composition.

The composition of chemical compounds can be administered to a subject, or differentiated (e.g., non-cardiac) cells (e.g., from the subject) can be incubated with such a composition to convert those cells to a cardiac progenitor cell type or a cardiomyocyte. The reprogrammed cells can then be administered to the subject.

A reprogramming composition can be employed that contains one or more of the following chemical agents: a WNT agonist, a GSK3 inhibitor, a TGF-beta inhibitor, epigenetic modifier, adenylyl cyclase agonists, an agent that induces Oct polypeptide expression, and any combination thereof. The composition can contain more than one of such agents, or more than two of such agents, or more than three of such agents, or more than four of such agents, or five of such agents, or six of such agents.

WNT Agonists

Approximately twenty WNT proteins have been identified in mammals. Examples of WNT proteins include WNT1, WNT2, WNT2b/13, WNT3, WNT3a, WNT4, WNT5a, WNT5b, WNT6, WNT7a, WNT7b, WNT7c, WNT8, WNT8a, WNT8b, WNT8c, WNT10a, WNT10b, WNT11, WNT14, WNT15, or WNT16. WNT proteins are secreted, cysteine-rich proteins.

The WNT signaling pathway includes a series of events that occur when a WNT protein binds to a cell-surface receptor of a Frizzled receptor family member. Such events result in the activation of Dishevelled family proteins which inhibit a complex of proteins that includes axin, GSK-3, and the protein APC to degrade intracellular beta-catenin. The resulting enriched nuclear beta-catenin enhances transcription by TCF/LEF family transcription factors. A WNT agonist can therefore include an agent that activates TCF/LEF-mediated transcription in a cell. WNT agonists can be selected from true WNT agonists that bind and activate a Frizzled receptor family member including any and all of the WNT family proteins, an inhibitor of intracellular beta-catenin degradation, activators of TCF/LEF, and inhibitors of GSK-3.

Activation of the WNT pathway leads to inhibition of GSK3, subsequent nuclear accumulation of β-catenin and the expression of target genes. WNT agonists can include WNT-3a, GSK-inhibitors (such as any of those described herein), WNT 5, WNT-6a, Norrin, and any other WNT family protein.

For example, a WNT agonist can include a secreted glycoprotein including WNT-1/Int-1, WNT-2/Irp (InM-related Protein), WNT-2b/13, WNT-3/Int-4, WNT-3a (R&D Systems), WNT-4, WNT-5a, WNT-5b, WNT-6 (Kirikoshi et al., *Biochem Biophys Res Commun* 283: 798-805 (2001)), WNT-7a (R&D systems), WNT-7b, WNT-8a/8d, WNT-8b, WNT-9a/14, WNT-9b/14b/15, WNT-10a, WNT-10b/12, WNT-11, and Wnt-16. An overview of human WNT proteins is provided in "THE WNT FAMILY OF SECRETED PROTEINS", R&D Systems Catalog, 2004. Other WNT agonists include the R-spondin family of secreted proteins, which is implicated in the activation and regulation of WNT signaling pathway and which is comprised of 4 members (R-spondin 1 (NU206, Nuvelo, San Carlos, Calif.), R-spondin 2 (R&D systems), R-spondin 3, and R-spondin-4), and Norrin (also called Norrie Disease Protein or NDP) (R&D systems), which is a secreted regulatory protein that functions like a WNT protein in that it binds with high affinity to the Frizzled-4 receptor and induces activation of the WNT signaling pathway (Kestutis Planutis et al., *BMC Cell Biol* 8-12 (2007)). In some embodiments, one or more WNT agonists can include an R-spondin mimic, for example an agonist of Lgr5 such as an anti-Lgr5 antibody. A small-molecule agonist of the WNT signaling pathway, an aminopyrimidine derivative, was recently identified and is also expressly included as a WNT agonist (Lin et al. *Angew Chem Int Ed Engl* 44, 1987-90 (2005)).

In some embodiments, the WNT agonist is a GSK-inhibitor.

One or more WNT agonists can be included in a composition for treatment of a subject. Alternatively, one or more WNT agonists can be included in a cell medium useful for reprogramming a differentiated cell into a cardiac cell type, such as a cardiomyocyte.

The WNT agonists can be employed in the compositions and methods described herein in a variety of amounts and/or concentrations. For example, the WNT agonists can be employed at a concentration of about 0.01 micromolar to about 10 millimolar in a solution, or about 0.1 micromolar to about 100 micromolar in a solution, or about 1 micromolar to about 20 micromolar in a solution, or about 5 micromolar to about 15 micromolar in a solution. In a dry formulation, the WNT agonists can be present in amounts of about 0.01 mg to about 1000 mg, or about 1 mg to about 100 mg, or about 1 mg to about 10 mg.

GSK3 Inhibitors

Glycogen synthase kinase 3 (GSK3) is a serine/threonine protein kinase that catalyzes the addition of phosphate molecules on certain serine and threonine amino acid residues in target protein substrates within cells. Phosphorylation of such target protein substrates often results in the modification of their specific activities or function.

As illustrated herein GSK3 inhibitors can facilitate reprogramming of differentiated cells to the cardiac cell lineage. Examples of GSK3 inhibitors that can be employed include one or more of the following compounds:

CHIR99021 (6-(2-(4-(2,4-dichlorophenyl)-5-(4-methyl-1H-imidazol-2-yl)pyrimidin-2-ylamino)ethylamino) nicotinonitrile);

1-azakenpaullone (9-Bromo-7,12-dihydro-pyrido[3',2':2,3] azepino[4,5-b]indol-6(5H)-one), BIO ((2'Z,3'E)-6-Bromoindirubin-3'-oxime);

AR-A014418 (N-(4-Methoxybenzyl)-N'-(5-nitro-1,3-thiazol-2-yl)urea);

Indirubin-3'-monoxime;

5-Iodo-indirubin-3'-monoxime;

kenpaullone (9-Bromo-7,12-dihydroindolo-[3,2-d][1]benzazepin-6(5H)-one);

SB-415286 (3-[(3-Chloro-4-hydroxyphenyl)amino]-4-(2-nitro-phenyl)-1H-pyrrole-2,5-dione);

SB-216763 (3-(2,4-Dichlorophenyl)-4-(1-methyl-1H-indol-3-yl)-1H-pyrrole-2,5-dione);

Maybridge SEW00923SC (2-anilino-5-phenyl-1,3,4-oxadiazole);

(Z)-5-(2,3-Memylenedioxyphenyl)imidazolidine-2,4-dione,

TWS119 (3-(6-(3-aminophenyl)-7H-pyrrolo[2,3-d]pyrimidin-4-yloxy)phenol);

CHIR98014 (N2-(2-(4-(2,4-dichlorophenyl)-5-(1H-imidazol-1-yl)pyrimidin-2-ylamino)ethyl)-5-nitropyridine-2,6-diamine);

SB415286 (3-(3-chloro-4-hydroxyphenylamino)-4-(2-nitrophenyl)-1H-pyrrole-2,5-dione);

Tideglusib (also known as NP031112, or NP-12; 1,2,4-Thiadiazolidine-3,5-dione, 2-(1-naphthalenyl)-4-(phenylmethyl));

LY2090314 (1H-Pyrrole-2,5-dione, 3-imidazo[1,2-a]pyridin-3-yl-4-[1,2,3,4-tetrahydro-2-(1-piperidinylcarbonyl)pyrrolo[3,2,1-jk][1,4]benzodiazepin-7-yl]);

lithium salt (e.g., LiCl); or any combination thereof.

GSK-inhibitors can also include small-interfering RNAs (siRNA) of GSK (Cell Signaling), lithium (Sigma), kenpaullone (Biomol International, Leost, Metal (2000) *Eur J Biochem* 267, 5983-5994), 6-Bromoindirubin-30-acetoxime (Meyer, L et al (2003) *Chem Biol* 10, 1255-1266), SB 216763 and SB 415286 (Sigma-Aldrich), and FRAT-family members and FRAT-derived peptides that prevent interaction of GSK-3 with axin. An overview is provided by Meijer et al, (2004) *Trends in Pharmacological Sciences* 25, 471-480, which is hereby incorporated by reference in its entirety. GSK3 inhibitors that can be used in the compositions and methods described herein can also include those disclosed in US 20120329152 by Pera et al., which is specifically incorporated herein in its entirety.

The GSK3 inhibitor can, for example, be CHIR99021, SB216763, TWS119, CHIR98014, Tideglusib, SB415286, LY2090314, or any combination thereof. In some embodiments, the GSK3 inhibitor can be CHIR99021, whose structure is shown below.

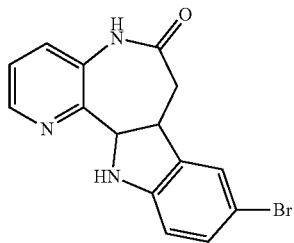 [SMILES: O=C1CC2c3cc(Br)ccc3NC2c2ncccc2N1]

The GSK3 inhibitors can also be in the form of a salt or hydrate of any of the foregoing compounds.

The GSK3 inhibitors can be employed in the compositions and methods described herein in a variety of amounts and/or concentrations. For example, the GSK3 inhibitor can be employed at a concentration of about 0.01 micromolar to about 10 millimolar in a solution, or about 0.1 micromolar to about 100 micromolar in a solution, or about 1 micromolar to about 20 micromolar in a solution, or about 5 micromolar to about 15 micromolar in a solution. In a dry formulation, the GSK3 inhibitor can be present in amounts of about 0.01 mg to about 1000 mg, or about 1 mg to about 100 mg, or about 1 mg to about 10 mg can be present in amounts of about 0.01 mg to about 1000 mg, or about 1 mg to about 100 mg, or about 1 mg to about 10 mg.

Methods and assays for determining a level of GSK-3 inhibition are available to a skilled person and include, for example, the methods and assays described in Liao et al., *Endocrinology*, 145(6): 2941-2949 (2004); and in U.S. Pat. No. 8,323,919, both of which are specifically incorporated by reference herein in their entireties.

TGF-beta Inhibitors

As illustrated herein use of one or more transforming growth factor-beta (TGF-β) inhibitors can facilitate conversion of differentiated cells into the cardiac cell lineage.

There are about thirty members of the transforming growth factor-beta (TGF-β) superfamily, including Activin, Nodal, and BMPs. These TGF-β family members elicit their responses through a variety of cell surface receptors that activate Smad protein signaling cascades.

A TGF-beta inhibitor can directly or indirectly, negatively regulate TGF-beta signaling. In some embodiments, one or more TGF-beta inhibitors binds to and reduces the activity of one or more serine/threonine protein kinases selected from the group consisting of ALK5, ALK4, TGF-beta receptor kinase 1 and ALK7. ALK4, ALK5 and ALK7 are all closely related receptors of the TGF-beta superfamily. Desirable TGF-beta inhibitors can bind to and reduce the activity of ALK4, ALK5 (TGF-beta receptor kinase 1) and/or ALK7. In another embodiment, the TGF-beta receptor binds to and reduces the activity of a Smad protein, for example R-SMAD or SMAD1-5 (i.e. SMAD 1, SMAD 2, SMAD 3, SMAD 4 or SMAD 5).

Examples of TGF-β inhibitors include, but are not limited to:

SB431542 (also known as 4-[4-(1,3-benzodioxol-5-yl)-5-(2-pyridinyl)-1H-imidazol-2-yl]benzamide; available from Tocris Bioscience), which is a potent and selective inhibitor of the transforming growth factor-β (TGF-β) type I receptor activin receptor-like kinase ALK5 ($IC_{50}$=94 nM), and its relatives ALK4 and ALK7;

3-(6-Methyl-2-pyridinyl)-N-phenyl-4-(4-quinolinyl)-1H-pyrazole-1-carbothioamide (also known as A83-01 available from Tocris Bioscience), which is a TGFβ kinase/Activin receptor like kinase (ALK5), type I Activin/nodal receptor ALK4, and type I nodal receptor ALK7 inhibitor (IC50 values can, e.g., be 12, 45 and 7.5 nM respectively) that blocks the phosphorylation of Smad2 and inhibits TGFβ-induced epithelial-to-mesenchymal transition;

4-[4-(1,3-benzodioxol-5-yl)-5-(2-pyridinyl)-1H-imidazol-2-yl]benzamide (also known as SB 431542 and available from Tocris Bioscience; a potent and selective inhibitor of TGF-β type I receptor Activin receptor-like kinase ALK5 (e.g., with $IC_{50}$=94 nM), and its relatives ALK4 and ALK7);

2-(3-(6-Methylpyridine-2-yl)-1H-pyrazol-4-yl)-1,5-naphthyridine (also known as SJN 2511 from Tocris Bioscience; selective inhibitor of the TGF-β type I receptor ALK5 (IC50 values can, e.g., be 0.004 and 0.023 μM for ALK5 autophosphorylation and ALK5 binding, respectively);

4-[4-(2,3-Dihydro-1,4-benzodioxin-6-yl)-5-(2-pyridinyl)-1H-imidazol-2-yl]benzamide (also known as D 4476 from Tocris Bioscience; a selective inhibitor of casein kinase 1 (CK1) and TGF-β type-1 receptor (ALK5) that displays greater than 20-fold selectivity over SAPK2/p38);

4-[3-(2-Pyridinyl)-1H-pyrazol-4-yl]-quinoline (also known as LY 364947 from Tocris Bioscience; a selective inhibitor of TGF-β type-I receptor (TGF-β R1, TGFR-I, TβR-1, ALK-5) (IC50 values can, e.g., be 59, 400 and 1400 nM for TGR-β RI, TGF-β RII and MLK-7K respectively);

2-(4-(benzo[d][1,3]dioxol-5-yl)-2-tert-butyl-1H-imidazol-5-yl)-6-methylpyridine (also known as SB505124, and available from Selleckchem.com; a selective inhibitor of ALK4 and ALKS (e.g., with IC50 of 129 nM and 47 nM, respectively);

6-[2-(1,1-Dimethylethyl)-5-(6-methyl-2-pyridinyl)-1H-imidazol-4-yl]quinoxaline (also known as SB 525334 from Sigma-Aldrich; a selective inhibitor of transforming growth factor-β receptor I (ALKS, TGF-βRI), with IC50=14.3 nM, for example);

2-(5-Chloro-2-fluorophenyl)-4-[(4-pyridyl)amino]pteridine (also known as SD 208 from Tocris Bioscience; a potent, orally active ATP-competitive transforming growth factor-β receptor 1 (TGF-βRI) inhibitor, e.g., with IC50=49 nanomolar);

4-(6-(4-(piperazin-1-yl)phenyl)pyrazolo[1,5-a]pyrimidin-3-yl)quinoline (also known as LDN-193189 from Miltenyi Biotec); and any combination thereof.

The inhibitor that directly or indirectly negatively regulates TGF-beta signaling can, for example, be selected from the group consisting of SB431542, A83-01, SB-431542, A83-01, SJN-2511, LY-36494, SB-505124, SB-525334, and SD-208. In some embodiments, an inhibitor that directly or indirectly negatively regulates TGF-beta signaling can inhibit ALK4, ALK5 and/or ALK7. For example, the inhibitor that directly or indirectly negatively regulates TGF-beta signaling can be SB431542.

The TGF-beta inhibitor can also be in the form of a salt or hydrate of any of the foregoing compounds.

The TGF-beta inhibitor can be employed in the compositions and methods described herein in a variety of amounts and/or concentrations. For example, the TGF-beta inhibitor can be employed in a solution at a concentration of about 0.001 micromolar to about 10 millimolar, or about 0.01 micromolar to about 100 micromolar, or about 0.05 micromolar to about 10 micromolar, or about 0.5 micromolar to about 5 micromolar. In a dry formulation, the TGF-beta inhibitor can be present in amounts of about 0.01 mg to about 1000 mg, or about 1 mg to about 100 mg, or about 1 mg to about 10 mg, or about 0.01 mg to about 200 mg, or about 0.05 mg to about 100 mg, or about 0.1 mg to about 20 mg.

Various methods for determining if a substance is a TGF-beta inhibitor are known. For example, a cellular assay may be used, in which cells are stably transfected with a reporter construct comprising the human PAI-1 promoter or Smad binding sites, driving a luciferase reporter gene Inhibition of luciferase activity relative to control groups can be used as a measure of compound activity (De Gouville et al., *Br J Pharmacol.* 2005 May; 145(2): 166-177). Another example is the AlphaScreen® phosphosensor assay for measurement of kinase activity (Drew et al., Comparison of 2 Cell-Based Phosphoprotein Assays to Support Screening and Development of an ALK Inhibitor, *J Biomol Screen* 16(2) 164-173, 2011).

Epigenetic Modulators

As illustrated herein use of one or more epigenetic modulators can facilitate conversion of differentiated cells into the cardiac cell lineage.

As defined herein, the term "epigenetic modifier" refers to a methylation modifying agent (i.e., agents that induce methylation changes to DNA or histones) and/or an acetylation modifying agent (i.e., agents that induce acetylation changes to DNA or histones). In some embodiments, the methylation modifying agent is a DNA methylation inhibitor (e.g., a DNA methyltransferase (DNMT) inhibitor such as RG108), a histone methylation inhibitor and/or a histone demethylation inhibitor. In some embodiments, the acetylation modifying agent is a histone deacetylase (HDAC) inhibitor (e.g., valproic acid or VPA), a histone acetyltransferase (HAT) inhibitor, a histone deacetylase, and/or a histone acetyltransferase. In some embodiments, epigenetic modifiers are agents that inhibit methyltranferases or demethylases or agents that activate methyltranferases or demethylases.

The epigenetic modifier can be an agent that inhibits histone H3K4 demethylation or activates H3K4 methylation. For example, the agent can inhibit lysine-specific demethylase 1. Exemplary inhibitors of lysine-specific demethylase 1 include, but are not limited to, parnate (tranylcypromine sulfate or equivalent salt) and phenelzine (Nardil, 2-phenylethylhydrazine). See, also, Huang et al., *Proc Natl Acad Sci USA* 104(19): 8023-8028 (2007); Bi, X. et al., *Bioorg. Med. Chem. Lett.* 16:3229-3232 (2006); International Patent Application Nos. WO2007/021839 and WO2008/127734.

In some embodiments, the epigenetic modifier is an agent that inhibits histone H3K9 methylation or promotes H3K9 demethylation, e.g., a G9a histone methyltransferase such as BIX01294.

Exemplary epigenetic modulators include an inhibitor of histone H3K4 demethylation or an activator of H3K4 methylation. Exemplary epigenetic modifiers include, e.g., histone demethylase inhibitors such as LSD1 inhibitors (e.g., parnate) or MAO inhibitors.

The epigenetic modulator or modifier can be employed in the compositions and methods described herein in a variety of amounts and/or concentrations. For example, the epigenetic modifier can be employed at a concentration of about 0.001 micromolar to about 10 millimolar, or about 0.01 micromolar to about 100 micromolar, or about 0.05 micromolar to about 10 micromolar, or about 0.5 micromolar to about 5 micromolar in a solution. In a dry formulation, the TGF-beta inhibitor can be present in amounts of about 0.01 mg to about 200 mg, or about 0.05 mg to about 100 mg, or about 0.1 mg to about 20 mg.

Adenylyl Cyclase Agonist(s)

As illustrated herein use of one or more adenylyl cyclase agonists can facilitate conversion of differentiated cells into the cardiac lineage.

Adenylyl cyclase agonists stimulate the production of cyclic AMP (cAMP) in mammalian cells. One example of an adenylyl cyclase agonist is Forskolin (also known as Colforsin, Coleonol, Boforsin, colforsina, colforsine, colforsinum), which, for example, can have an IC50 of about 0.04-0.15 µM for adenylate cyclase 1. Another example of an adenylyl cyclase agonist is CGP 12177 (4-[3-[(1,1-Dimethylethyl)amino]2-hydroxypropoxy]-1,3-dihydro-2H-benzimidazol-2-one hydrochloride, available from Tocris Bioscience).

The adenylyl cyclase agonist(s) can be employed in the compositions and methods described herein in a variety of amounts and/or concentrations. For example, the adenylyl cyclase agonist(s) can be employed in a solution at a concentration of about 0.01 micromolar to about 10 millimolar, or about 0.1 micromolar to about 100 micromolar, or about 1 micromolar to about 20 micromolar, or about 5 micromolar to about 15 micromolar. In a dry formulation, the adenylyl cyclase agonist(s) can be present in amounts of about 0.01 mg to about 200 mg, or about 0.05 mg to about 100 mg, or about 0.05 mg to about 50 mg, or about 0.1 mg to about 25 mg, or about 0.1 mg to about 20 mg, or about 1 mg to about 8 mg.

Oct Polypeptide

As illustrated herein, use of an Oct polypeptide as a transcription factor can facilitate conversion of differentiated cells into the cardiac lineage.

An "Oct polypeptide" refers to any of the naturally-occurring members of Octamer family of transcription factors, or variants thereof that maintain transcription factor activity, similar (within at least 50%, 80%, or 90% activity) compared to the closest related naturally occurring family member, or polypeptides comprising at least the DNA-binding domain of the naturally occurring family member, and can further include a transcriptional activation domain. Exemplary Oct polypeptides include, Oct-1, Oct-2, Oct-3/4, Oct-6, Oct-7, Oct-8, Oct-9, and Oct-11. For example, Oct3/4 (referred to herein as "Oct4") contains the POU domain, a 150 amino acid sequence conserved among Pit-1, Oct-1, Oct-2, and uric-86. See, Ryan, A. K. & Rosenfeld, M. G.

*Genes Dev.* 11, 1207-1225 (1997). In some embodiments, variants have at least 85%, 90%, or 95% amino acid sequence identity across their whole sequence compared to a naturally occurring Oct polypeptide family member such as to those listed above or such as those listed in the National Center for Biotechnology Information (NCBI) database at ncbi.nlm.nih.gov. For example, one Oct polypeptide sequence is available in the NCBI database with accession number NP_002692.2 (human Oct4), shown below as SEQ ID NO:1.

```
  1  MAGHLASDFA FSPPPGGGGD GPGGPEPGWV DPRTWLSFQG
 41  PPGGPGIGPG VGPGSEVWGI PPCPPPYEFC GGMAYCGPQV
 81  GVGLVPQGGL ETSQPEGEAG VGVESNSDGA SPEPCTVTPG
121  AVKLEKEKLE QNPEESQDIK ALQKELEQFA KLLKQKRITL
161  GYTQADVGLT LGVLFGKVFS QTTICRFEAL QLSFKNMCKL
201  RPLLQKWVEE ADNNENLQEI CKAETLVQAR KRKRTSIENR
241  VRGNLENLFL QCPKPTLQQI SHIAQQLGLE KDVVRVWFCN
281  RRQKGKRSSS DYAQREDFEA AGSPFSGGPV SFPLAPGPHF
321  GTPGYGSPHF TALYSSVPFP EGEAFPPVSV TTLGSPMHSN
```

A cDNA nucleotide sequence for the human Oct4 polypeptide having SEQ ID NO:1 is available in the NCBI database as accession number NM_002701.4 (GI: 116235483), which is shown below as SEQ ID NO:2.

```
  1  CCTTCGCAAG CCCTCATTTC ACCAGGCCCC CGGCTTGGGG
 41  CGCCTTCCTT CCCCATGGCG GGACACCTGG CTTCGGATTT
 81  CGCCTTCTCG CCCCCTCCAG GTGGTGGAGG TGATGGGCCA
121  GGGGGGCCGG AGCCGGGCTG GGTTGATCCT CGGACCTGGC
161  TAAGCTTCCA AGGCCCTCCT GGAGGGCCAG GAATCGGGCC
201  GGGGGTTGGG CCAGGCTCTG AGGTGTGGGG GATTCCCCCA
241  TGCCCCCCGC CGTATGAGTT CTGTGGGGGG ATGGCGTACT
281  GTGGGCCCCA GGTTGGAGTG GGGCTAGTGC CCAAGGCGG
321  CTTGGAGACC TCTCAGCCTG AGGGCGAAGC AGGAGTCGGG
361  GTGGAGAGCA ACTCCGATGG GGCCTCCCCG GAGCCCTGCA
401  CCGTCACCCC TGGTGCCGTG AAGCTGGAGA AGGAGAAGCT
441  GGAGCAAAAC CCGGAGGAGT CCCAGGACAT CAAAGCTCTG
481  CAGAAAGAAC TCGAGCAATT TGCCAAGCTC CTGAAGCAGA
521  AGAGGATCAC CCTGGGATAT ACACAGGCCG ATGTGGGGCT
561  CACCCTGGGG GTTCTATTTG GGAAGGTATT CAGCCAAACG
601  ACCATCTGCC GCTTTGAGGC TCTGCAGCTT AGCTTCAAGA
641  ACATGTGTAA GCTGCGGCCC TTGCTGCAGA AGTGGGTGGA
681  GGAAGCTGAC AACAATGAAA ATCTTCAGGA GATATGCAAA
721  GCAGAAACCC TCGTGCAGGC CCGAAAGAGA AAGCGAACCA
761  GTATCGAGAA CCGAGTGAGA GGCAACCTGG AGAATTTGTT
801  CCTGCAGTGC CCGAAACCCA CACTGCAGCA GATCAGCCAC
841  ATCGCCCAGC AGCTTGGGCT CGAGAAGGAT GTGGTCCGAG
881  TGTGGTTCTG TAACCGGCGC CAGAAGGGCA AGCGATCAAG
921  CAGCGACTAT GCACAACGAG AGGATTTTGA GGCTGCTGGG
961  TCTCCTTTCT CAGGGGGACC AGTGTCCTTT CCTCTGGCCC
1001 CAGGGCCCCA TTTTGGTACC CCAGGCTATG GGAGCCCTCA
1041 CTTCACTGCA CTGTACTCCT CGGTCCCTTT CCCTGAGGGG
1081 GAAGCCTTTC CCCCTGTCTC CGTCACCACT CTGGGCTCTC
1121 CCATGCATTC AAACTGAGGT GCCTGCCCTT CTAGGAATGG
1161 GGGACAGGGG GAGGGGAGGA GCTAGGGAAA GAAAACCTGG
1201 AGTTTGTGCC AGGGTTTTTG GGATTAAGTT CTTCATTCAC
1241 TAAGGAAGGA ATTGGGAACA CAAAGGGTGG GGGCAGGGGA
1281 GTTTGGGGCA ACTGGTTGGA GGGAAGGTGA AGTTCAATGA
1321 TGCTCTTGAT TTTAATCCCA CATCATGTAT CACTTTTTTC
1361 TTAAATAAAG AAGCCTGGGA CACAGTAGAT AGACACACTT
1401 AAAAAAAAAA A
```

Oct polypeptides (e.g., Oct3/4) can be from human, mouse, rat, dog, cat, bovine, porcine, or any other domestic or zoo animal. For example, a mouse Oct4 polypeptide can have the sequence provided in the NCBI database with accession number NP_038661.2 (GI:125490392), which has the following sequence (SEQ ID NO:3).

```
  1  MAGHLASDFA FSPPPGGGDG SAGLEPGWVD PRTWLSFQGP
 41  PGGPGIGPGS EVLGISPCPP AYEFCGGMAY CGPQVGLGLV
 81  PQVGVETLQP EGQAGARVES NSEGTSSEPC ADRPNAVKLE
121  KVEPTPEESQ DMKALQKELE QFAKLLKQKR ITLGYTQADV
161  GLTLGVLFGK VFSQTTICRF EALQLSLKNM CKLRPLLEKW
201  VEEADNNENL QEICKSETLV QARKRKRTSI ENRVRWSLET
241  MFLKCPKPSL QQITHIANQL GLEKDVVRVW FCNRRQKGKR
281  SSIEYSQREE YEATGTPFPG GAVSFPLPPG PHFGTPGYGS
321  PHFTTLYSVP FPEGEAFPSV PVTALGSPMH SN
```

A cDNA nucleotide sequence for the mouse Oct4 polypeptide having SEQ ID NO:3 is available in the NCBI database as accession number NM_013633.3 (GI: 356995852), which is shown below as SEQ ID NO:4.

```
  1  GAGGTGAAAC CGTCCCTAGG TGAGCCGTCT TTCCACCAGG
 41  CCCCCGGCTC GGGGTGCCCA CCTTCCCCAT GGCTGGACAC
 61  CTGGCTTCAG ACTTCGCCTT CTCACCCCCA CCAGGTGGGG
121  GTGATGGGTC AGCAGGGCTG GAGCCGGGCT GGGTGGATCC
161  TCGAACCTGG CTAAGCTTCC AAGGGCCTCC AGGTGGGCCT
201  GGAATCGGAC CAGGCTCAGA GGTATTGGGG ATCTCCCCAT
241  GTCCGCCCGC ATACGAGTTC TGCGGAGGGA TGGCATACTG
281  TGGACCTCAG GTTGGACTGG GCCTAGTCCC CAAGTTGGC
```

```
321   GTGGAGACTT TGCAGCCTGA GGGCCAGGCA GGAGCACGAG
361   TGGAAAGCAA CTCAGAGGGA ACCTCCTCTG AGCCCTGTGC
401   CGACCGCCCC AATGCCGTGA AGTTGGAGAA GGTGGAACCA
441   ACTCCCGAGG AGTCCCAGGA CATGAAAGCC CTGCAGAAGG
481   AGCTAGAACA GTTTGCCAAG CTGCTGAAGC AGAAGAGGAT
521   CACCTTGGGG TACACCCAGG CCGACGTGGG GCTCACCCTG
561   GGCGTTCTCT TTGGAAAGGT GTTCAGCCAG ACCACCATCT
601   GTCGCTTCGA GGCCTTGCAG CTCAGCCTTA AGAACATGTG
641   TAAGCTGCGG CCCCTGCTGG AGAAGTGGGT GGAGGAAGCC
681   GACAACAATG AGAACCTTCA GGAGATATGC AAATCGGAGA
721   CCCTGGTGCA GGCCCGGAAG AGAAAGCGAA CTAGCATTGA
761   GAACCGTGTG AGGTGGAGTC TGGAGACCAT GTTTCTGAAG
801   TGCCCGAAGC CCTCCCTACA GCAGATCACT CACATCGCCA
841   ATCAGCTTGG GCTAGAGAAG GATGTGGTTC GAGTATGGTT
881   CTGTAACCGG CGCCAGAAGG GCAAAAGATC AAGTATTGAG
921   TATTCCCAAC GAGAAGAGTA TGAGGCTACA GGGACACCTT
961   TCCCAGGGGG GGCTGTATCC TTTCCTCTGC CCCCAGGTCC
1001  CCACTTTGGC ACCCCAGGCT ATGGAAGCCC CCACTTCACC
1041  ACACTCTACT CAGTCCCTTT TCCTGAGGGC GAGGCCTTTC
1081  CCTCTGTTCC CGTCACTGCT CTGGGCTCTC CCATGCATTC
1121  AAACTGAGGC ACCAGCCCTC CCTGGGGATG CTGTGAGCCA
1161  AGGCAAGGGA GGTAGACAAG AGAACCTGGA GCTTTGGGGT
1201  TAAATTCTTT TACTGAGGAG GGATTAAAAG CACAACAGGG
1241  GTGGGGGGTG GGATGGGGAA AGAAGCTCAG TGATGCTGTT
1281  GATCAGGAGC CTGGCCTGTC TGTCACTCAT CATTTTGTTC
1321  TTAAATAAAG ACTGGGACAC ACAGTAGATA GCT
```

Generally, the same species of protein will be used with the species of cells being manipulated. However, even within a species there can be sequence variation from one individual protein to the next, but the protein can still perform the same function. Hence, a selected Oct polypeptide or Oct nucleic acid can also have some sequence variation. For example, an Oct4 polypeptide can have at least 80%, or at least 85%, or at least 90%, or at least 95%, or at least 96%, or at least 97%, or at least 98%, or at least 99% sequence identity to the SEQ ID NO:1 or 3 amino acid sequences. Similarly, a coding region of an Oct4 nucleic acid selected for generating a transgenic expression cassette, or for induction of endogenous expression, can have at least 80%, or at least 85%, or at least 90%, or at least 95%, or at least 96%, or at least 97%, or at least 98%, or at least 99% sequence identity to the SEQ ID NO:2 or SEQ ID NO:4 cDNA sequences.

Oct Polypeptide Expression/Translation in Selected Cells

As described herein, differentiated cells can be reprogrammed to the cardiac lineage by incubation of the differentiated cells with the compositions described herein after or during expression of the Oct polypeptide in the selected differentiated cells.

In some embodiments, the transcription factor(s) employed to reprogram cells to the cardiac lineage can be introduced into a selected cell or a selected population of cells by a recombinant expression vector. Techniques in the field of recombinant genetics can be used for such transformation. Basic texts disclosing general methods of recombinant genetics include Sambrook et al., *Molecular Cloning, A Laboratory Manual* (3rd ed. 2001); Kriegler, *Gene Transfer and Expression: A Laboratory Manual* (1990); and *Current Protocols in Molecular Biology* (Ausubel et al., eds., 1994)).

In some embodiments, the species of cell and the species of the protein to be expressed are the same. For example, if a mouse cell is used, a mouse ortholog is introduced into the cell. If a human cell is used, a human ortholog is introduced into the cell.

It will be appreciated that where two or more proteins are to be expressed in a cell, one or multiple RNA molecules or expression cassettes can be used. For example, one expression cassette can express multiple polypeptides, and a polycistronic expression cassette can be used. In some embodiments, the vectors do not contain a mammalian origin of replication. In some embodiments, the expression vector is not integrated into the genome and/or is introduced via a vector that does not contain a mammalian origin of replication.

The selected cell for expression of the Oct polypeptide (and contacting with the compositions described herein) can be a mixture or population of cells. For example, the selected cell can be a differentiated, non-cardiac cell (or a mixture of differentiated, non-cardiac cells). The selected cell(s) can be mammalian cells that are not pluripotent cells. Mammalian cells can be from humans or non-human mammals. Exemplary non-human mammals include, but are not limited to, mice, rats, cats, dogs, rabbits, guinea pigs, hamsters, sheep, pigs, horses, bovines, and non-human primates (e.g., chimpanzees, macaques, and apes). Examples of selected cells include differentiated cells as well as progenitor cells. Examples of differentiated cells include, but are not limited to, cells from a tissue selected from fibroblasts, bone marrow, skin, skeletal muscle, fat tissue and peripheral blood cells. Exemplary cell types include, but are not limited to, fibroblasts, hepatocytes, myoblasts, neurons, squamous cells, osteoblasts, osteoclasts, and T-cells.

The Oct polypeptide can be introduced, translated, and/or expressed within selected cells by a variety of procedures. In some embodiments, the Oct polypeptide is expressed transiently in the selected cells (e.g., for 2-10 days, or 2-8 days or 2-6 days) either before or during exposure of the cells to the reprogramming composition.

Endogenous expression of an Oct polypeptide can be increased by introduction of microRNA-302 (miR-302), or by increased expression of miR-302. See, e.g., Hu et al., *Stem Cells* 31(2): 259-68 (2013), which is incorporated herein by reference in its entirety. Hence, miRNA-302 can be an inducer of endogenous Oct polypeptide expression. The miRNA-302 can be introduced alone or with a nucleic acid that encodes the Oct polypeptide.

Direct Translation from Introduced RNA

When the Oct polypeptide is expressed transiently in the selected cells, the Oct polypeptide can be introduced as an RNA molecule, which is translated to protein within the cell's cytoplasm. For example, the Oct polypeptide can be translated from introduced RNA molecules that have the open reading frame (ORF) for the Oct polypeptide flanked by a 5' untranslated region (UTR) containing a translational initiation signal (e.g., a strong Kozak translational initiation signal) and a 3' untranslated region terminating with an oligo(dT) sequence for templated addition of a polyA tail. Such RNA molecules do not have the promoter sequences employed in most expression vectors and expression cassettes. The RNA molecules can be introduced into the selected cells by a variety of techniques, including electroporation or by endocytosis of the RNA complexed with a cationic vehicle. See, e.g., Warren et al., *Cell Stem Cell* 7: 618-30 (2010), incorporated herein by reference in its entirety.

Protein translation can persist for several days, especially when the RNA molecules are stabilized by incorporation of modified ribonucleotides. For example, incorporation of 5-methylcytidine (5mC) for cytidine and/or pseudouridine (psi) for uridine can improve the half-life of the introduced RNA in vivo, and lead to increased protein translation. If high levels of expression are desired, or expression for more than a few days is desired, the RNA can be introduced repeatedly into the selected cells.

The RNA encoding the Oct polypeptide can also include a 5' cap, a nuclear localization signal, or a combination thereof. See, e.g., Warren et al., *Cell Stem Cell* 7: 618-30 (2010).

Such RNA molecules can be made, for example, by in vitro transcription of an Oct template using a ribonucleoside blend that includes a 3'-O-Me-m7G(5')ppp(5')G ARCA cap analog (New England Biolabs), adenosine triphosphate and guanosine triphosphate (USB, Cleveland, Ohio), 5-methylcytidine triphosphate and pseudouridine triphosphate (Tri-Link Biotechnologies, San Diego, Calif.). The RNA molecules can also be treated with phosphatase to reduce cytotoxicity.

The Oct RNA can be introduced alone or with miRNA-302, which can be an inducer of endogenous Oct polypeptide expression. The miRNA-302 functions as a structural RNA that does not encode a protein. Hence, no translation is needed for miRNA-302 to perform its function. The miRNA-302 can be introduced directly into cells, for example, in a delivery vehicle such as a liposome, microvesicle, or exosome. Alternatively, the miRNA-302 can be expressed from an expression cassette or expression vector that has been introduced into a cell or a cell population.

Promoters and Enhancers

An expression cassette, plasmid, or vector can also be used to transform a selected cell with a nucleic acid segment that encodes the Oct polypeptide and/or miRNA-302. The Oct polypeptide and the miRNA-302 can be encoded by the same or by different expression cassettes, plasmids, or vectors.

Such an expression cassette, plasmid, or vector can have regulatory sequences operably linked to the coding region of the Oct polypeptide to allow expression of the Oct mRNA and polypeptide. Similarly, regulatory sequences can be used to drive the expression of miRNA-302. A variety of plasmids and/or vectors can be used to introduce nucleic acids encoding one or more Oct4 polypeptides and/or miRNA-302 into a selected cell (also referred to as a "starting cell" or a "host cell"). In some embodiments, the plasmid or vector does not integrate into the genome of the cells and does not contain a mammalian origin of replication.

A nucleic acid encoding the Oct polypeptide and/or miRNA-302 can be operably linked to a promoter and/or enhancer to facilitate expression of the polypeptide. Separate promoters and/or enhancers can be employed for the Oct and miRNA-302 coding regions.

The promoter can be one naturally associated with an Oct gene or nucleic acid segment. Similarly, for miRNA-302, the promoter can be one naturally associated with an miRNA-302 gene. Such a naturally associated promoter can be referred to as the "natural promoter" and may be obtained by isolating the 5' non-coding sequences located upstream of the coding segment and/or exon. Similarly, an enhancer may be one naturally associated with a nucleic acid sequence. However, the enhancer can be located either downstream or upstream of that sequence.

Alternatively, certain advantages will be gained by positioning the coding nucleic acid segment (e.g., for the Oct polypeptide or the miRNA-302) under the control of a recombinant or heterologous promoter, which refers to a promoter that is not normally associated with a nucleic acid in its natural environment. A recombinant or heterologous enhancer refers also to an enhancer not normally associated with a nucleic acid sequence in its natural environment. Such promoters or enhancers can include promoters or enhancers of other genes, and promoters or enhancers isolated from any other prokaryotic, viral, or eukaryotic cell, and promoters or enhancers not "naturally occurring," i.e., containing different elements of different transcriptional regulatory regions, and/or mutations that alter expression. In addition to producing nucleic acid sequences of promoters and enhancers synthetically, sequences may be produced using recombinant cloning and/or nucleic acid amplification technology, including PCR™, in connection with the compositions disclosed herein (see U.S. Pat. Nos. 4,683,202, 5,928,906, each incorporated herein by reference).

The promoters employed may be constitutive, inducible, developmentally-specific, tissue-specific, and/or useful under the appropriate conditions to direct high level expression of the nucleic acid segment. For example, the promoter can be a constitutive promoter such as, a CMV promoter, a CMV cytomegalovirus immediate early promoter, a CAG promoter, an EF-1α promoter, a HSV1-TK promoter, an SV40 promoter, a β-actin promoter, a PGK promoter, or a combination thereof. Examples of eukaryotic promoters that can be used include, but are not limited to, constitutive promoters, e.g., viral promoters such as CMV, SV40 and RSV promoters, as well as regulatable promoters, e.g., an inducible or repressible promoter such as the tet promoter, the hsp70 promoter and a synthetic promoter regulated by CRE. In certain embodiments, cell type-specific promoters are used to drive expression of reprogramming factors in specific cell types. Examples of suitable cell type-specific promoters useful for the methods described herein include, but are not limited to, the synthetic macrophage-specific promoter described in He et al (2006), *Human Gene Therapy* 17:949-959; the granulocyte and macrophage-specific lysozyme M promoter (see, e.g., Faust et al (2000), *Blood* 96(2):719-726); and the myeloid-specific CD11b promoter (see, e.g., Dziennis et al (1995), *Blood* 85(2):319-329). Other examples of promoters that can be employed include a human EF1α elongation factor promoter, a CMV cytomegalovirus immediate early promoter, a CAG chicken albumin promoter, a viral promoter associated with any of the viral vectors described herein, or a promoter that is homologous to any of the promoters described herein (e.g., from another species). Examples of prokaryotic promoters that can be used include, but are not limited to, SP6, T7, T5, tac, bla, trp, gal, lac, or maltose promoters.

In some embodiments, an internal ribosome entry sites (IRES) element can be used to create multigene, or polycistronic, messages. IRES elements are able to bypass the ribosome scanning model of 5'-methylated Cap dependent translation and begin translation at internal sites (Pelletier and Sonenberg, *Nature* 334(6180):320-325 (1988)). IRES elements from two members of the picornavirus family (polio and encephalomyocarditis) have been described (Pelletier and Sonenberg, *Nature* 334(6180):320-325 (1988)), as well an IRES from a mammalian message (Macejak & Samow, *Nature* 353:90-94 (1991)). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message (see U.S. Pat. Nos. 5,925,565 and 5,935,819, herein incorporated by reference).

Plasmid Vectors

A plasmid vector can be used to introduce an expression cassette into a selected cell. In general, plasmid vectors containing control sequences (e.g., promoters, enhancers, etc.) which are derived from species compatible with the cell are used in connection with these hosts. The vector can also contain a nucleic acid segment encoding a marker capable of providing phenotypic selection in transformed cells. While a plasmid vector can contain a prokaryotic origin of replication, in some embodiments, the vectors do not contain a mammalian origin of replication.

Viral Vectors

The ability of certain viruses to infect cells or enter cells via receptor-mediated endocytosis, and express viral genes stably and efficiently have made them attractive candidates for the transfer of foreign nucleic acids into cells (e.g., mammalian cells). Viral vectors can include control sequences such as promoters for expression of the Oct polypeptide and/or the miRNA-302. Although many viral vectors integrate into the host cell genome, if desired, the segments that allow such integration can be removed or altered to prevent such integration. Moreover, in some embodiments, the vectors do not contain a mammalian origin of replication. Non-limiting examples of virus vectors are described below that can be used to deliver nucleic acids encoding a transcription factor into a selected cell are described below.

i. Adenoviral Vectors

One method for delivery of the nucleic acid into selected cells involves the use of an adenovirus expression vector. Adenovirus vectors can have a low capacity for integration into genomic DNA. Adenoviruses also have a high efficiency of gene transfer afforded by these vectors. "Adenovirus expression vector" is meant to include those constructs containing adenovirus sequences sufficient to express a tissue or cell-specific construct that has been cloned therein. The genetic organization of adenovirus includes an approximate 36 kb, linear, double-stranded DNA virus, which allows substitution of large pieces of adenoviral DNA with foreign sequences up to 7 kb (Grunhaus et al., *Seminar in Virology* 200(2):535-546, 1992)).

ii. AAV Vectors

The nucleic acid may be introduced into the cell using adenovirus assisted transfection. Increased transfection efficiencies have been reported in cell systems using adenovirus coupled systems (Kelleher and Vos, *Biotechniques*, 17(6): 1110-7, 1994; Cotten et al., *Proc Natl Acad Sci USA*, 89(13):6094-6098, 1992; Curiel, *Nat Immun*, 13(2-3):141-64, 1994). Adeno-associated virus (AAV) is an attractive vector system as it has a high frequency of integration and it can infect non-dividing cells, thus making it useful for delivery of genes into mammalian cells, for example, in tissue culture (Muzyczka, *Curr Top Microbiol Immunol*, 158:97-129, 1992) or in vivo. Details concerning the generation and use of rAAV vectors are described in U.S. Pat. Nos. 5,139,941 and 4,797,368, each incorporated herein by reference in its entirety.

iii. Retroviral Vectors

Retroviruses can integrate their genes into the host genome, transfer a large amount of foreign genetic material, infect a broad spectrum of species and cell types, and can be packaged in special cell-lines (Miller et al., *Am. J. Clin. Oncol.*, 15(3):216-221, 1992). In some embodiments, a retroviral vector is altered so that it does not integrate into the host cell genome.

A retroviral vector can be constructed by inserting a nucleic acid (e.g., one encoding a polypeptide of interest such as an Oct polypeptide or an miRNA-302) into the viral genome in the place of some viral sequences to produce a virus that is replication-defective. To produce virions, a packaging cell line containing the gag, pol, and env genes, but without the LTR and packaging components, is constructed (Mann et al., *Cell* 33:153-159, 1983). When a recombinant plasmid containing a cDNA, together with the retroviral LTR and packaging sequences is introduced into a special cell line (e.g., by calcium phosphate precipitation), the packaging sequence allows the RNA transcript of the recombinant plasmid to be packaged into viral particles, which are then secreted into the culture media (Nicolas and Rubinstein, In: *Vectors: A survey of molecular cloning vectors and their uses*, Rodriguez and Denhardt, eds., Stoneham: Butterworth, pp. 494-513, 1988; Temin, In: *Gene Transfer*, Kucherlapati (ed.), New York: Plenum Press, pp. 149-188, 1986; Mann et al., *Cell*, 33:153-159, 1983). The media containing the recombinant retroviruses is then collected, optionally concentrated, and used for gene transfer. Retroviral vectors are able to infect a broad variety of cell types. However, integration and stable expression typically involves the division of host cells (Paskind et al., *Virology*, 67:242-248, 1975).

Lentiviruses are complex retroviruses, which, in addition to the common retroviral genes gag, pol, and env, contain other genes with regulatory or structural function. Information on lentiviral vectors is available, for example, in Naldini et al., *Science* 272(5259):263-267, 1996; Zufferey et al., *Nat Biotechnol* 15(9):871-875, 1997; Blomer et al., *J Virol.* 71(9):6641-6649, 1997; U.S. Pat. Nos. 6,013,516 and 5,994,136, each of which is incorporated herein by reference in its entirety. Some examples of lentivirus include the Human Immunodeficiency Viruses: HIV-1, HIV-2 and the Simian Immunodeficiency Virus: SIV. Lentiviral vectors have been generated by multiply attenuating the HIV virulence genes, for example, the genes env, vif, vpr, vpu and nef are deleted to make the vector biologically safe. The lentivirus employed can also be replication and/or integration defective.

Recombinant lentiviral vectors are capable of infecting non-dividing cells and can be used for both in vivo and ex vivo gene transfer and expression of nucleic acid sequences. For example, recombinant lentivirus capable of infecting a non-dividing cell wherein a suitable host cell is transfected with two or more vectors carrying the packaging functions, namely gag, pol and env, as well as rev and tat is described in U.S. Pat. No. 5,994,136, which is incorporated herein by reference in its entirety. Those of skill in the art can target the recombinant virus by linkage of the envelope protein with an antibody or a particular ligand for targeting to a receptor of a particular cell-type. For example, a target specific vector can be generated by inserting a nucleic acid segment (including a regulatory region) of interest into the viral vector, along with another gene that encodes a ligand for a receptor on a specific target cell type.

iv. Delivery Using Modified Viruses

A nucleic acid to be delivered can be housed within an infective virus that has been engineered to express a specific binding ligand. The virus particle will thus bind with specificity to the cognate receptors of the target cell and deliver the contents to the cell.

Selected (Starting) Cells

Selected cells can be contacted or incubated with the compositions described herein. Such selected cells are also referred to as starting cells. A starting population of cells can be derived from essentially any source, and can be heterogeneous or homogeneous. In certain embodiments, the cells to be treated as described herein are adult cells, including essentially any accessible adult cell type(s). In other embodiments, the cells used according to the invention are adult stem cells, progenitor cells, or somatic cells. In still other embodiments, the cells treated with any of the compositions and/or methods described herein include any type of cell from a newborn, including, but not limited to, newborn cord blood, newborn stem cells, progenitor cells, and tissue-derived cells (e.g., somatic cells). Accordingly, a starting population of cells that is reprogrammed by the compositions and/or methods described herein, can be essentially any live somatic cell type.

As illustrated herein, fibroblasts can be reprogrammed to cross lineage boundaries and to be directly converted to another cell type—a cardiac progenitor cell or a cardiomyocyte cell type.

Various cell types from all three germ layers have been shown to be suitable for somatic cell reprogramming by genetic manipulation, including, but not limited to liver and stomach (Aoi et al., *Science* 321(5889):699-702 (2008); pancreatic β cells (Stadtfeld et al., *Cell Stem Cell* 2: 230-40 (2008); mature B lymphocytes (Hanna et al., *Cell* 133: 250-264 (2008); human dermal fibroblasts (Takahashi et al., *Cell* 131, 861-72 (2007); Yu et al., *Science* 318(5854) (2007); Lowry et al., *Proc Natl Acad Sci USA* 105, 2883-2888 (2008); Aasen et al., *Nat Biotechnol* 26(11): 1276-84 (2008); meningiocytes (Qin et al., *J Biol Chem* 283(48): 33730-5 (2008); neural stem cells (DiSteffano et al., *Stem Cells Devel.* 18(5): (2009); and neural progenitor cells (Eminli et al., *Stem Cells* 26(10): 2467-74 (2008). Any such cells can be reprogrammed and/or programmed by use of the compositions and methods described herein.

The mammalian cells can, for example, be selected from one or more of hepatocytes, fibroblasts, endothelial cells, B cells, T cells, dendritic cells, keratinocytes, adipose cells, epithelial cells, epidermal cells, chondrocytes, cumulus cells, neural cells, glial cells, astrocytes, cardiac cells, esophageal cells, skeletal muscle cells, skeletal muscle satellite melanocytes, hematopoietic cells, osteocytes, macrophages, monocytes, mononuclear cells or stem cells including embryonic stem cells, embryonic germ cells, adult brain stem cells, epidermal stem cells, skin stem cells, pancreatic stem cells, kidney stem cells, liver stem cells, breast stem cells, lung stem cells, muscle stem cells, heart stem cells, eye stem cells, bone stem cells, spleen stem cells, immune system stem cells, cord blood stem cells, bone marrow stem cells and peripheral blood stem cells.

The cells can be autologous or allogeneic cells (relative to a subject to be treated or who may receive the cells).

Nucleic Acid Delivery

Suitable methods for nucleic acid delivery into cells, tissues, or an organism include a variety of procedures by which a nucleic acid (e.g., RNA or DNA) can be introduced into a cell, a tissue or an organism. Examples of procedures include, for example, those described by Stadtfeld and Hochedlinger, *Nature Methods* 6(5):329-330 (2009); Yusa et al., *Nat. Methods* 6:363-369 (2009); Woltjen, et al., *Nature* 458, 766-770 (9 Apr. 2009)). Such methods include, but are not limited to, direct delivery of DNA such as by ex vivo transfection (e.g., Wilson et al., *Science*, 244:1344-1346, 1989, Nabel & Baltimore, *Nature* 326:711-713, 1987), optionally with Fugene6 (Roche) or Lipofectamine (Invitrogen); by injection (e.g., U.S. Pat. Nos. 5,994,624, 5,981,274, 5,945,100, 5,780,448, 5,736,524, 5,702,932, 5,656,610, 5,589,466 and 5,580,859, each incorporated herein by reference), including microinjection (e.g., Harland and Weintraub, *J. Cell Biol.*, 101:1094-1099, 1985; U.S. Pat. No. 5,789,215, incorporated herein by reference in its entirety); by electroporation (e.g., U.S. Pat. No. 5,384,253, incorporated herein by reference in its entirety, Tur-Kaspa et al., *Mol. Cell Biol.*, 6:716-718, 1986; Potter et al., *Proc. Nat'l Acad. Sci. USA*, 81:7161-7165, 1984); by calcium phosphate precipitation (e.g., Graham & Van Der Eb, *Virology*, 52:456-467, 1973; Chen and Okayama, *Mol. Cell Biol.*, 7(8):2745-2752, 1987; Rippe et al., *Mol. Cell Biol.*, 10:689-695, 1990); by use of DEAE-dextran followed by polyethylene glycol (e.g., Gopal, *Mol. Cell Biol.*, 5:1188-1190, 1985); by direct sonic loading (e.g., Fechheimer et al., *Proc. Nat'l Acad. Sci. USA*, 84:8463-8467, 1987); by liposome mediated transfection (e.g., Nicolau & Sene, *Biochim. Biophys. Acta*, 721: 185-190, 1982, Fraley et al., *Proc. Nat'l Acad. Sci. USA*, 76:3348-3352, 1979; Nicolau et al., *Methods Enzymol.*, 149:157-176, 1987, Wong et al., *Gene*, 10:87-94, 1980, Kaneda et al., *Science*, 243:375-378, 1989, Kato et al., *Biol. Chem.*, 266:3361-3364, 1991), receptor-mediated transfection (e.g., Wu and Wu, *Biochemistry*, 27:887-892, 1988; Wu and Wu, *J. Biol. Chem.*, 262:4429-4432, 1987); by endocytosis of the RNA complexed with a cationic vehicle (Warren et al., *Cell Stem Cell* 7: 618-30 (2010)); and any combination of such methods. Each of the foregoing references is incorporated herein by reference in its entirety.

Reprogramming Methods

Selected starting cells are treated for a time and under conditions sufficient to convert the starting cells across lineage and/or differentiation boundaries to form cardiac progenitor cells and/or cardiomyocytes. Expression of the Oct polypeptide in the starting cells should be initiated for at least one day before treatment with the composition described herein. Reprogramming efficiency of the cells can be improved by expression of the Oct polypeptide for at least two days, or at least three days, or at least four days, or at least five days prior to incubation with the compositions described herein. In some embodiments, the cells can express the Oct polypeptide while being treated or incubated with the reprogramming composition described herein. For example, expression of the Oct polypeptide can be induced by contacting the cells with an inducing agent (e.g., expression of miRNA-302) that activates or increases Oct polypeptide expression from a heterologous or endogenous Oct gene. Alternatively, or in addition, RNA molecules encoding the Oct polypeptide can be introduced into the cells prior to incubation of the cells with the reprogramming composition.

Starting cells can be incubated with a reprogramming composition that contains one or more WNT agonists, GSK3 inhibitors, TGF-beta inhibitors, epigenetic modifiers, adenylyl cyclase agonists, Oct-4 expression activators, and any combination thereof. The composition can contain at least two of such agents, or at least three of such agents, or at least four of such agents, or at least five of such agents, or at least six of such agents. For example, the composition can include SB431542 (an ALK4/5/7 inhibitor), CHIR99021 (a GSK3 inhibitor), parnate (an LSD1/KDM1 inhibitor, also called tranylcypromine) and forskolin (an adenylyl cyclase activator).

After incubation of the starting cells in a reprogramming medium, the cells can then incubated in another media, for example, a maintenance media, an expansion media, or a cardiac induction media that can induce further maturation of the cells.

The base media employed to which the reprogramming agents or induction agents are added can be a convenient cell culture medium.

The term "cell culture medium" (also referred to herein as a "culture medium" or "medium") as referred to herein is a medium for culturing cells containing nutrients that maintain cell viability and support proliferation. The cell culture medium can contain any of the following in an appropriate combination: salt(s), buffer(s), amino acids, glucose or other sugar(s), antibiotics, serum or serum replacement, and other components such as peptide growth factors, etc. Cell culture media ordinarily used for particular cell types are available to those skilled in the art.

Examples of cell culture media that can be employed include mTESR-1® medium (StemCell Technologies, Inc., Vancouver, Calif.), or Essential 8® medium (Life Technologies, Inc.) on a Matrigel substrate (BD Biosciences, NJ) or on a Corning® Synthemax surface, or in Johansson and Wiles chemically defined media (CDM) supplemented with insulin, transferrin, lipids and polyvinyl alcohol (PVA) as substitute for Bovine Serum Albumin (BSA). Examples of commercially available media also include, but are not limited to, Dulbecco's Modified Eagle's Medium (DMEM), Minimal Essential Medium (MEM), Basal Medium Eagle (BME), RPM1 1640, Ham's F-10, Ham's F-12, a-Minimal Essential Medium (aMEM), Glasgow's Minimal Essential Medium (G-MEM), Iscove's Modified Dulbecco's Medium, or a general purpose media modified for use with pluripotent cells, such as X-VIVO (Lonza) or a hematopoietic base media.

The starting cells can be dispersed in a cell culture medium that contains the reprogramming composition at a density that permits cell expansion. For example, about 1 to $10^{12}$ cells can be contacted with the reprogramming composition in a selected cell culture medium, especially when the cells are maintained at a cell density of about 1 to about $10^8$ cells per milliliter, or at a density of about 100 to about $10^7$ cells per milliliter, or at a density of about 1000 to about $10^6$ cells per milliliter.

The time for conversion of starting cells into cardiac progenitor and cardiomyocyte cells can vary. For example, the starting cells can be incubated with the reprogramming composition until cardiac or cardiomyocyte cell markers are expressed. Such cardiac or cardiomyocyte cell markers can include any of the following markers: α-GATA4, TNNT2, MYH6, RYR2, NKX2-5, MEF2c, ANP, Actinin, MLC2v, MY20, cMHC, ISL1, cTNT, cTNI, MLC2a and any combination thereof.

Incubation can proceed in any of the compositions described herein, for example, until cardiac progenitor markers are expressed by the starting cells. Such cardiac progenitor markers include Gata4, Tnnt2, Myh6, Ryr2, or a combination thereof. The cardiac progenitor markers such as Gata4, Tnnt2, Myh6, Ryr2, or a combination thereof can be expressed by about 8 days, or by about 9 days, or by about 10 days, or by about 11 days, or by about 12 days, or by about 14 days, or by about 15 days, or by about 16 days, or by about 17 days, or by about 18 days, or by about 19 days, or by about 20 days after starting incubation of cells in the compositions described herein.

Further incubation of the cells can be performed until expression of late stage cardiac progenitor markers such as NKX2-5, MEF2c or a combination thereof occurs. The late stage cardiac progenitor marker such as NKX2-5 and/or MEF2c can be expressed by about 15 days, or by about 16 days, or by about 17 days, or by about 18 days, by about 19 days, or by about 20 days, or by about 21 days, or by about 22 days, or by about 23 days, or by about 24 days, or by about 25 days of incubation of cells using the compositions and methods described herein.

In some embodiments, the starting cells can be incubated with the reprogramming medium under cell culture conditions for about 1 day to about 30 days, or about 2 days to about 27 days, or about 3 days to about 25 days, or about 4 days to about 23 days, or about 5 days to about 20 days, or about 6 days to about 20 days, or about 10 days to about 20 days.

Cardiomyocytes exhibit some cardiac-specific electrophysiological properties. One electrical characteristic is an action potential, which is a short-lasting event in which the difference of potential between the interior and the exterior of each cardiac cell rises and falls following a consistent trajectory. Another electrophysiological characteristic of cardiomyocytes is the cyclic variations in the cytosolic-free $Ca^{2+}$ concentration, named as $Ca^{2+}$ transients, which are employed in the regulation of the contraction and relaxation of cardiomyocytes. These characteristics can be detected and evaluated to assess whether a population of cells has been reprogrammed into cardiomyocytes.

Such methods can therefore be used to generate a population of cardiac progenitor cells or cardiomyocytes that can be transplanted into a subject or used for experimentation.

In some embodiments, a reprogrammed population of cells (at various stages of reprogramming) can be frozen at liquid nitrogen temperatures, stored for periods of time, and then thawed for use at a later date. If frozen, a population of reprogrammed cells can be stored in a 10% DMSO, 50% FCS, within 40% RPMI 1640 medium. Once thawed, the cells can be expanded by culturing the cells in an appropriate medium that can contain selected growth factors, vitamins, feeder cells, and other components selected by a person of skill in the art.

Treatment of a Subject

The reprogrammed cells and compositions of compounds (with or without reprogrammed cells) that are described herein can also be employed in a method of treating a subject with a cardiac disease or condition.

Examples of diseases and conditions that can be treated using the reprogrammed cells and/or compositions (containing any of the compounds described herein with or without reprogrammed cells) include any cardiac pathology or cardiac dysfunction. Diseases and conditions that can be treated include those that occur as a consequence of genetic defect, physical injury, environmental insult or conditioning, bad health, obesity and other disease risk.

The terms "cardiac pathology" or "cardiac dysfunction" are used interchangeably and refer to any impairment in the heart's pumping function. This includes, for example, impairments in contractility, impairments in ability to relax (sometimes referred to as diastolic dysfunction), abnormal or improper functioning of the heart's valves, diseases of the heart muscle (sometimes referred to as cardiomyopathies), diseases such as angina pectoris, myocardial ischemia and/or infarction characterized by inadequate blood supply to the heart muscle, infiltrative diseases such as amyloidosis and hemochromatosis, global or regional hypertrophy (such as may occur in some kinds of cardiomyopathy or systemic hypertension), and abnormal communications between chambers of the heart.

As used herein, the term "cardiomyopathy" refers to any disease or dysfunction of the myocardium (heart muscle) in which the heart is abnormally enlarged, thickened and/or stiffened. As a result, the heart muscle's ability to pump blood is usually weakened. The etiology of the disease or disorder may be, for example, inflammatory, metabolic, toxic, infiltrative, fibroplastic, hematological, genetic, or unknown in origin. There are two general types of cardiomyopathies: ischemic (resulting from a lack of oxygen) and non-ischemic.

Ischemic cardiomyopathy is a chronic disorder caused by coronary artery disease (a disease in which there is atherosclerotic narrowing or occlusion of the coronary arteries on the surface of the heart). Coronary artery disease often leads to episodes of cardiac ischemia, in which the heart muscle is not supplied with enough oxygen-rich blood.

Non-ischemic cardiomyopathy is generally classified into three groups based primarily on clinical and pathological characteristics: dilated cardiomyopathy, hypertrophic cardiomyopathy and restrictive and infiltrative cardiomyopathy.

In another embodiment, the cardiac pathology is a genetic disease such as Duchenne muscular dystrophy and Emery Dreifuss dilated cardiomyopathy.

For example, the cardiac pathology can be selected from the group consisting of congestive heart failure, myocardial infarction, cardiac ischemia, myocarditis and arrhythmia.

Administration

Reprogrammed cells generated as described herein can be employed for tissue reconstitution or regeneration in a human patient or other subjects in need of such treatment. The cells are administered in a manner that permits them to graft or migrate to a diseased or injured tissue site and to reconstitute or regenerate the functionally deficient area. Devices are available that can be adapted for administering cells, for example, to cardiac tissues.

For therapy, cardiac progenitor cells, cardiomyocytes and/or pharmaceutical compositions can be administered locally or systemically. A reprogrammed population of cells can be introduced by injection, catheter, implantable device, or the like. A population of reprogrammed cells can be administered in any physiologically acceptable excipient or carrier that does not adversely affect the cells. For example, the cardiac progenitor cells, cardiomyocytes and/or pharmaceutical compositions can be administered intravenously or through an intracardiac route (e.g., epicardially or intramyocardially). Methods of administering the cardiomyocytes and pharmaceutical compositions of the invention to subjects, particularly human subjects include injection or implantation of the cells into target sites in the subjects, the cells of the invention can be inserted into a delivery device which facilitates introduction by, injection or implantation, of the cells into the subjects. Such delivery devices include tubes, e.g., catheters, for injecting cells and fluids into the body of a recipient subject. The tubes can additionally include a needle, e.g., a syringe, through which the cells of the invention can be introduced into the subject at a desired location.

The cardiac progenitor cells and cardiomyocytes can be inserted into such a delivery device, e.g., a syringe, in different forms. A population of reprogrammed cells can be supplied in the form of a pharmaceutical composition. Such a composition can include an isotonic excipient prepared under sufficiently sterile conditions for human administration. For general principles in medicinal formulation, the reader is referred to *Cell Therapy: Stem Cell Transplantation, Gene Therapy, and Cellular Immunotherapy*, by G. Morstyn & W. Sheridan eds, Cambridge University Press, 1996; and *Hematopoietic Stem Cell Therapy*, E. D. Ball, J. Lister & P. Law, Churchill Livingstone, 2000. The choice of the cellular excipient and any accompanying constituents of the composition that includes a population of reprogrammed cells can be adapted to optimize administration by the route and/or device employed.

As used herein, the term "solution" includes a carrier or diluent in which the cardiomyocytes and cardiac cells of the invention remain viable. Carriers and diluents that can be used include saline, aqueous buffer solutions, solvents and/or dispersion media. The use of such carriers and diluents is well known in the art. The solution is preferably sterile and fluid to the extent that easy syringability exists. For transplantation, cardiomyocytes and/or cardiac cells are drawn up into a syringe and administrated to anesthetized transplantation recipients. Multiple injections may be made using this procedure.

The cardiac progenitor cells, cardiac cells, and/or cardiomyocytes can also be embedded in a support matrix. A composition that includes a population of reprogrammed cells can also include or be accompanied by one or more other ingredients that facilitate engraftment or functional mobilization of the reprogrammed cells. Suitable ingredients include matrix proteins that support or promote adhesion of the reprogrammed cells, or complementary cell types, such as cardiac pacemaker cells, or cardiac cells at different stages of maturation. In another embodiment, the composition may include physiologically acceptable matrix scaffolds. Such physiologically acceptable matrix scaffolds can be resorbable and/or biodegradable.

The population of reprogrammed cells generated by the methods described herein can include low percentages of non-cardiac cells (e.g., fibroblasts). For example, a population of reprogrammed cells for use in compositions and for administration to subjects can have less than about 90% non-cardiac cells, less than about 85% non-cardiac cells, less than about 80% non-cardiac cells, less than about 75% non-cardiac cells, less than about 70% non-cardiac cells, less than about 65% non-cardiac cells, less than about 60% non-cardiac cells, less than about 55% non-cardiac cells, less than about 50% non-cardiac cells, less than about 45% non-cardiac cells, less than about 40% non-cardiac cells, less than about 35% non-cardiac cells, less than about 30% non-cardiac cells, less than about 25% non-cardiac cells, less than about 20% non-cardiac cells, less than about 15% non-cardiac cells, less than about 12% non-cardiac cells, less than about 10% non-cardiac cells, less than about 8% non-cardiac cells, less than about 6% non-cardiac cells, less than about 5% non-cardiac cells, less than about 4% non-cardiac cells, less than about 3% non-cardiac cells, less than about 2% non-cardiac cells, or less than about 1% non-cardiac cells of the total cells in the cell population.

Many cell types are capable of migrating to an appropriate site for regeneration and differentiation within a subject. To determine the suitability of various therapeutic administration regimens and dosages of cell compositions, the cells can first be tested in a suitable animal model. At one level, cells are assessed for their ability to survive and maintain their phenotype in vivo. Cells can also be assessed to ascertain whether they migrate to diseased or injured sites in vivo, or to determine an appropriate number, or dosage, of cells to be administered. Cell compositions can be administered to immunodeficient animals (such as nude mice, or animals rendered immunodeficient chemically or by irradiation). Tissues can be harvested after a period of regrowth, and assessed as to whether the administered cells or progeny thereof are still present, are alive, and/or have migrated to desired or undesired locations.

Injected cells can be traced by a variety of methods. For example, cells containing or expressing a detectable label (such as green fluorescent protein, or beta-galactosidase) can readily be detected. The cells can be pre-labeled, for example, with BrdU or [$^3$H]-thymidine, or by introduction of an expression cassette that can express green fluorescent protein, or beta-galactosidase. Alternatively, the reprogrammed cells can be detected by their expression of a cell marker that is not expressed by the animal employed for testing (for example, a human-specific antigen when injecting cells into an experimental animal). The presence and phenotype of the administered population of reprogrammed cells can be assessed by fluorescence microscopy (e.g., for green fluorescent protein, or beta-galactosidase), by immunohistochemistry (e.g., using an antibody against a human antigen), by ELISA (using an antibody against a human antigen), or by RT-PCR analysis using primers and hybridization conditions that cause amplification to be specific for RNA indicative of a cardiac phenotype.

Reprogrammed cells can be included in the compositions in varying amounts depending upon the disease or injury to be treated. For example, the compositions can be prepared in liquid form for local or systemic administration containing about $10^3$ to about $10^{12}$ reprogrammed cells, or about $10^4$ to about $10^{10}$ reprogrammed cells, or about $10^5$ to about $10^8$ reprogrammed cells.

One or more of the following types of compounds can also be present in the composition with the cells: a WNT agonist, a GSK3 inhibitor, a TGF-beta signaling inhibitor, an epigenetic modifier, LSD1 inhibitor, an adenylyl cyclase agonist, or any combination thereof. Any of the compounds described herein can be administered with the cells.

The compounds described herein can also be administered to a subject independently of the reprogrammed cell(s). Such a composition may be in a single dose, in multiple doses, in a continuous or intermittent manner, depending, for example, upon the recipient's physiological condition, whether the purpose of the administration is in response to traumatic injury or for more sustained therapeutic purposes, and other factors known to skilled practitioners. The administration of the compounds and compositions of the invention may be essentially continuous over a preselected period of time or may be in a series of spaced doses. Both local and systemic administration is contemplated.

To prepare the composition, the compounds are synthesized and/or the cells are generated, and the components are purified as necessary or desired. The compounds, cells, and/or other agents can be suspended in a pharmaceutically acceptable carrier. If the composition contains only compounds, without cells, the composition can be lyophilized. These compounds and cells can be adjusted to an appropriate concentration, and optionally combined with other agents. The absolute weight of a given compound and/or other agent included in a unit dose can vary widely. The dose and the number of administrations can be optimized by those skilled in the art.

For example, about 0.01 to about 2 g, or about 0.1 to about 500 mg, of at least one compound can be administered. Alternatively, the unit dosage can vary from about 0.01 g to about 50 g, from about 0.01 g to about 35 g, from about 0.1 g to about 25 g, from about 0.5 g to about 12 g, from about 0.5 g to about 8 g, from about 0.5 g to about 4 g, or from about 0.5 g to about 2 g.

Daily doses of the compounds can vary as well. Such daily doses can range, for example, from about 0.1 g/day to about 50 g/day, from about 0.1 g/day to about 25 g/day, from about 0.1 g/day to about 12 g/day, from about 0.5 g/day to about 8 g/day, from about 0.5 g/day to about 4 g/day, and from about 0.5 g/day to about 2 g/day.

It will be appreciated that the amount of compounds and cells for use in treatment will vary not only with the particular carrier selected but also with the route of administration, the nature of the condition being treated and the age and condition of the patient. Ultimately, the attendant health care provider may determine proper dosage. A pharmaceutical composition may be formulated with the appropriate ratio of each compound in a single unit dosage form for administration with or without cells. Cells can be separately provided and either mixed with a liquid solution of the compound composition, or administered separately.

The compounds can also be formulated for sustained release (for example, using microencapsulation, see WO 94/07529, and/or U.S. Pat. No. 4,962,091). The formulations may, where appropriate, be conveniently presented in discrete unit dosage forms and may be prepared by any of the methods well known to the pharmaceutical arts. Such methods may include the step of mixing the therapeutic agent with liquid carriers, solid matrices, semi-solid carriers, finely divided solid carriers or combinations thereof, and then, if necessary, introducing or shaping the product into the desired delivery system.

One or more suitable unit dosage forms containing the compounds and/or the reprogrammed cells can be administered by a variety of routes including parenteral (including subcutaneous, intravenous, intramuscular and intraperitoneal), intracranial, intraspinal, oral, rectal, dermal, transdermal, intrathoracic, intrapulmonary and intranasal (respiratory) routes.

The compositions of the invention may be prepared in many forms that include aqueous solutions, suspensions, tablets, hard or soft gelatin capsules, and liposomes and other slow-release formulations, such as shaped polymeric gels. However, administration of cells often involves parenteral or local administration in an aqueous solution. Similarly, compositions containing cells and/or compounds can be administered in a device, scaffold, or as a sustained release formulation.

Thus while compositions containing only compounds can be administered in an oral dosage form, compositions containing cells are administered locally or systemically as non-oral formulations. When compositions contain only compounds, those compositions can be formulated as oral dosage forms so that the compounds are released into the stomach for quick absorption or in the intestine after passing through the stomach. Different types of formulating procedures are described in U.S. Pat. No. 6,306,434 and in the references contained therein.

Liquid pharmaceutical compositions may be in the form of, for example, aqueous or oily suspensions, solutions, emulsions, syrups or elixirs, dry powders for reconstitution with water or other suitable vehicles before use. Such liquid pharmaceutical compositions may contain conventional additives such as suspending agents, emulsifying agents, non-aqueous vehicles (which may include edible oils), or preservatives.

Compounds and/or cells can be formulated for parenteral administration (e.g., by injection, for example, bolus injection or continuous infusion) and may be presented in unit dosage form in ampoules, prefilled syringes, small volume infusion containers or multi-dose containers with an added preservative. The pharmaceutical compositions can take the form of suspensions, solutions, or emulsions in oily or aqueous vehicles, and can contain formulatory agents such as suspending, stabilizing and/or dispersing agents. Suitable carriers include saline solution, phosphate buffered saline, and other materials commonly used in the art.

The compositions can also contain other ingredients such as agents useful for treatment of cardiac diseases, conditions and injuries, such as, for example, an anticoagulant (e.g., dalteparin (fragmin), danaparoid (orgaran), enoxaparin (lovenox), heparin, tinzaparin (innohep), and/or warfarin (coumadin)), an antiplatelet agent (e.g., aspirin, ticlopidine, clopidogrel, or dipyridamole), an angiotensin-converting enzyme inhibitor (e.g., Benazepril (Lotensin), Captopril (Capoten), Enalapril (Vasotec), Fosinopril (Monopril), Lisinopril (Prinivil, Zestril), Moexipril (Univasc), Perindopril (Aceon), Quinapril (Accupril), Ramipril (Altace), and/or Trandolapril (Mavik)), angiotensin II receptor blockers (e.g., Candesartan (Atacand), Eprosartan (Teveten), Irbesartan (Avapro), Losartan (Cozaar), Telmisartan (Micardis), and/or Valsartan (Diovan)), a beta blocker (e.g., Acebutolol (Sectral), Atenolol (Tenormin), Betaxolol (Kerlone), Bisoprolol/ hydrochlorothiazide (Ziac), Bisoprolol (Zebeta), Carteolol (Cartrol), Metoprolol (Lopressor, Toprol XL), Nadolol (Corgard), Propranolol (Inderal), Sotalol (Betapace), and/or Timolol (Blocadren)), Calcium Channel Blockers (e.g., Amlodipine (Norvasc, Lotrel), Bepridil (Vascor), Diltiazem (Cardizem, Tiazac), Felodipine (Plendil), Nifedipine (Adalat, Procardia), Nimodipine (Nimotop), Nisoldipine (Sular), Verapamil (Calan, Isoptin, Verelan), diuretics (e.g, Amiloride (Midamor), Bumetanide (Bumex), Chlorothiazide (Diuril), Chlorthalidone (Hygroton), Furosemide (Lasix), Hydro-chlorothiazide (Esidrix, Hydrodiuril), Indapamide (Lozol) and/or Spironolactone (Aldactone)), vasodilators (e.g., Isosorbide dinitrate (Isordil), Nesiritide (Natrecor), Hydralazine (Apresoline), Nitrates and/or Minoxidil), statins, nicotinic acid, gemfibrozil, clofibrate, Digoxin, Digitoxin, Lanoxin, or any combination thereof.

Additional agents can also be included such as antibacterial agents, antimicrobial agents, anti-viral agents, biological response modifiers, growth factors; immune modulators, monoclonal antibodies and/or preservatives. The compositions of the invention may also be used in conjunction with other forms of therapy.

Culture Media

Cell culture media are also described herein that can include at least one WNT agonist, a GSK3 inhibitor, a TGF-beta inhibitor, epigenetic modifier, adenylyl cyclase agonists, or any combination thereof. The cell culture medium can also include an exogenous Oct polypeptide. In addition, the cell culture medium can include one or more mammalian cells that are undergoing reprogramming, or that have been reprogrammed.

As described above, the term "media" or "cell culture medium" (also referred to herein as a "medium" or a "culture medium") as referred to herein is a medium for culturing cells containing nutrients that maintain cell viability and support proliferation. The cell culture medium can contain any of the following or in an appropriate combination: salt(s), buffer(s), amino acids, glucose or other sugar(s), antibiotics, serum or serum replacement, combinations thereof, and other components such as peptide growth factors, etc. Cell culture media ordinarily used for particular cell types are available to those skilled in the art.

Examples cell culture media that can be employed include mTESR-1® medium (StemCell Technologies, Inc., Vancouver, Calif.), or Essential 8® medium (Life Technologies, Inc.) on a Matrigel substrate (BD Biosciences, NJ) or on a Corning® Synthemax surface, or in Johansson and Wiles CDM supplemented with insulin, transferrin, lipids and polyvinyl alcohol (PVA) as substitute for Bovine Serum Albumin (BSA). Examples of commercially available media also include, but are not limited to, Dulbecco's Modified Eagle's Medium (DMEM), Minimal Essential Medium (MEM), Basal Medium Eagle (BME), RPM1 1640, Ham's F-10, Ham's F-12, a-Minimal Essential Medium (aMEM), Glasgow's Minimal Essential Medium (G-MEM), Iscove's Modified Dulbecco's Medium, or a general purpose media modified for use with pluripotent cells, such as X-VIVO (Lonza) or a hematopoietic base media.

The amounts of WNT agonists, GSK3 inhibitors, TGF-beta inhibitors, epigenetic modifiers, adenylyl cyclase agonists, and/or combinations thereof in the medium are in a range sufficient to induce mammalian non-pluripotent, non-cardiac cells to cross differentiation boundaries into the cardiac cell lineage.

For example, the compositions and/or culture media can contain any of the agent(s) or compound(s) described herein in an amount sufficient to induce a cell to express cardiac or cardiomyocyte cell markers. Such cardiac or cardiomyocyte cell markers can include any of the following markers: α-Actinin, MLC2v, MY20, cMHC, NKX2-5, MEF2c, GATA4, ISL1, cTNT, cTNI, MLC2a and any combination thereof. For example, the culture media can include can include a TGF-β inhibitor such as SB431542 (e.g., at about 0.1-10 µM), a WNT signaling activator such as CHIR99021 (e.g., at about 3-20 µM), an LSD1/KDM1 inhibitor such as parnate (e.g., at about 0.1-10 µM), and an adenylyl cyclase activator such as forskolin (e.g., at about 3-20 µM).

Incubation can proceed in any of the compositions described herein, for example, until early stage cardiac progenitor markers are expressed by the starting cells. Such early stage cardiac progenitor markers include GATA4, ISL1 or a combination thereof. The early stage cardiac progenitor markers such as GATA4 and/or ISL1 can be expressed by about 6 days, or by about 8 days, or by about 9 days, or by about 10 days, or by about 11 days, or by about 12 days of incubation of cells using the compositions and methods described herein.

The culture media can contain any of the agent(s) or compound(s) described herein in an amount sufficient to reprogram at least 0.001%, or about 0.005%, or about 0.01%, or about 0.02%, or about 0.03% of the cells in a population of cells into a cardiac cell type.

Cells in the culture media can express an Oct polypeptide, particularly during reprogramming. For example, the cells in the culture medium can transiently express the Oct polypeptide. Cells selected for reprogramming do not require expression of heterologous K1f, Sox2, or Myc, and may not be in contact with a K1f, Myc or Sox2 polypeptide. In some embodiments, the expression of other transcription factors such as Myc, Sox2, K1f4 may not be directly or indirectly induced by the culture media.

Similarly, cells in the culture media do not express markers of pluripotency such as Nanog and Rex1 during reprogramming.

However, in other embodiments, the cell culture medium can induce expression of endogenous K1f4 polypeptides, Myc polypeptides, Sox2 polypeptides or a combination thereof. For example, expression of endogenous K1f4 polypeptides, Myc polypeptides, and/or Sox2 polypeptides can occur upon exposure to a composition described herein, even when no exogenous Klf4, Myc, and/or Sox2 nucleic acids have been introduced.

The cells in the media can be human or non-human (e.g., primate, rat, mouse, rabbit, bovine, dog, cat, pig, etc.). Cells that can be reprogrammed include, but are not limited to, epidermal cells, keratinocyte cells, hair follicle cells, HUVAC, cord blood cells, neural progenitor cells and fibroblasts.

Supplementary factors can be included in the compositions and/or in a cell culture media containing any of the cells, compositions, compounds or agents described herein. Examples of such supplementary factors include bone morphogenic protein (BMP)-1, bone morphogenic protein-2, bone morphogenic protein-3, bone morphogenic protein-4, bone morphogenic protein-5, bone morphogenic protein-6, bone morphogenic protein-7, bone morphogenic protein-8, bone morphogenic protein-9, bone morphogenic protein-10, bone morphogenic protein-11, bone morphogenic protein-12, bone morphogenic protein-13, bone morphogenic protein-14, bone morphogenic protein-15, brain derived neurotrophic factor, ciliary neurotrophic factor, cytokine-induced neutrophil chemotactic factor 1, cytokine-induced neutrophil chemotactic factor 2α, cytokine-induced neutrophil chemotactic factor 2β, β endothelial cell growth factor, endothelin 1, epidermal growth factor, epithelial-derived neutrophil attractant, fibroblast growth factor (FGF) 4, fibroblast growth factor 5, fibroblast growth factor 6, fibroblast growth factor 7, fibroblast growth factor 8, fibroblast growth factor 8b, fibroblast growth factor 8c, fibroblast growth factor 9, fibroblast growth factor 10, fibroblast growth factor (acidic), fibroblast growth factor (basic), growth related protein, growth related protein α, growth related protein β, growth related protein γ, heparin binding epidermal growth factor, hepatocyte growth factor, insulin-like growth factor I, insulin-like growth factor II, insulin-like growth factor binding protein, keratinocyte growth factor, leukemia inhibitory factor, neurotrophin-3, neurotrophin-4, placenta growth factor, placenta growth factor 2, platelet-derived endothelial cell growth factor, platelet derived growth factor, platelet derived growth factor A chain, platelet derived growth factor AA, platelet derived growth factor AB, platelet derived growth factor B chain, platelet derived growth factor BB, pre-B cell growth stimulating factor, stem cell factor, transforming growth factor a, transforming growth factor β, transforming growth factor β1, transforming growth factor 01.2, transforming growth factor 132, transforming growth factor β3, latent transforming growth factor β1, transforming growth factor β binding protein I, transforming growth factor β binding protein II, transforming growth factor β binding protein III, and vascular endothelial growth factor.

Exemplary cytokines can be included such as interleukin (IL)-1, IL-2, IL-3, IL-4, IL-5, IL-6, IL-7, IL-8, IL-9, IL-10, IL-11, IL-12, IL-13, IL-14, IL-15, IL-16, IL-17, IL-18, interferon (IFN), IFN-γ, tumor necrosis factor (TNF), TNF1, TNF2, TNF-α, macrophage colony stimulating factor (M-CSF), granulocyte-monocyte colony stimulating factor (GM-CSF), granulocyte colony stimulating factor (G-CSF), megakaryocyte colony stimulating factor (Meg-CSF)-thrombopoietin, stem cell factor, and erythropoietin. Chemokines can also be included such as IP-10 and Stromal Cell-Derived Factor 1α.

Exemplary hormones contemplated for inclusion in the compositions and/or cell culture media described herein can include, but are not limited to, steroid hormones and peptide hormones, such as insulin, somatostatin, growth hormone, hydrocortisone, dexamethasone, 3,3',5-Triiodo-L-thyronine, and L-Thyroxine.

Kits

A variety of kits are described herein that include any of the compositions, compounds and/or agents described herein. The kit can include, for example, a culture media in concentrated or non-concentrated form. The kit can include any of compounds described herein, either mixed together or individually packaged, and in dry or hydrated form. The compounds and/or agents described herein can be packaged separately into discrete vials, bottles or other containers. Alternatively, any of the compounds and/or agents described herein can be packaged together as a single composition, or as two or more compositions that can be used together or separately. The compounds and/or agents described herein can be packaged in appropriate ratios and/or amounts to facilitate conversion of selected cells across differentiation boundaries to form cardiac progenitor cells and/or cardiomyocytes.

The kit can also include an expression cassette, an expression vector, or a combination thereof that includes a segment encoding an Oct polypeptide operably linked to a promoter and other optional regulatory elements. The expression cassette or vector can be provided in dehydrated form or in a ready to use solution.

A kit is described herein for culture of cells in vitro that can include any of the compositions, compounds, expression cassettes, expression vectors, and/or agents described herein, as well as instructions for using those compositions, compounds, expression cassettes, expression vectors, and/or agents.

Some kits can include a cell culture or cell media that includes any of the compositions, compounds and/or agents described herein. The kits can include one or more sterile cell collection devices such as a swab, skin scrapping device, a needle, a syringe, and/or a scalpel. The kits can also include antibodies for detection of cardiac progenitor and/or cardiomyocyte cell markers such as antibodies against any of the following markers: α-Actinin, MLC2v, MY20, cMHC, NKX2-5, GATA4, ISL1, NKX2-5, MEF2c, cTNT, cTNI, MLC2a, and any combination thereof. The antibodies can be labeled so that a detectable signal can be observed when the antibodies form a complex with the cardiac progenitor cell and/or cardiomyocytes cell marker(s).

The instructions can include guidance for introducing a nucleic acid into selected cells (e.g., a selected starting cell or selected cells). Such a nucleic acid can be an RNA, an expression cassette, or an expression vector that encodes an Oct polypeptide or a miR-302, and culturing the cells for a time and under conditions sufficient to express the Oct polypeptide and/or the miR-302. The instructions can also include instructions for converting the cells across differentiation boundaries and into the cardiac lineage using any of the compositions and methods disclosed herein. For example, the instructions can describe amounts of the compositions, compounds and/or agents described herein to add to cell culture media, times sufficient to convert cells to the cardiac lineage, maintenance of appropriate cell densities for optimal conversion, and the like. For example, the instructions can describe procedures for rehydration or dilution of the compositions, compounds and/or agents described herein. When a kit provides a cell culture medium containing some of the compositions, compounds and/or agents described herein, the instructions can describe how to add other compounds and/agents. The instructions can also describe how to convert the selected cells to cardiac progenitor cells or to cardiomyocytes.

The instructions can also describe procedures for detecting cardiac progenitor and/or cardiomyocyte cell markers by use of antibodies against those markers so that the extent of conversion and/or differentiation can be assessed.

Another kit is also described herein that includes any of the compositions, compounds and/or agents described herein for therapeutic treatment of a subject. The kit can include any of the compositions, compounds and/or agents described herein, as well as instructions for administering those compositions, compounds and/or agents. Such instructions can provide the information described throughout this application.

The kit can also include cells. For example, the kit can include chemically induced cardiac progenitor cells and/or cardiomyocytes that have been treated by the compositions and/or methods described herein and that are ready for administration.

The cells, compositions and/or compounds can be provided within any of the kits in the form of a delivery device. Alternatively a delivery device can be separately included in the kit(s), and the instructions can describe how to assemble the delivery device prior to administration to a subject. The delivery device can provide a scaffold for cell growth and/or a matrix for controlled release of any of the compositions, compounds or agents described herein.

Any of the kits can also include syringes, catheters, scalpels, sterile containers for sample or cell collection, diluents, pharmaceutically acceptable carriers, and the like.

The kits can provide other factors such as any of the supplementary factors or drugs described herein for the compositions in the preceding section or other parts of the application.

Definitions

Cardiomyocytes or cardiac myocytes are the muscle cells that make up the cardiac muscle. Each myocardial cell contains myofibrils, which are long chains of sarcomeres, the contractile units of muscle cells. Cardiomyocytes show striations similar to those on skeletal muscle cells, but unlike multinucleated skeletal cells, they contain only one nucleus. Cardiomyocytes have a high mitochondrial density, which allows them to produce ATP quickly, making them highly resistant to fatigue. Mature cardiomyocytes can express one or more of the following cardiac markers: α-Actinin, MLC2v, MY20, cMHC, NKX2-5, GATA4, cTNT, cTNI, MEF2c, MLC2a, or any combination thereof. In some embodiments, the mature cardiomyocytes express NKX2-5, MEF2c or a combination thereof. Cardiac progenitor cells express early stage cardiac progenitor markers such as GATA4, ISL1 or a combination thereof.

As used herein, the term "functional cardiomyocyte" refers to a differentiated cardiomyocyte that is able to send or receive electrical signals. In some embodiments, a cardiomyocyte is said to be a functional cardiomyocyte if it exhibits electrophysiological properties such as action potentials and/or $Ca^{2+}$ transients.

As used herein, a "differentiated non-cardiac cell" can refer to a cell that is not able to differentiate into all cell types of an adult organism (i.e., is not a pluripotent cell), and which is of a cellular lineage other than a cardiac lineage (e.g., a neuronal lineage or a connective tissue lineage). Differentiated cells include, but are not limited to, multipotent cells, oligopotent cells, unipotent cells, progenitor cells, and terminally differentiated cells. In particular embodiments, a less potent cell is considered "differentiated" in reference to a more potent cell.

As used herein, a cell that differentiates into a mesodermal, ectodermal or endodermal lineage defines a cell that becomes committed to a specific mesodermal, ectodermal or endodermal lineage, respectively. Examples of cells that differentiate into a mesodermal lineage or give rise to specific mesodermal cells include, but are not limited to, cells that are adipogenic, chondrogenic, cardiogenic, dermatogenic, hematopoietic, hemangiogenic, myogenic, nephrogenic, urogenitogenic, osteogenic, pericardiogenic, or stromal. Examples of cells that differentiate into ectodermal lineage include, but are not limited to, epidermal cells, neurogenic cells, and neurogliagenic cells. Examples of cells that differentiate into endodermal lineage include, but are not limited to, pleurigenic cells, and hepatogenic cells, cells that give rise to the lining of the intestine, and cells that give rise to pancreogenic and splanchogenic cells.

A "somatic cell" is a cell forming the body of an organism. Somatic cells include cells making up organs, skin, blood, bones and connective tissue in an organism, but not germ cells.

Cells can be from, e.g., human or non-human mammals. Exemplary non-human mammals include, but are not limited to, mice, rats, cats, dogs, rabbits, guinea pigs, hamsters, sheep, pigs, horses, bovines, and non-human primates. In some embodiments, a cell is from an adult human or non-human mammal. In some embodiments, a cell is from a neonatal human, an adult human, or non-human mammal.

As used herein, the term "totipotent" means the ability of a cell to form all cell lineages of an organism. For example, in mammals, only the zygote and the first cleavage stage blastomeres are totipotent.

As used herein, the term "pluripotent" means the ability of a cell to form all lineages of the body or soma (i.e., the embryo proper). For example, embryonic stem cells are a type of pluripotent stem cells that are able to form cells from each of the three germs layers, the ectoderm, the mesoderm, and the endoderm. Pluripotent cells can be recognized by their expression of markers such as Nanog and Rex1.

As used herein, the term "multipotent" refers to the ability of an adult stem cell to form multiple cell types of one lineage. For example, hematopoietic stem cells are capable of forming all cells of the blood cell lineage, e.g., lymphoid and myeloid cells.

As used herein, the term "oligopotent" refers to the ability of an adult stem cell to differentiate into only a few different cell types. For example, lymphoid or myeloid stem cells are capable of forming cells of either the lymphoid or myeloid lineages, respectively.

As used herein, the term "unipotent" means the ability of a cell to form a single cell type. For example, spermatogonial stem cells are only capable of forming sperm cells.

As used herein, the term "direct reprogramming" or "transdifferentiation" refers to the generation of a cell of a certain lineage (e.g., a cardiac cell) from a different type of cell (e.g., a fibroblast cell) without an intermediate process of de-differentiating the cell into a cell exhibiting pluripotent stem cell characteristics.

As used herein, the terms "subject" or "patient" refers to any animal, such as a domesticated animal, a zoo animal, or a human. The "subject" or "patient" can be a mammal like a dog, cat, horse, livestock, a zoo animal, or a human. The subject or patient can also be any domesticated animal such as a bird, a pet, or a farm animal Specific examples of "subjects" and "patients" include, but are not limited to, individuals with a cardiac disease or disorder, and individuals with cardiac disorder-related characteristics or symptoms.

The following non-limiting Examples illustrate some of the experimental work involved in developing the invention.

EXAMPLE 1

Materials and Methods

This Example describes some of the materials and methods used in the development of the invention.

Lentivirus Production and Infection

Lentivirus encoding Oct4, rtTA and tetO—OKS-RFP were prepared in 293T cells using pSin-EF2-hOCT4 (Addgene #16579), FUW-M2rtTA (Addgene #20342) and pHAGE2-TetO-STEMCCA-redlight described by Kim et al. (*Proc Natl Acad Sci USA* 108: 7838-7843 (2011)); Yu et al. (*Science* 318: 1917-1920 (2007)); Sommer et al. (*Stem Cells* 27: 543-49 (2009)); and Zhu et al. (*Cell Stem Cell* 7: 651-655 (2010)), each of which is specifically incorporated herein by reference in its entirety. Four µg/ml of polybrene was added to the culture medium during virus infection to increase infection efficiency. To ensure reproducibility and minimize inter-experimental variation, lentivirus were generated in large amounts and then aliquoted into vials that were stored at −80° C.

MEF and TTF Preparation

Mouse embryonic fibroblasts (MEFs) and mouse tail tip fibroblasts (TTFs) were prepared from C57B6 mice and OG2 mice (JAX) following the protocol described by Efe et al. (*Nature Cell Biology* 13: 215-U261 (2011)). Briefly, mouse embryonic fibroblasts were isolated from E13.5 mouse embryos. Head, internal organs from the abdominal cavity and heart regions of embryos were carefully removed. The remaining tissues were cut into pieces and trypsinized to produce single-cell suspensions. Those cells were expanded in mouse embryonic fibroblast growth medium (MEF-GM) containing DMEM supplemented with 1% FBS, 2 mM Glutamax and 0.1 mM non-essential amino acids (NEAA).

To generate mouse tail tip fibroblasts, tail tips from neonatal mice were minced well with a sterile razor blade and then divided evenly put into 10 cm culture dishes containing 2 ml of mouse embryonic fibroblast growth medium. Next day, additional medium was added. Five days later, fibroblasts that had migrated out of tissue samples were collected and expanded.

Cardiac Reprogramming

Mouse embryonic fibroblast (MEFs) and mouse tail tip fibroblasts (TTFs) were originally passaged onto gelatin coated tissue culture plates. Lentivirus were incubated with cells for 12 h and then cultured in mouse embryonic fibroblast growth medium (MEF-GM). After 3-5 days recovery, cells were replated onto Matrigel (BD Biosciences) coated plates at 5000 cells per cm². On the next day, infected mouse embryonic fibroblasts were switched to cardiac reprogramming media (CRM) containing knockout DMEM with 5% knockout serum replacement, 15% embryonic stem cell-qualified FBS, 1% Glutamax, 1% nonessential amino acids, and 0.1 mM β-mercaptoethanol, with or without small molecules. For TetO-OKS induced cardiac reprogramming, 2 ug/ml doxycycline (DOX) were also added in cardiac reprogramming media for 6 days and then culture medium was changed into chemically defined media (CDM) containing RPMI-1640 supplemented with 0.5×N2, 1×B27 (without vitamin A), 0.05% bovine serum albumin (BSA) fraction V, 0.5% Glutamax and 0.1 mM β-mercaptoethanol (all components from Invitrogen). Twenty (20) ng/ml of BMP4 (Stemgent) was added to the chemically defined media (CDM) for the first 5 days. For Oct4 induced cardiac reprogramming, cells were re-plated at a ratio of 1:12 at day 8 and kept cultured in cardiac reprogramming media with small molecules until day 15, then switched to chemically defined media and treated with BMP4 for the first 5 days. All the small molecules were tested during culture of cells in cardiac reprogramming media (CRM). The following small molecules were used: 2 µM SB431542, 10 µM CHIR99021, 2 µM parnate, and 10 µM forskolin.

Immunostaining

Cells were fixed in 4% paraformaldehyde for 15 min and permeabilized in 0.5% Triton X-100 for 15 minutes, then incubated in blocking buffer containing 3% BSA for 1 hour at room temperature. Primary antibodies were diluted in blocking buffer and incubated overnight at 4° C. The following antibodies were used in some of the procedures described herein: cardiac troponin T (MS-295-P1, Thermo Scientific; dilution 1:500); Gata4 (sc-25310, Santa Cruz Biotechnology; dilution 1:200); MEF2C (#5030s, Cell signaling; dilution 1:200); cardiac Myosin heavy chain (ab15, Abcam; dilution 1:400); Nkx2-5 (sc-8697, Santa Cruz Biotechnology; dilution 1:200); Mlc2v (ab15, abcam; dilution 1:300); Mlc2a (#311011, synaptic systems; dilution 1:100); Connexin-43 (610061, BD Biosciences; dilution 1:100) and α-Actinin (A8711, Sigma-Aldrich; dilution 1:200). Following extensive PBS washes (total 1 hr), cells were incubated with the appropriate Alexa Fluor-conjugated secondary antibodies (Invitrogen) for 1 hr at room temperature and nuclei were stained with DAPI (4,6-diamidino-2-phenylindole; Sigma-Aldrich). Images were acquired by a Zeiss Axioimager Z1 equipped with an Apotome system and processed using Zeiss Axiovision software.

Gene Expression Analysis by QPCR

Total RNA was extracted from samples at the designated time points using the RNeasy Plus mini kit with QiaShredder (Qiagen). RNA was reverse transcribed using the iScript cDNA synthesis kit (Bio-Rad). Quantitative PCR was performed with iQSYBR Green Supermix on the 7500 Fast Real-Time PCR System (Applied Biosystems). All qPCR reactions were done in triplicate, and the expression data were normalized to GAPDH. The following primers were used in QPCR reaction:

TABLE 1

Primers for Gene Expression Analysis

| Target | Primer | Sequences | SEQ ID NO |
|---|---|---|---|
| Gata4 | F | CCTGGAAGACACCCCAATCTC | 5 |
| Gata4 | R | AGGTAGTGTCCCGTCCCATCT | 6 |
| Nkx2-5 | F | GGTCTCAATGCCTATGGCTAC | 7 |
| Nkx2-5 | R | GCCAAAGTTCACGAAGTTGCT | 8 |
| Mef2C | F | AGATACCCACAACACACCACGCGCC | 9 |
| Mef2C | R | CATTATCCTTCAGAGAGTCGCATGCGCTT | 10 |
| Ryr2 | F | ACATCATGTTTTACCGCCTGAG | 11 |
| Ryr2 | R | TTTGTGGTTATTGAACTCTGGCT | 12 |
| Myh6 | F | GATGCCCAGATGGCTGACTT | 13 |
| Myh6 | R | GGTCAGCATGGCCATGTCCT | 14 |
| Tnnt2 | F | GCGGAAGAGTGGGAAGAGACA | 15 |

TABLE 1-continued

Primers for Gene Expression Analysis

| Target | Primer | Sequences | SEQ ID NO |
|---|---|---|---|
| Tnnt2 | R | CCACAGCTCCTTGGCCTTCT | 16 |
| Nanog | F | TCTTCCTGGTCCCCACAGTTT | 17 |
| Nanog | R | GCAAGAATAGTTCTCGGGATGAA | 18 |
| Rex1 | F | CCCTCGACAGACTGACCCTAA | 19 |
| Rex1 | R | TCGGGGCTAATCTCACTTTCAT | 20 |
| Gapdh | F | GTGGCAAAGTGGAGATTGTTG | 21 |
| Gapdh | R | CTCCTGGAAGATGGTGATGG | 22 |

Electrophysiology

Big beating clusters were first dispersed by 0.2% collagenase II for 25 minutes, then trypsinized for 2 minutes and replated onto matrigel-coated coverslips in chemically defined media. Two days later, the coverslips were transferred to a superfusion bath (Warner RC-26GLP) on a Nikon TiS inverted microscope equipped with a dual wavelength microfluorometer (IonOptix, Milton, Mass.). Superfusion solutions were warmed to 30° C. using the superfusion system (Valvelink, AutoMate Scientific, Berkeley, Calif.). Spontaneously beating cells were selected for study, with one cell being patch-clamped. An Axopatch 200B amplifier (Molecular Devices Inc., Sunnyvale, Calif.) was coupled via pClamp software (v10) to patch electrodes of 2-5 MegOhms (1B-150F; WPI, Sarasota, Fla.) filled with intracellular solution containing 120 mM KCl, 20 mM NaHEPES, 10 mM MgATP, 0.1 m M $K_2$EGTA, 2 mM $MgCl_2$, set to pH 7.1 with KOH. Myocyte clusters were perfused at constant flow (W2-64, Warner Instruments, Hamden Conn.) with modified Tyrode's extracellular solution containing 137 mM NaCl, 10 mM NaHEPES, 10 mM dextrose, 5 mM KCl, 2 mM $CaCl_2$, 1 mM $MgCl_2$, set to pH 7.4 using NaOH.

Intracellular Calcium ($Ca^{++}$) Measurements

Myocytes were loaded with 5 μM Fluo-4 AM (Molecular Probes, Invitrogen Corp, Carlsbad, Calif.), a $Ca^{++}$ indicator dye for 20 minutes at room temperature followed by 20 minutes in dye-free extracellular solution to allow for Fluo-4 de-esterification prior to commencing recordings. $Ca^{++}$ transients were recorded via a standard filter set (#49011 ET, Chroma Technology Corp., Bellows Falls, Vt.) and a photomultiplier-based recording system (IonOptix PMT400, Milton, Mass.). Fluorescence was recorded simultaneously from an entire myocyte cluster. Between sampling periods, excitation light was blocked by a shutter (CS35; Vincent Associates, Rochester, N.Y.) and background fluorescence was recorded after removing the cell(s) from the field of view at the end. Where applicable, 1 μM isoproterenol (Iso) or 25 μM carbachol (Cch) were applied locally (to the cell cluster of interest) using a perfusion pencil (AutoMate Scientific, Berkeley, Calif.).

Electropotential Data Recording and Statistical Analyses

Action potentials were digitized at 5 kHz and low-pass filtered at 2 kHz. Fluorescence transients were digitized at 1 kHz and low-pass filtered at 0.5 kHz. Periods between data files were varied empirically, from essentially gap-free to periodical. The maximum depolarization rate of the action potential upstroke ($V_{max}$) was calculated using Origin Pro 8.6 software (Originlab, Northampton, Mass.) or Clampfit (pClamp 10, Molecular Devices, Sunnydale, Calif.). Action potential amplitude and duration, determined between the upstroke (at Vmax) and 90% repolarization (APD90), were determined using in-house analysis routines implemented in Excel 2007 (Microsoft, Redmond, Wash.) with correction for a −5.6 mV liquid junction potential. To avoid movement artifacts in fluorescence recordings, cells and microclusters were framed to include a cell-free border and bright field images were recorded. All statistical comparisons were performed using two-tailed, paired or unpaired t tests. Mean values are presented with standard errors (mean±SEM).

EXAMPLE 2

Small Molecule Cocktails Enable the Cardiac Conversion of Mouse Fibroblasts in Conjunction with Oct4 Expression To develop small molecule conditions for inducing cardiac reprogramming from mouse fibroblasts following the cell-activation and signaling-directed (CASD) lineage conversion paradigm, a strategy was developed that combines iPSC induction and small molecules that may induce cell activation with cardiogenic small molecules that may serve to direct the cardiomyocyte fate.

To more precisely control exogenous transcription factor expression and minimize variations in screening, a single lentivirus vector was generated for expression of Oct4, K1f4 and Sox2, called pHAGE2-TetO-STEMCCA-redlight ("TetO-OKS"), that is a tetracycline inducible system and that includes Oct4, K1f4, Sox2, and RFP coding regions, each separated by a self-cleaving 2A peptide and an IRES sequence. To carry out the screening, mouse embryonic fibroblasts were infected with TetO-OKS lentivirus and split into 24-well plates. Small molecule combinations and doxycycline (Dox) were added to the cells in cardiac reprogramming medium (CRM) for the first 6 days followed by treatment with BMP4 as shown in FIG. 1A. The number of beating clusters was counted.

Figure 1B:
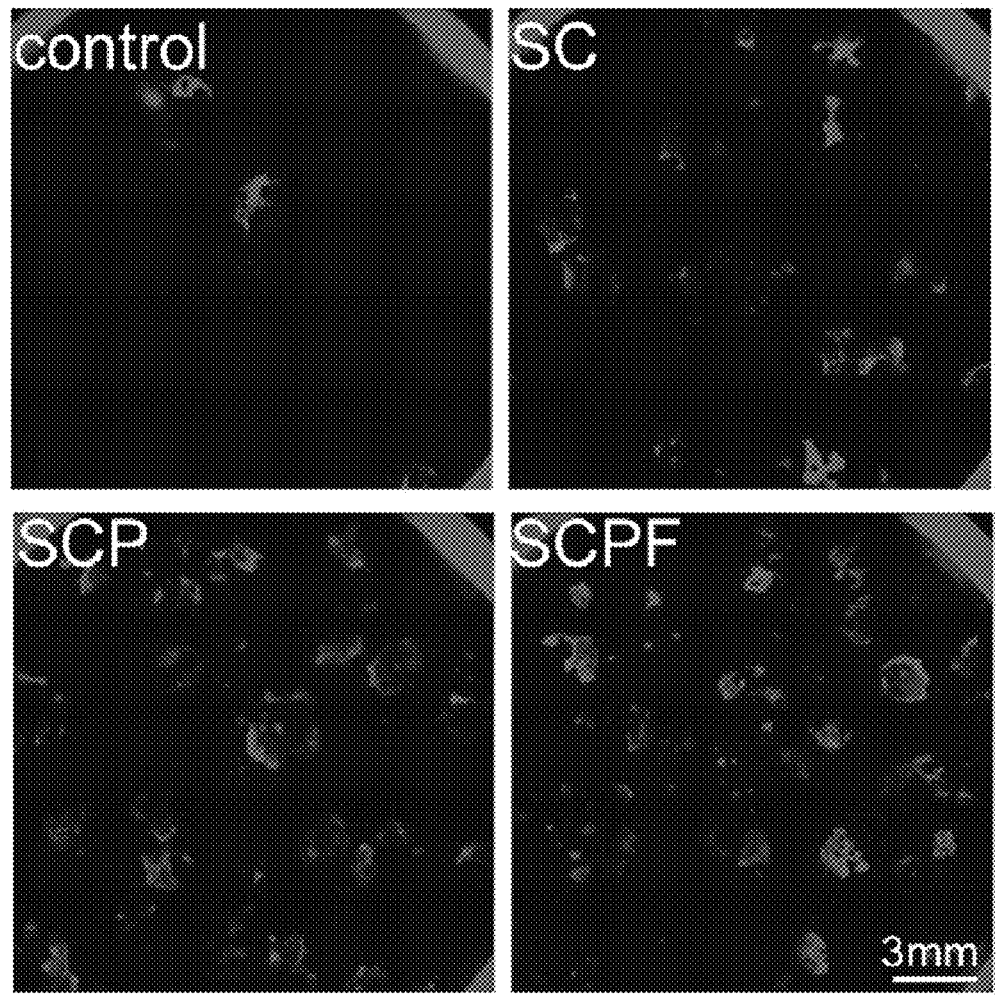
Figure 1C:
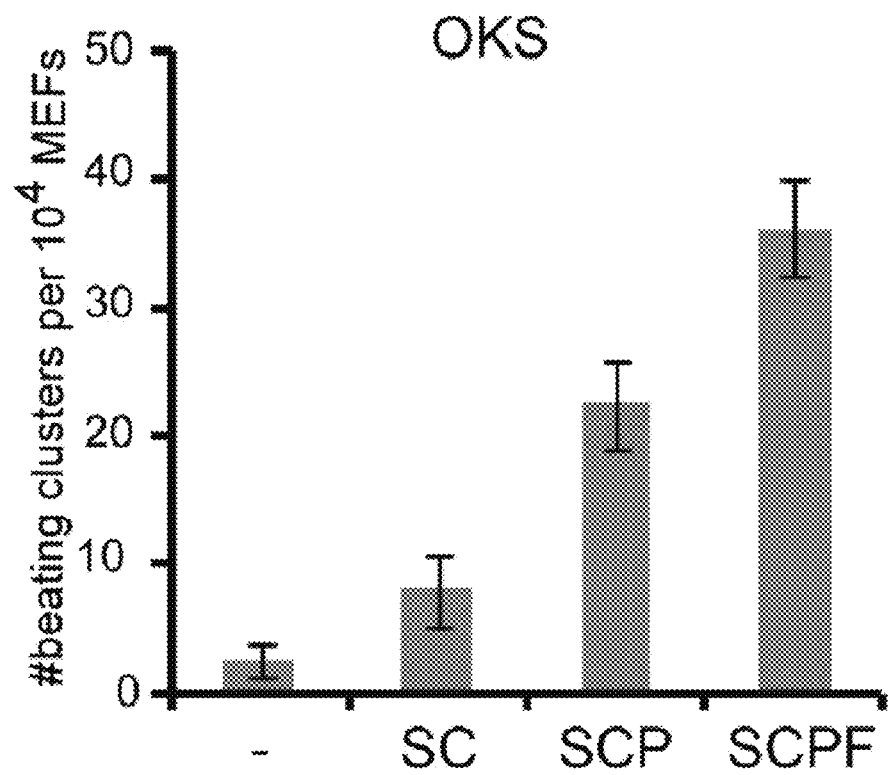

In control wells without any compound treatment, there were few beating clusters. Addition of SB431542 or CHIR99021 could slightly increase the reprogramming efficiency. However, as shown in FIG. 1C, the combination of SB431542 and CHIR99021 could increase the cardiac reprogramming by two fold. Given the seemingly shared role in promoting reprogramming and cardiac induction by WNT signaling activation and TGFβ signaling inhibition, the combination of SB431542 and CHIR99021 (SC) was used as a baseline small molecule condition in conjunction with transcription factors.

Additional iPSC inducing/enhancing and cardiogenic small molecules were then screened using the fibroblasts infected with TetO-OKS lentivirus for induction of mouse fibroblast conversion into cardiomyocyte-like cells. The small molecules tested included modulators of epigenetic enzymes, signaling pathways, metabolism, and transcription from WNT, TGFβ, BMP, and Activin/Nodal signaling pathways.

The addition of parnate (LSD1/KDM 1 inhibitor) and forskolin (adenylyl cyclase activator) to the combination of SB431542 and CHIR99021, further increased the reprogramming efficiency (FIG. 1C). This result was confirmed in a larger well format as shown (FIGS. 1B and 1C). The small molecule combination of SB431542, CHIR99021, parnate, and forskolin is referred to herein as SCPF.

With the significant cardiac induction exhibited in FIG. 1, the inventors then asked whether the SCPF conditions could enable cardiac reprogramming in conjunction with only a single transcription factor. As shown in FIG. 2A, using the process described herein, mouse embryonic fibroblasts infected with Oct4 and treated with SCPF became spontaneously contracting clusters. The first contracting cluster was observed around day 20. At day 30, a total of 99±17 contracting clusters had been generated from the original 10,000 plated MEFs (n=6). In contrast, no colonies were found in control wells without compound treatment or even in the wells with SB431542, CHIR99021, and parnate (SCP) treatment Immunocyto-chemistry analysis confirmed that these beating patches were positive for cardiac specific markers, including cTnT and cardiac MHC (cMHC) (FIG. 2B).

Figure 2C:
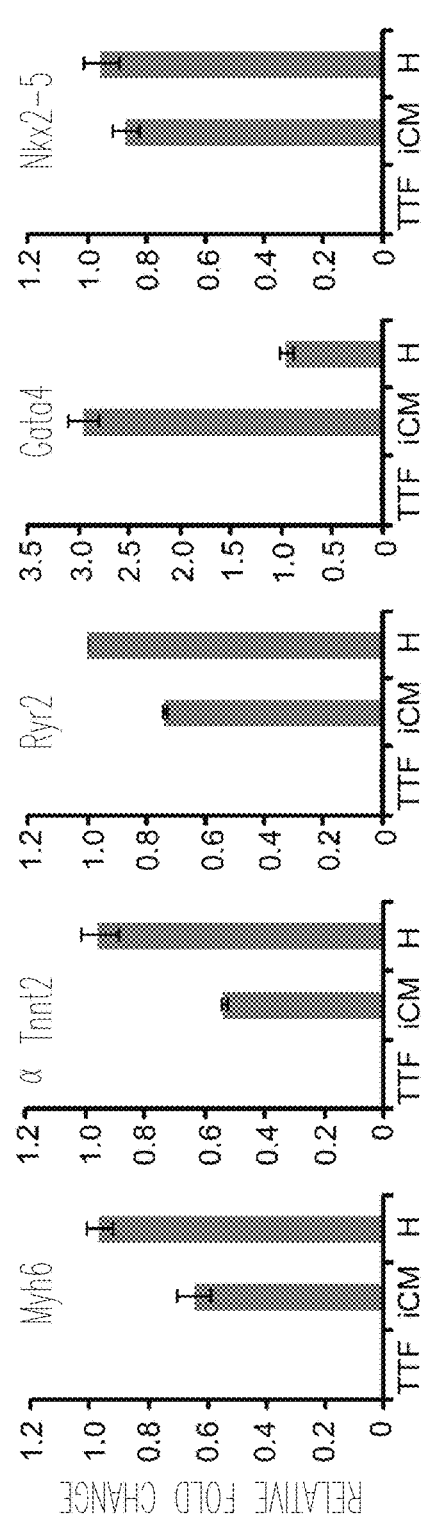

In order to exclude the possibility that beating cells might be generated from any rare cardiac progenitors in mouse embryonic fibroblast cells, mouse tail tip fibroblasts (TTFs) were tested to ascertain whether, in conjunction with Oct4 expression, the SCPF composition could enable cardiac induction from mouse tail tip fibroblasts (TTFs), which are much more homogenous than mouse embryonic fibroblasts and do not contain any cardiac lineage cells. Using the same condition utilized for mouse embryonic fibroblasts (FIG. 2A), nearly 50 spontaneously beating colonies (n=6) were generated from 10,000 TTFs by about day 30. Quantitative RT-PCR (qRT-PCR) showed that cardiac specific genes, including Myh6, Tnnt2, Ryr2, Gata4, and Nkx2-5 were highly expressed in these induced cardiomyocytes when compared with TTFs (FIG. 2C).

Figure 2D:
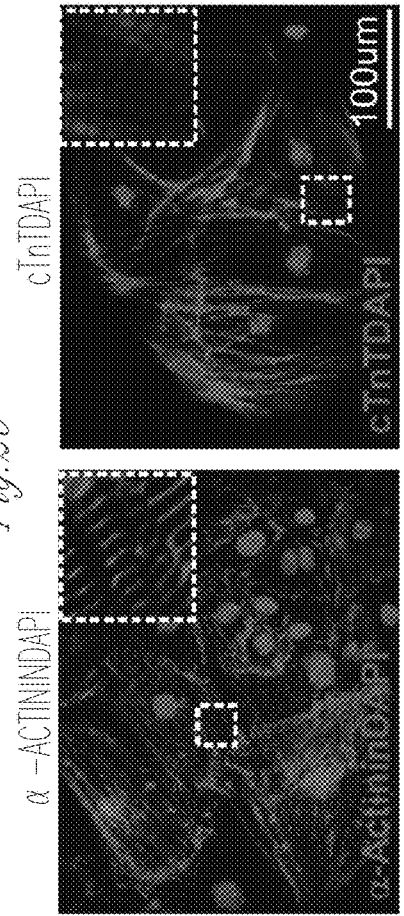

To further characterize these induced beating cells, the large beating patches were digested into small cell clusters or single cells for immunocytochemistry analysis. These induced cardiomyocytes showed triangular or multiangular morphology with cardiac muscle striations characteristic of sarcomeric structures Immunocytochemistry analysis revealed that these cells were positive for typical cardiomyocyte markers including cTnT, α-Actinin and cMHC, and displayed a clear cross-striated pattern (FIG. 2D).

Figure 2E:
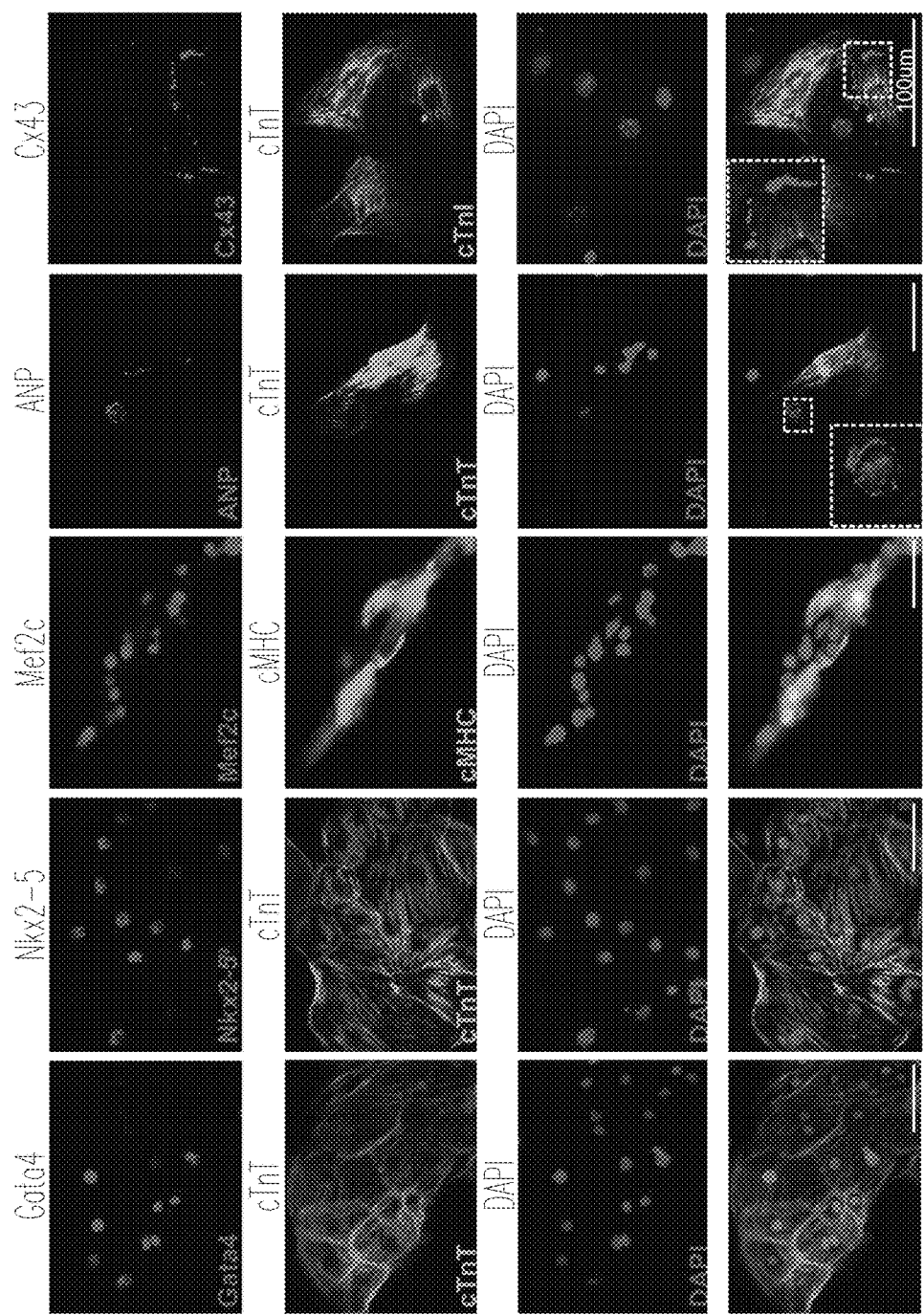

Core transcription factors and peptides for cardiac development and function including Gata4, MEF2C, and Nkx2-5, as well as ANP, were also highly expressed in the induced cardiomyocytes (FIG. 2E). Moreover, Connexin-43 (Cx43), which is a specific gap junction protein in cardiomyocytes, was also detected along the periphery of the induced cardiomyocytes, indicating the development of gap junction proteins involved in cell contact communication (FIG. 2E).

Figure 2F:
Figure 2G:
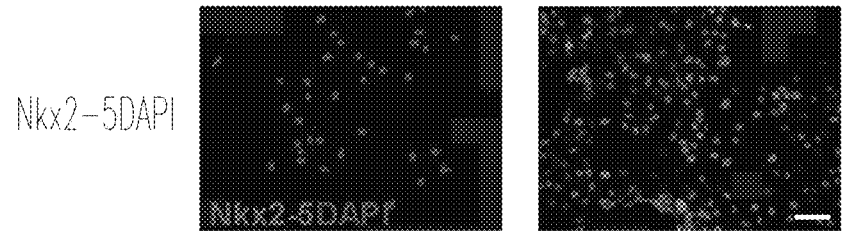
Figure 2G:
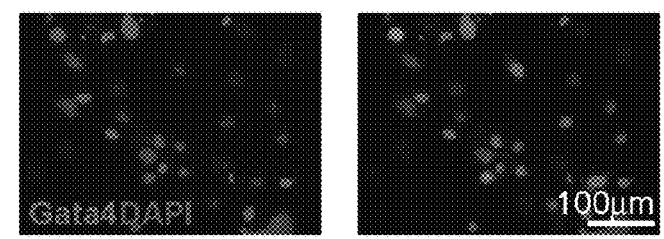
Figure 2H:
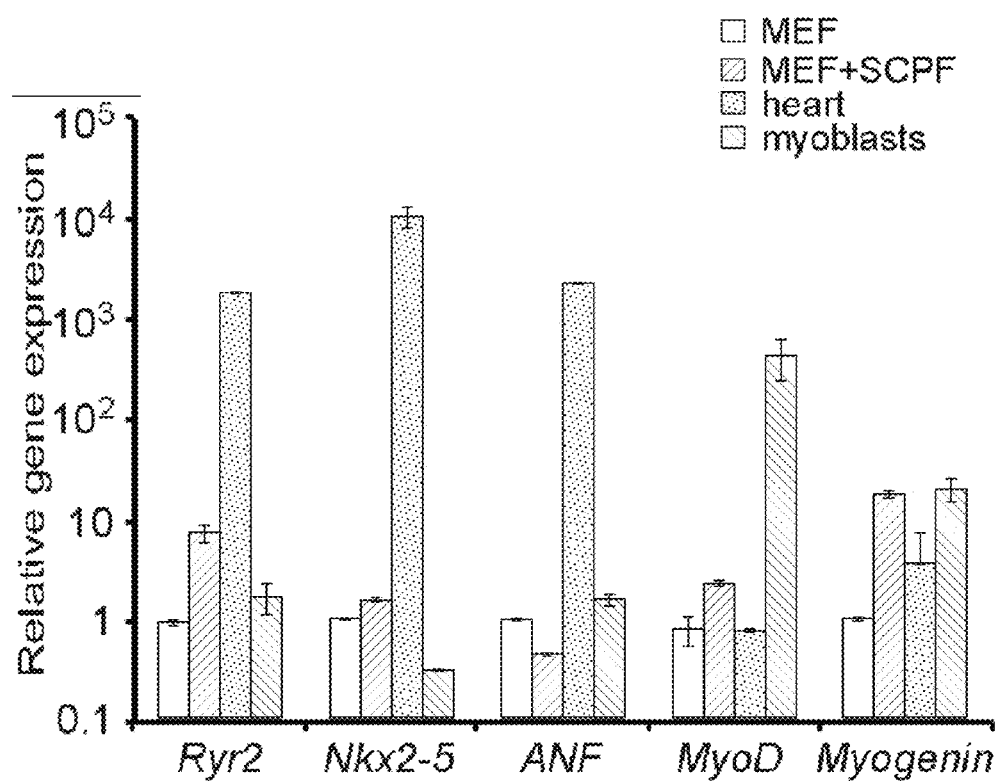

A few twitching/contracting cells were also observed in the control wells treated only with small molecules (e.g., the SCPF composition) without Oct4 transduction. These SCPF-treated cells exhibited a long tube-like morphology that was different from neonatal cardiomyocytes, pluripotent stem cell-derived cardiomyocytes, or these induced cardiomyocytes in the presence of Oct4 characterized above. Interestingly, they were positive for cTnT, cMHC and α-Actinin immunostaining (FIG. 2F). However, further characterizations revealed that those cells lacked expression of core cardiac transcription factors, such as Nkx2-5 and Gata4 (FIG. 2G), while they modestly expressed skeletal muscle transcription factors MyoD and Myogen in (FIG. 2H). This may suggest that those tube-like contracting cells did not represent fully reprogrammed cardiomyocytes or may possess certain skeletal muscle features. Therefore, these cells were not further investigated.

EXAMPLE 3

Pluripotency was not Generated During the Reprogramming of Fibroblasts to Cardiomyocyte-like Cells The cardiac reprogramming conditions described above do not generate induced pluripotency stem cells. Instead, these conditions convert non-cardiomyocytes into cardiomyocytes.

To more carefully examine the reprogramming process, time-lapse imaging analysis was performed of Oct4-GFP reporter mouse embryonic fibroblasts using procedures like those described by (Do and Scholer, Stem Cells (Dayton, Ohio) 22: 941-949 (2004)) while those fibroblasts were undergoing the cardiac reprogramming induced by the SCPF/Oct4 composition/methods described herein. When closely tracking the induction of beating cardiac colonies over the 25 days, the first beating cluster was observed at day 20; immunohisto-chemistry analysis confirmed that those beating clusters were cTnT positive (FIG. 2B).

Figure 3A:
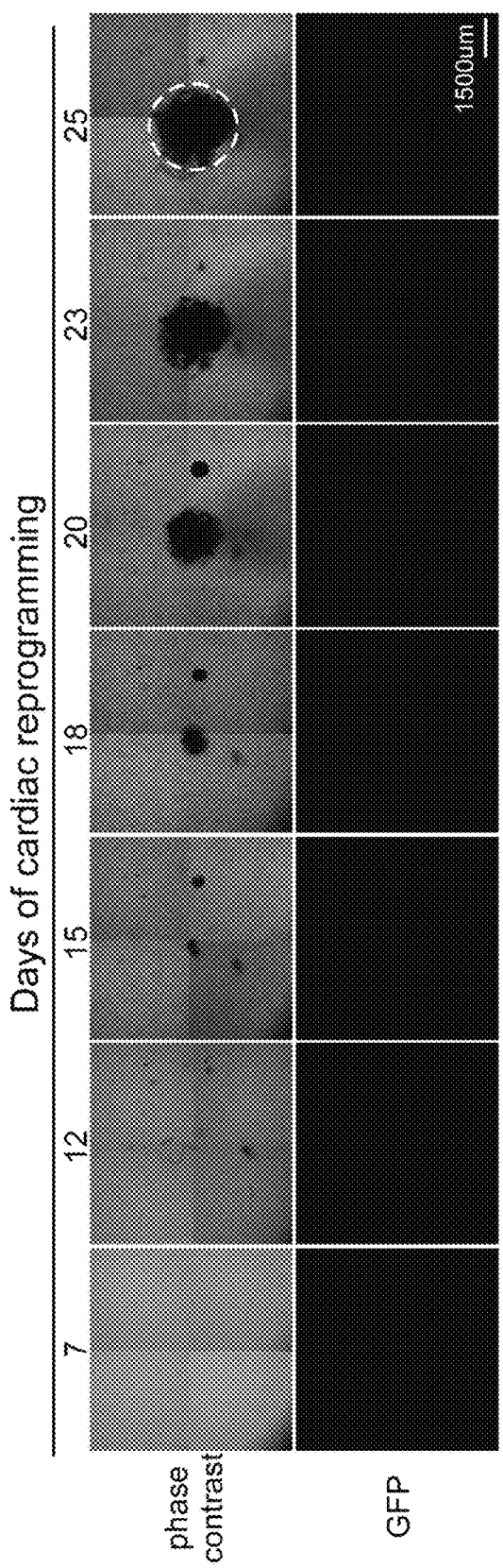
FIG. 3A-3E illustrate that pluripotent cells were not generated during the entire process of direct cardiac reprogramming by the combination of the SB431542, CHIR99021, parnate; and Forskolin (SCPF) composition combined with Oct4 expression.
Figure 3B:
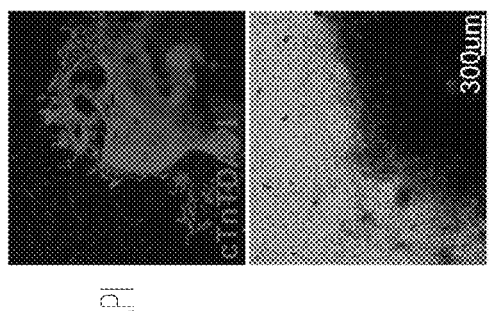

However, GFP+ cells were never detected throughout the whole reprogramming process (FIG. 3A). This finding is consistent with our previous studies on other direct cardiac, neural and endothelial cell reprogramming studies (Efe et al., Nature Cell Biology 13, 215-222 (2011); Kim et al., Proc Natl Acad Sci USA 108:7838-7843 (2011); Li et al., Arteriosclerosis, thrombosis, and vascular biology 33: 1366-1375 (2013).

Figure 3C:
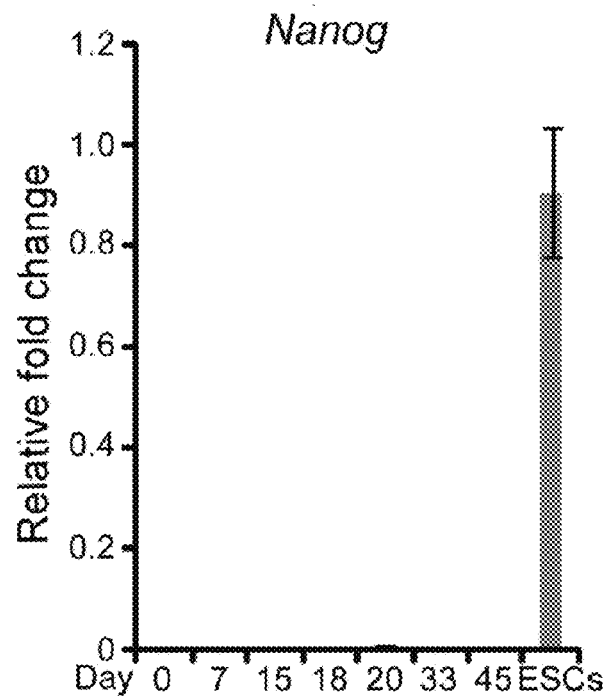
Figure 3D:
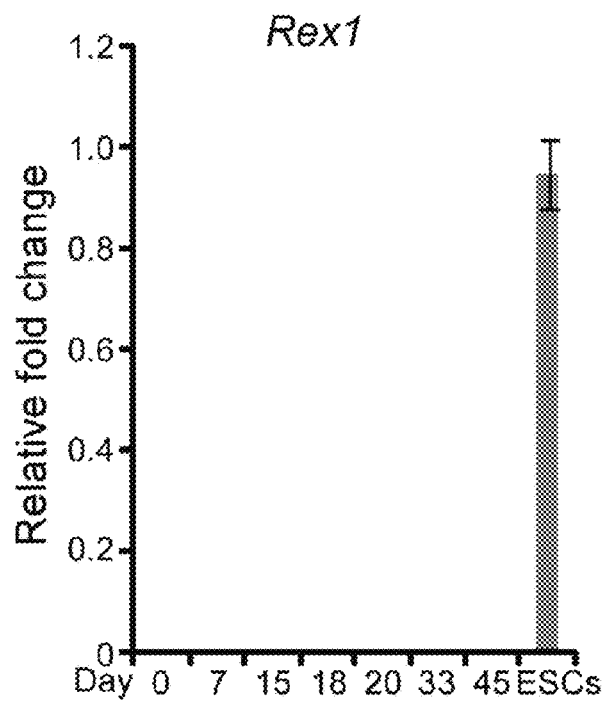
Figure 3H:
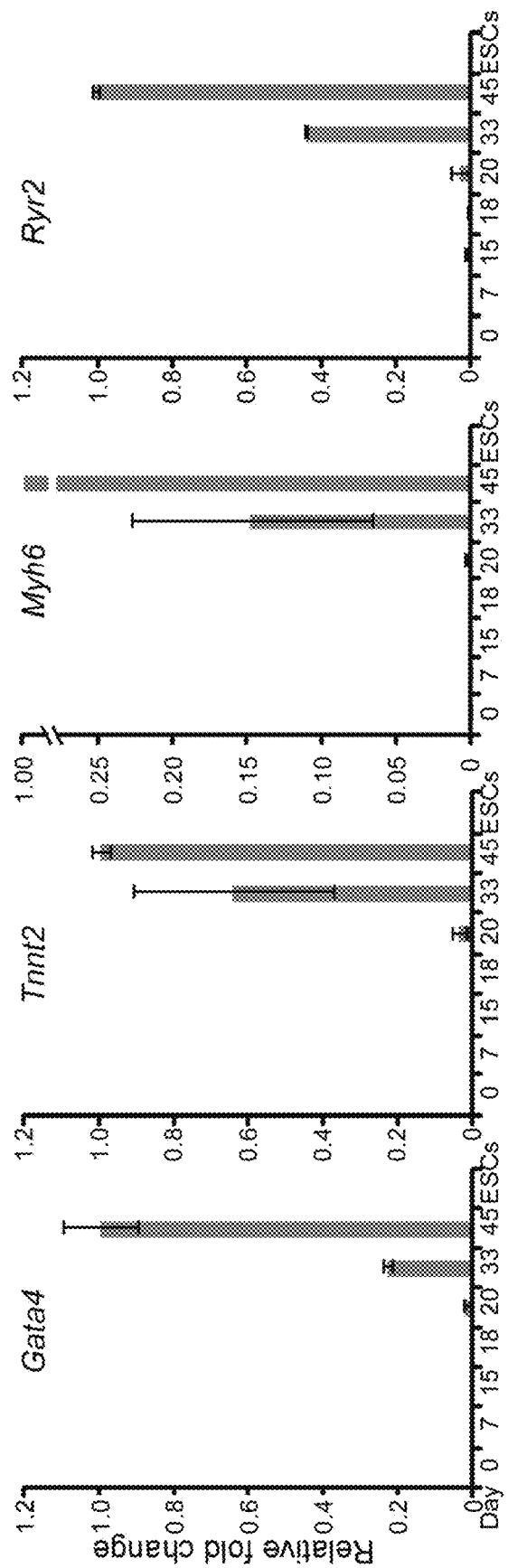

As shown in FIG. 3C-3D, the pluripotency genes Nanog and Rex1 remained nearly undetectable by qRT-PCR during the whole reprogramming process. In contrast, cardiac markers including Gata4, Tnnt2, Myh6, and Ryr2 were gradually induced from day 20 and thereafter (FIG. 3E). These data collectively confirmed that induced cardiac cells were converted from fibroblasts without traversing the pluripotent state.

Induced Cardiomyocytes Exhibited Cardiac Physiological Features

Figures 4A, 4B:
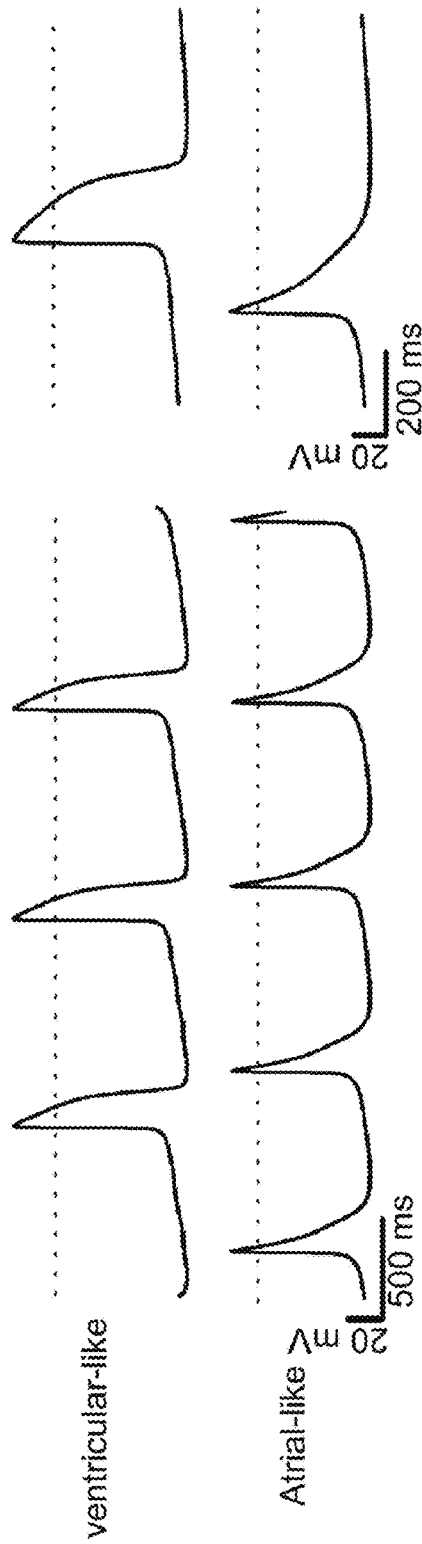
FIG. 4A-4H illustrate the electrophysiological features of the contracting cardiomyocytes generated by the compositions and methods described herein. Mouse tail tip fibroblasts (TTFs) were converted into spontaneously contracting cardiomyocytes by the SB431542, CHIR99021, parnate; and Forskolin (SCPF) composition combined with Oct4 expression. Spontaneous action potentials and calcium transients were recorded from the individual cardiomyocytes at day 35-40.

To further characterize functional properties of the cardiomyocytes reprogrammed from mouse tail tip fibroblasts, the cardiomyocytes were subjected to electrophysiological analysis. By intracellular single-cell patch-clamp analysis, action potentials (APs) were recorded from the single spontaneously beating cells after about 35 days of treatment (day 35). Based on the ratio of action potential duration at 90% to 50% repolarization (APD90 to APD50), most of our induced cardiomyocytes exhibited the ventricular-like action potential morphology with a mean diastolic potential (MOP) of −75.2 mV and a mean overshoot potential (OSP) of 23.5 mV (n=16). In contrast, very few of the cells displayed arterial or nodal-like Action Potentials (FIG. 4A).

Table 1 shows action potential parameters measured for the induced cardiomyocytes, including maximum upstroke velocity (dV/dt max), overshoot potential (OSP), minimum diastolic potential (MOP), action potential amplitude and the action potential duration (APD) at 90 and 50% repolarization, and the beating frequency.

TABLE 1

Action Potential Parameters of Reprogrammed Cardiomyocytes

|  | Ventricular-like (n = 16) | Atrial-like (n = 3) |
| --- | --- | --- |
| dv/dtMax | 91.4 ± 18.1* | 25.7 ± 5.7 |
| OSPc (mV) | 23.5 ± 1.1** | 13.9 ± 1.1 |

TABLE 1-continued

Action Potential Parameters of Reprogrammed Cardiomyocytes

| | Ventricular-like (n = 16) | Atrial-like (n = 3) |
|---|---|---|
| MDPc (mV) | −75.2 ± 1.3** | −67.8 ± 1.0 |
| Potential amp | 98.7 ± 1.3* | 81.8 ± 2.0 |
| APD50 (ms) | 102.5 ± 10.2* | 62.3 ± 6.2 |
| APD90 (ms) | 149.5 ± 11.4 | 173.3 ± 18.0 |
| Freq (Hz) | 1.3 ± 0.1 | 1.0 ± 0.1 |

*$p < 0.005$,
**$p < 0.001$.

Figure 4C:
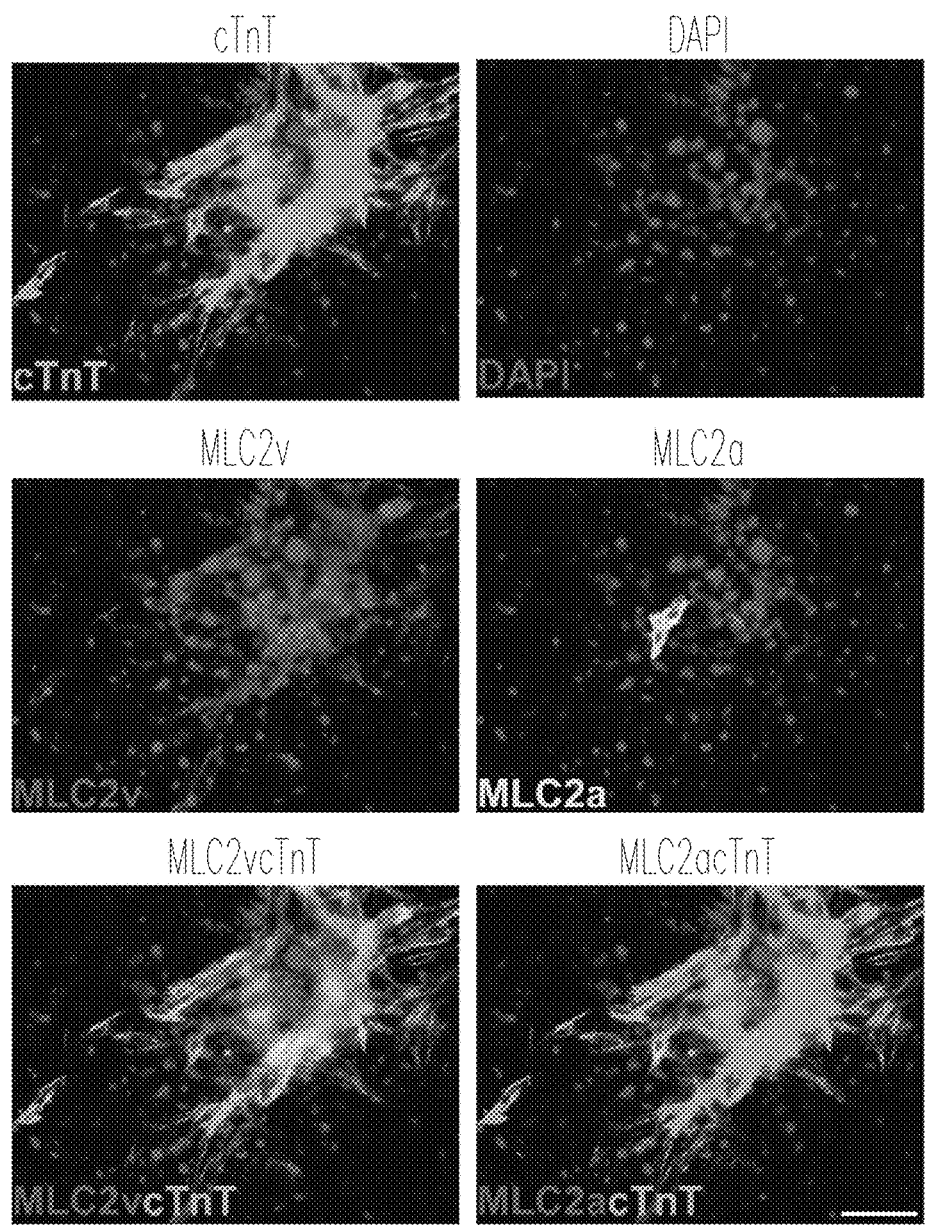
Figure 4D:
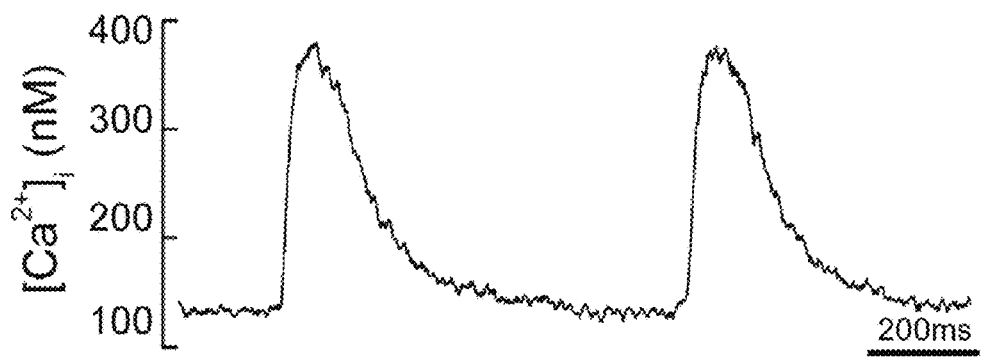

Immunostaining analysis confirmed expression of MLC2v (a ventricular specific marker) in most of the induced cardiomyocytes (FIG. 4C). These results are in contrast to the results observed with four-factor (Oct, Sox2, K1f4, and Myc) cardiac reprogramming, where only atrial-like action potential was detected in the induced cardiomyocytes (Efe et al., *Nature Cell Biology* 13, 215-222 (2011)). This illustrates that the subtype specificity of induced cardiomyocytes can be modulated by small molecule conditions. Consequently the newly developed process that includes incubating cells with SB431542, CHIR99021, parnate, and forskolin while inducing expression of an Oct polypeptide (i.e., SCPF/Oct4 condition) may represent a more desirable condition because ventricular cardiomyocytes are generated that are typically lost in heart failure. In addition, typical $Ca^{2+}$ transients were also detected (FIG. 4D), which are essential in the regulation of the contraction and relaxation of spontaneously beating cardiomyocytes, indicating that the cells have developed functional coupling among these cells.

Figure 4E:
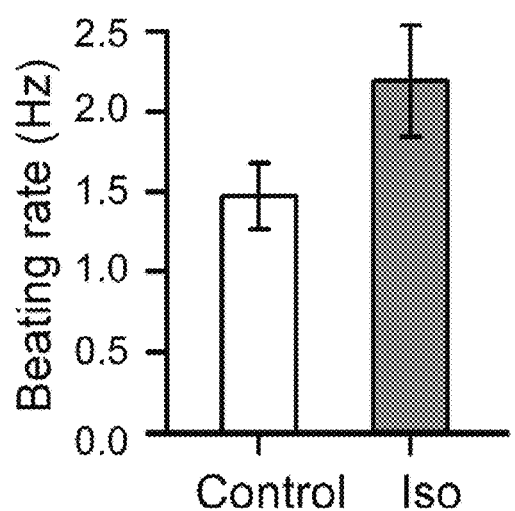
Figure 4F:
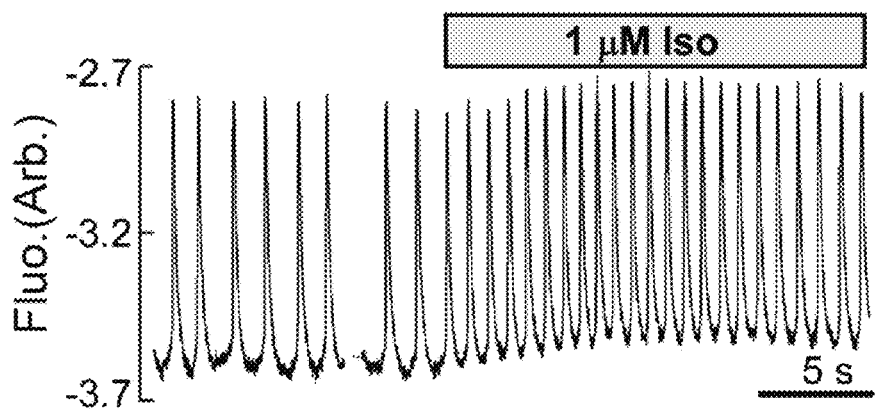
Figure 4G:
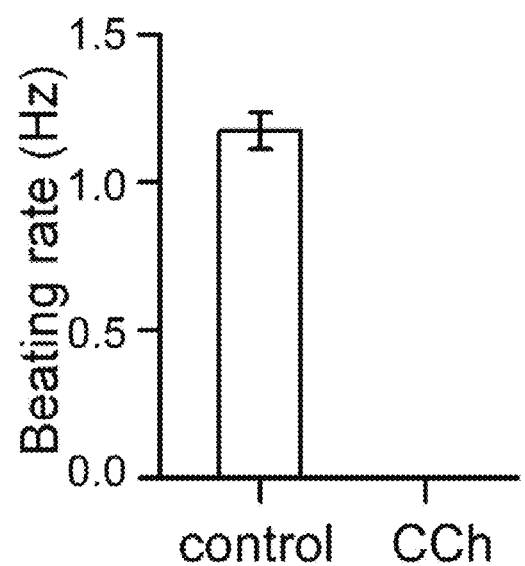
Figure 4H:
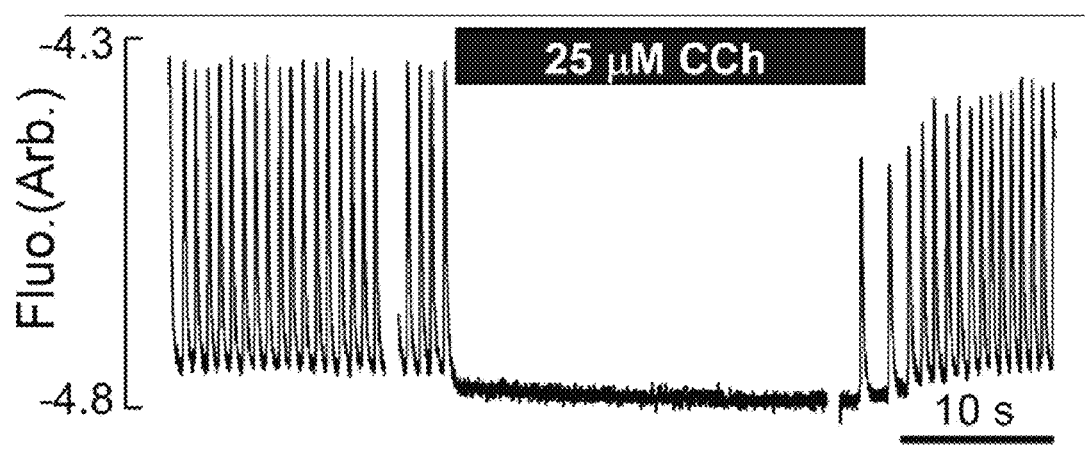

Intact central nervous system responses to hormones and transmitters are one of the most critical characteristics of normal cardiomyocytes. Hence, the response of cardiomyocytes generated from mouse tail tip fibroblasts (TTFs) to β-adrenergic and muscarinic stimulations was evaluated to assess whether critical signaling pathways are activated in cardiomyocytes. Addition of 1 μM of the β-adrenergic agonist, isoproterenol (Iso), significantly increased the frequency of cell contracting and spontaneous calcium transients (FIG. 4E, 4G), whereas carbachol (Cch), a muscarinic agonist, had the opposite effect (FIG. 4F, 4H). After washing out carbachol, cells resumed contracting and the $Ca^{2+}$ transients immediately returned to normal (FIG. 4H). The frequency of $Ca^{2+}$ transients could therefore be reversibly modulated with isoproterenol or carbachol, indicating that coupled β-adrenergic and muscarinic signaling cascades, as well as their associated intracellular signaling partners, were present and functional in the induced cardiomyocytes reprogrammed from mouse tail tip fibroblasts.

In conclusion, these data collectively demonstrate that cardiomyocytes generated by incubating cells with SB431542, CHIR99021, parnate, and forskolin while inducing expression of an Oct polypeptide possess typical cardiac electrophysiological features.

REFERENCES

Chambers, S. M., Fasano, C. A., Papapetrou, E. P., Tomishima, M., Sadelain, M., and Studer, L. (2009). Highly efficient neural conversion of human ES and iPS cells by dual inhibition of SMAD signaling. Nature biotechnology 27, 275-280.

Do, J. T., and Scholer, H. R. {2004}. Nuclei of embryonic stem cells reprogram somatic cells. Stem cells (Dayton, Ohio) 22, 941-949.

Efe, J. A., Hilcove, S., Kim, J., Zhou, H., Ouyang, K., Wang, G., Chen, J., and Ding, S. (2011). Conversion of mouse fibroblasts into cardiomyocytes using a direct reprogramming strategy. Nature cell biology 13, 215-U261.

Han, D. W., Tapia, N., Hermann, A., Hemmer, K., Hoing, S., Arauzo-Bravo, M. J., Zaehres, H., Wu, G., Frank, S., Moritz, S., et al. (2012). Direct reprogramming of fibroblasts into neural stem cells by defined factors. Cell Stem Cell10, 465-472.

Hanna, J., Cheng, A. W., Saha, K., Kim, J., Lengner, C. J., Soldner, F., Cassady, J. P., Muffat, J., Carey, B. W., and Jaenisch, R. (2010). Human embryonic stem cells with biological and epigenetic characteristics similar to those of mouse ESCs. Proc Natl Acad Sci USA 107, 9222-9227.

Hilcove, S. A. (2010). Small Molecules, Regeneration, and Cell Fate: A Thesis Presented (Scripps Research Institute, La Jolla, Calif.). Ieda, M., Fu, J. D., Delgado-Olguin, P., Vedantham, V., Hayashi, Y., Bruneau, B. G., and Srivastava, D. (2010). Direct reprogramming of fibroblasts into functional cardiomyocytes by defined factors. Cell142, 375-386.

Ieda, M., Tsuchihashi, T., lvey, K. N., Ross, R. S., Hong, T. T., Shaw, R. M., and Srivastava, D. (2009). Cardiac fibroblasts regulate myocardial proliferation through beta1 integrin signaling. Developmental cell16, 233-244.

Kathiresan, S., and Srivastava, D. (2012). Genetics of human cardiovascular disease. Cell148, 1242-1257.

Kattman, S. J., Witty, A. D., Gagliardi, M., Dubois, N. C., Niapour, M., Hotta, A., Ellis, J., and Keller, G. (2011). Stage-specific optimization of activin/nodal and BMP signaling promotes cardiac differentiation of mouse and human pluripotent stem cell lines. Cell Stem Cell 8, 228-240.

Kim, J., Efe, J. A., Zhu, S., Talantova, M., Yuan, X., Wang, S., Lipton, S. A., Zhang, K., and Ding, S. (2011). Direct reprogramming of mouse fibroblasts to neural progenitors. Proc Natl Acad Sci USA 108, 7838-7843.

Kuzmenkin, A., Liang, H., Xu, G., Pfannkuche, K., Eichhorn, H., Fatima, A., Luo, H., Saric, T., Wernig, M., Jaenisch, R., et al. (2009). Functional characterization of cardiomyocytes derived from murine induced pluripotent stem cells in vitro. FASEB J 23, 4168-4180.

Li, J., Huang, N. F., Zou, J., Laurent, T. J., Lee, J. C., Okogbaa, J., Cooke, J. P., and Ding, S. (2013a). Conversion of Human Fibroblasts to Functional Endothelial Cells by Defined Factors. Arteriosclerosis, thrombosis, and vascular biology 33, 1366-1375.

Li, J., Huang, N. F., Zou, J., Laurent, T. J., Lee, J. C., Okogbaa, J., Cooke, J. P., and Ding, S. (2013b). Conversion of human fibroblasts to functional endothelial cells by defined factors. Arteriosclerosis, thrombosis, and vascular biology 33, 1366-1375.

Li, R., Liang, J., Ni, S., Zhou, T., Qing, X., Li, H., He, W., Chen, J., Li, F., Zhuang, Q., et al. (2010). A mesenchymal-to-epithelial transition initiates and is required for the nuclear reprogramming of mouse fibroblasts. Cell Stem Cell 7, 51-63.

Li, W., Zhou, H., Abujarour, R., Zhu, S., Young Joo, J., Lin, T., Hao, E., Scholer, H. R., Hayek, A., and Ding, S. {2009). Generation of human-induced pluripotent stem cells in the absence of exogenous Sox2. Stem cells (Dayton, Ohio) 27, 2992-3000.

Li, Y., Zhang, Q., Yin, X., Yang, W., Du, Y., Hou, P., Ge, J., Liu, C., Zhang, W., Zhang, X., et al. (2011). Generation of iPSCs from mouse fibroblasts with a single gene, Oct4, and small molecules. Cell research 21, 196-204.

Lian, X., Hsiao, C., Wilson, G., Zhu, K., Hazeltine, L. B., Azarin, S. M., Raval, K. K., Zhang, J., Kamp, T. J., and Palecek, S. P. (2012). Robust cardiomyocyte differentiatio11 from human pluripotent stem cells via temporal modulation of canonical Wnt signaling. Proc Natl Acad Sci USA 109, E1848-1857.

Lin, T., Ambasudhan, R., Yuan, X., Li, W., Hilcove, S., Abujarour, R., Lin, X., Hahm, H. S., Hao, E., Hayek, A., et al. (2009). A chemical platform for improved induction of human iPSCs. Nature methods 6, 805-808.

Naito, A. T., Shiojima, I., Akazawa, H., Hidaka, K., Morisaki, T., Kikuchi, A., and Komuro, I. (2006). Developmental stage-specific biphasic roles of Wnt/beta-catenin signaling in cardiomyogenesis and hematopoiesis. Proc Natl Acad Sci USA 103, 19812-19817.

Nie, B., Wang, H., Laurent, T., and Ding, S. (2012). Cellular reprogramming: a small molecule perspective. Current opinion in cell biology 24, 784-792.

Sancho-Martinez, 1., Baek, S. H., and Belmonte, J. C. I. (2012). Lineage conversion methodologies meet the reprogramming toolbox. Nature cell biology 14, 892-899.

Shi, Y., Desponts, C., Do, J. T., Hahm, H. S., Scholer, H. R., and Ding, S. (2008). Induction of pluripotent stem cells from mouse embryonic fibroblasts by Oct4 and K1f4 with small-molecule compounds. Cell Stem Cell 3, 568-574.

Song, K., Nam, Y. J., Luo, X., Qi, X., Tan, W., Huang, G. N., Acharya, A., Smith, C. L., Tallquist, M. D., Neilson, E. G., et al. (2012). Heart repair by reprogramming non-myocytes with cardiac transcription factors. Nature 485, 599-604.

Thier, M., Worsdorfer, P., Lakes, Y. B., Gorris, R., Herms, S., Opitz, T., Seiferling, D., Quandel, T., Hoffmann, P., Nothen, M. M., et al. (2012). Direct conversion of fibroblasts into stably expandable neural stem cells. Cell Stem Cell10, 473-479.

Willems, E., Cabral-Teixeira, J., Schade, D., Cai, W., Reeves, P., Bushway, P. J., Lanier, M., Walsh, C., Kirchhausen, T., Izpisua Belmonte, J. C., et al. (2012). Small molecule-mediated TGF-beta type II receptor degradation promotes cardiomyogenesis in embryonic stem cells. Cell Stem Cell11, 242-252.

Yang, L., Soonpaa, M. H., Adler, E. D., Roepke, T. K., Kattman, S. J., Kennedy, M., Henckaerts, E., Bonham, K., Abbott, G. W., Linden, R. M., et al. (2008). Human cardiovascular progenitor cells develop from a KDR+ embryonic-stem-cell-derived population. Nature 453, 524-528.

Yu, J., Vodyanik, M. A., Smuga-Otto, K., Antosiewicz-Bourget, J., Frane, J. L., Tian, S., Nie, J., Jonsdottir, G. A., Ruotti, V., Stewart, R., et al. (2007). Induced pluripotent stem cell lines derived from human somatic cells. Science 318, 1917-1920.

Yuan, X., Wan, H., Zhao, X., Zhu, S., Zhou, Q., and Ding, S. (2011). Brief report: combined chemical treatment enables Oct4-induced reprogramming from mouse embryonic fibroblasts. Stem cells (Dayton, Ohio) 29, 549-553.

Zhu, S., Li, W., Zhou, H., Wei, W., Ambasudhan, R., Lin, T., Kim, J., Zhang, K., and Ding, S. {2010). Reprogramming of human primary somatic cells by OCT4 and chemical compounds. Cell Stem Cell 7, 651-655.

Zhu, S., Wei, W., and Ding, S. (2011). Chemical strategies for stem cell biology and regenerative medicine. Annual review of biomedical engineering 13, 73-90.

The following statements are intended to describe and summarize various aspects and/or embodiments of the invention according to the foregoing description in the specification Statements 1. A composition comprising one or more of the following agents: a WNT agonist, a GSK3 inhibitor, a TGF-beta inhibitor, an epigenetic modifier, an adenylyl cyclase agonist, an agent that induces Oct polypeptide expression, and any combination thereof.
2. The composition of statement 1, containing at least two of the agents, or at least three of the agents, or at least four of the agents, or at least five of the agents, or at least six of the agents.
3. The composition of statements 1 or 2, wherein the WNT agonist is an agent that activates TCF/LEF-mediated transcription in a cell.
4. The composition of any of statements 1-3, wherein the WNT agonist binds and activates a Frizzled receptor family member.
5. The composition of any of statements 1-4, wherein the WNT agonist is one or more of a WNT family protein, an inhibitor of intracellular beta-catenin degradation, an activator of TCF/LEF, an inhibitor of GSK-3, or a combination thereof.
6. The composition of any of statements 1-5, wherein the WNT agonist is one or more of WNT-3a, a GSK-inhibitor, WNT5, WNT-6a, Norrin, or another WNT family protein.
7. The composition of any of statements 1-6, wherein the GSK3 inhibitor is one or more of CHIR99021 (6-(2-(4-(2,4-dichlorophenyl)-5-(4-methyl-1H-imidazol-2-yl)pyrimidin-2-ylamino)ethylamino)nicotinonitrile); 1-azakenpaullone (9-Bromo-7,12-dihydro-pyrido[3',2':2,3]azepino[4,5-b]indol-6(5H)-one), BIO ((2'Z,3'E)-6-Bromoindirubin-3'-oxime); AR-A014418 (N-(4-Methoxybenzyl)-N'-(5-nitro-1,3-thiazol-2-yl)urea); Indirubin-3'-monoxime; 5-Iodo-indirubin-3'-monoxime; kenpaullone (9-Bromo-7,12-dihydroindolo-[3,2-d] [1]benzazepin-6(5H)-one); SB-415286 (3-[(3-Chloro-4-hydroxyphenyl)amino]-4-(2-nitro-phenyl)-1H-pyrrole-2,5-dione); SB-216763 (3-(2,4-Dichlorophenyl)-4-(1-methyl-1H-indol-3-yl)-1H-pyrrole-2,5-dione); Maybridge SEW00923SC (2-anilino-5-phenyl-1,3,4-oxadiazole); (Z)-5-(2,3-Methylenedioxyphenyl)-imidazolidine-2,4-dione; TWS119 (3-(6-(3-aminophenyl)-7H-pyrrolo[2,3-d]pyrimidin-4-yloxy)phenol); CHIR98014 (N2-(2-(4-(2,4-dichlorophenyl)-5-(1H-imidazol-1-yl)pyrimidin-2-ylamino)ethyl)-5-nitropyridine-2,6-diamine); SB415286 (3-(3-chloro-4-hydroxyphenylamino)-4-(2-nitrophenyl)-1H-pyrrole-2,5-dione); Tideglusib (2-(1-naphthalenyl)-4-(phenylmethyl)); LY2090314 (3-imidazo[1,2-a]pyridin-3-yl-4-[1,2,3,4-tetrahydro-2-(1-piperidinylcarbonyl)-pyrrolo[3,2,1-jk][1,4]benzodiazepin-7-yl]); lithium salt; or any combination thereof.
8. The composition of any of statements 1-7, wherein the GSK3 inhibitor is one or more of CHIR99021, SB216763, TWS119, CHIR98014, Tideglusib (NP031112, NP-12), SB415286, LY2090314, or any combination thereof.
9. The composition of any of statements 1-8, wherein the GSK3 inhibitor is CHIR99021.
10. The composition of any of statements 1-9, wherein the TGFβ inhibitor is one or more of 4-[4-(1,3-benzodioxol-5-yl)-5-(2-pyridinyl)-1H-imidazol-2-yl]benzamide (SB 431542); 3-(6-Methyl-2-pyridinyl)-N-phenyl-4-(4-quinolinyl)-1H-pyrazole-1-carbothioamide (A83-01); 2-(3-(6-Methylpyridine-2-yl)-1H-pyrazol-4-yl)-1,5-naphthyridine (SJN 2511); 4-[4-(2,3-Dihydro-1,4-benzodioxin-6-yl)-5-(2-pyridinyl)-1H-imidazol-2-yl]benzamide (D 4476); 4-[3-(2-Pyridinyl)-1H-pyrazol-4-yl]-quinoline (LY 364947); 2-(4-(benzo[d][1,3]dioxol-5-yl)-2-tert-butyl-1H-imidazol-5-yl)-6-methylpyridine (SB505124); 6-[2-(1,1-Dimethylethyl)-5-(6-methyl-2-pyridinyl)-1H-imidazol-4-yl]quinoxaline (SB 525334); 2-(5-Chloro-2-fluorophenyl)-4-[(4-pyridyl)amino]pteridine (SD 208); 4-(6-(4-(piperazin-1-yl)phenyl)pyrazolo[1,5-a]pyrimidin-3-yl)quinoline, or any combination thereof.

11. The composition of any of statements 1-10, wherein the TGFβ inhibitor is SB431542.

12. The composition of any of statements 1-11, wherein the epigenetic modifier is a methylation modifying agent, an acetylation modifying agent, a monoamine oxidase (MAO) inhibitor, or a combination thereof.

13. The composition of any of statements 1-12, wherein the epigenetic modifier inhibits lysine-specific demethylase 1.

14. The composition of any of statements 1-13, wherein the epigenetic modifier is RG108, valproic acid, BIX0129, parnate (tranylcypromine sulfate or equivalent salt), or a combination thereof.

15. The composition of any of statements 1-14, wherein the epigenetic modifier is parnate.

16. The composition of any of statements 1-15, wherein the adenylyl cyclase agonist is Forskolin, CGP 12177 (4-[3-[(1,1-Dimethylethyl)amino]2-hydroxypropoxy]-1,3-dihydro-2H-benzimidazol-2-one hydrochloride), or a combination thereof.

17. The composition of any of statements 1-16, wherein the adenylyl cyclase agonist is Forskolin.

18. The composition of any of statements 1-17, comprising one or more of the following agents: SB431542 (an ALK4/5/7 inhibitor), CHIR99021 (a GSK3 inhibitor), parnate (an LSD1/KDM1 inhibitor, also called tranylcypromine), forskolin (an adenylyl cyclase activator), or a combination thereof.

19. The composition of any of statements 1-17, consisting essentially of one or more of the following agents: SB431542 (an ALK4/5/7 inhibitor), CHIR99021 (a GSK3 inhibitor), parnate (an LSD1/KDM1 inhibitor, also called tranylcypromine), forskolin (an adenylyl cyclase activator), or a combination thereof.

20. The composition of any of statements 1-19, wherein the composition is a cell reprogramming composition.

21. The composition of any of statements 1-20, further comprising a physiologically acceptable excipient or carrier.

22. The composition of any of statements 1-21, further comprising a cell culture media.

23. The composition of any of statements 1-22, wherein the agent(s) or compound(s) is present in an amount sufficient to reprogram a cell into a cardiac progenitor, a cardiomyocyte, or a cardiac cell type.

24. The composition of any of statements 1-23, wherein the agent(s) or compound(s) is present in an amount sufficient to induce a cell to express Myh6, Tnnt2, Ryr2, Gata4, or a combination thereof.

25. The composition of any of statements 1-24, wherein the agent(s) or compound(s) is present in an amount sufficient to induce a cell to express Myh6, Tnnt2, Ryr2, Gata4, Nkx2-5, α-Actinin, Mlc2v, Mlc2a, MY20, cMHC, MEF2c, ISL1, cTNT, cTNI, or any combination thereof.

26. The composition of any of statements 1-25, wherein the agent(s) or compound(s) is present in an amount sufficient to induce a cell to contract or beat rhythmically.

27. The composition of any of statements 1-26, wherein the agent(s) or compound(s) is present in an amount sufficient to induce action potentials and calcium transients characteristic of cardiac ventricular cells.

28. The composition of any of statements 1-27, furthering comprising one or more cells.

29. The composition of any of statements 1-28, further comprising one or more cells that comprise Oct RNA, Oct polypeptide, or a combination thereof.

30. The composition of any of statements 1-29, further comprising one or more cells that comprise an introduced RNA or an expression cassette encoding an Oct polypeptide (but, e.g., no exogenously introduced K1f4, Myc, and/or Sox2 nucleic acids).

31. The composition of any of statements 1-29, further comprising one or more cells that comprise an introduced RNA comprising an open reading frame (ORF) for the Oct polypeptide flanked by a 5' untranslated region (UTR) containing a translational initiation signal.

32. The composition of any of statements 28-31, wherein the one or more cells are non-cardiac cells.

33. The composition of any of statements 28-32, wherein the one or more cells are differentiated cells.

34. The composition of any of statements 28-33, wherein the one or more cells are somatic cells.

35. The composition of any of statements 28-34, wherein the one or more cells are adult cells.

36. The composition of any of statements 28-35, wherein the one or more cells are multipotent, unipotent, or progenitor cells.

37. The composition of any of statements 28-36, wherein the one or more cells are newborn cord blood cells, or newborn stem cells.

38. The composition of any of statements 28-37, wherein the one or more cells are allogenic or autologous cells.

39. The composition of any of statements 1-38, further comprising a heterogeneous or homogeneous mixture of cells.

40. A cell culture media comprising the composition of any of statements 1-39.

41. A method of generating one or more cardiac progenitor cells, cardiomyocytes, or cardiac cells comprising contacting one or more selected cells with the composition of any of statements 1-39, or the cell media of statement 40, to thereby generate one or more cardiac progenitor cells, cardiomyocytes, cardiac cells, or a combination thereof.

42. The method of statement 41, wherein the one or more selected cells comprise Oct RNA molecules, Oct polypeptides, or a combination thereof.

43. The method of statement 41 or 42, wherein the one or more selected cells comprise an introduced RNA.

44. The method of any of statements 41-43, wherein the one or more selected cells comprise an introduced RNA comprising an open reading frame (ORF) for the Oct polypeptide flanked by a 5' untranslated region (UTR) containing a translational initiation signal.

45. The method of any of statements 41-44, wherein the one or more selected cells can express an Oct RNA from a heterologous promoter.
46. The method of any of statements 41-45, wherein the one or more selected cells can express an Oct RNA from a heterologous expression cassette or expression vector.
47. The method of any of statements 41-46, wherein the one or more selected cells transiently expresses an Oct polypeptide for at least two days, or at least three days, or at least four days, or at least five days, or at least six days, or at least seven days, or at least eight days, while contacted with the composition.
48. The method of any of statements 41-47, wherein the one or more selected cells can express an Oct RNA but do not have a heterologous Oct nucleic acid integrated into the cell's genome.
49. The method of any of statements 41-48, wherein the one or more selected cells can express an Oct polypeptide from a replication-defective expression vector.
50. The method of any of statements 41-49, wherein the one or more selected cells can express a human Oct polypeptide.
51. The method of any of statements 41-50, wherein the one or more selected cells can express an Oct polypeptide with a sequence that has at least 95% sequence identity to SEQ ID NO:1 or 3.
52. The method of any of statements 41-51, wherein the one or more selected cells comprises a cDNA with a sequence that has at least 95% sequence identity to SEQ ID NO:2 or 4.
53. The method of any of statements 41-52, wherein the one or more selected cells are a population of cells, a heterogeneous mixture of cells, or a homogeneous mixture of cells.
54. The method of any of statements 41-53, wherein the one or more selected cells are differentiated cells, non-cardiac cells, somatic cells, adult cells, multipotent cells, unipotent cells, progenitor cells, newborn cord blood cells, newborn stem cells, or a combination thereof.
55. The method of any of statements 41-54, wherein the one or more selected cells are allogenic cells or autologous cells.
56. The method of any of statements 41-55, wherein the one or more selected cells are contacted with the composition or the media for a time and/or with an amount of each agent sufficient to induce the selected cell to express Myh6, Tnnt2, Ryr2, Gata4, or a combination thereof.
57. The method of any of statements 41-56, wherein the one or more selected cells are contacted with the composition or the media for a time and/or with an amount of each agent sufficient to induce the selected cell to express Myh6, Tnnt2, Ryr2, Gata4, Nkx2-5, α-Actinin, Mlc2v, Mlc2a, MY20, cMHC, MEF2c, ISL1, cTNT, cTNI, or any combination thereof.
58. The method of any of statements 41-57, furthering comprising administering the cardiac progenitor cell(s), the cardiomyocyte(s), the cardiac cell(s), or a combination thereof to a subject.
59. The method of any of statements 41-58, furthering comprising administering at least about 100 of the cardiac progenitor cells, the cardiomyocytes, the cardiac cells, or a combination thereof to a subject.
60. The method of any of statements 41-59, comprising administering at least about 1000, or at least about 10,000, or at least about 100,000, or at least about 1,000,000, or at least about 10,000,000, or at least about 100,000,000 of the cardiac progenitor cells, the cardiomyocytes, the cardiac cells, or a combination thereof to a subject.
61. The method of any of statements 41-60, wherein the cardiac progenitor cell(s), cardiomyocyte(s), and/or cardiac cell(s) are allogenic or autologous cell(s).
62. The method of any of statements 41-61, wherein the cardiac progenitor cell(s), cardiomyocyte(s), and/or cardiac cell(s) is/are cardiac progenitor cells.
63. The method of any of statements 41-61, wherein the cardiac progenitor cell(s), cardiomyocyte(s), and/or cardiac cell(s) is/are mature cardiomyocyte(s).
64. The method of any of statements 41-63, wherein the subject suffers or is suspected of suffering from a heart condition or disease.
65. The method of any of statements 41-64, wherein the subject's heart is abnormally enlarged, thickened and/or stiffened.
66. The method of any of statements 41-65, wherein the subject suffers or is suspected of suffering from a heart condition or disease resulting from inflammation, a metabolic condition, toxic exposure, an infiltrative process, a fibroplastic process, a hematological condition, a genetic condition, or a combination thereof.
67. The method of any of statements 41-66, wherein the subject suffers or is suspected of suffering from congestive heart failure, myocardial infarction, cardiac ischemia, myocarditis, arrhythmia, Duchenne muscular dystrophy, Emery Dreiffuss dilated cardiomyopathy, or any combination thereof.
68. A method comprising administrating the composition of any of statements 1-39, to a subject.
69. The method of statement 68, wherein the composition contains one or more cardiac cells, cardiac progenitor cells and/or mature cardiomyocytes.
70. The method of statement 68 or 69, wherein the composition contains one or more allogenic or autologous cells.
71. The method of any of statements 68-70, wherein the composition contains one or more, or at least about 1000, cells that express Myh6, Tnnt2, Ryr2, Gata4, or a combination thereof.
72. The method of any of statements 68-71, wherein the composition contains one or more, or at least about 1000, cells that express Myh6, Tnnt2, Ryr2, Gata4, Nkx2-5, α-Actinin, Mlc2v, Mlc2a, MY20, cMHC, MEF2c, ISL1, cTNT, cTNI, or any combination thereof.
73. The method of any of statements 68-72, wherein the composition contains at least about 1000, or at least about 10,000, or at least about 100,000, or at least about 1,000,000, or at least about 10,000,000, or at least about 100,000,000 of the cardiac cells, cardiac progenitor cells and/or mature cardiomyocytes.
74. The method of any of statements 68-73, wherein the subject is in need of administration of the composition.
75. The method of any of statements 68-74, wherein the subject is in need of one or more cardiac cells, cardiac progenitor cells and/or mature cardiomyocytes.
76. The method of any of statements 68-75, wherein the composition is administered for a time and/or with an amount of each agent sufficient to reduce the symptoms of a heart condition or disease.

77. The method of any of statements 68-76, wherein the subject's heart is abnormally enlarged, thickened and/or stiffened.
78. The method of any of statements 68-77, wherein the subject suffers or is suspected of suffering from a heart condition or disease resulting from inflammation, a metabolic condition, toxic exposure, an infiltrative process, a fibroplastic process, a hematological condition, a genetic condition, or a combination thereof.
79. The method of any of statements 68-78, wherein the subject suffers or is suspected of suffering from congestive heart failure, myocardial infarction, cardiac ischemia, myocarditis, arrhythmia, Duchenne muscular dystrophy, Emery Dreiffuss dilated cardiomyopathy, or any combination thereof.
80. A kit comprising the composition of any of statements 1-39, and instructions for using the composition or the media.
81. The kit of statement 80, further comprising components for in vitro cell culture of a selected cell.
82. The kit of statement 80 or 81, further comprising a cell culture medium, one or more sterile cell collection devices, a supplementary factor, or a combination thereof.
83. The kit of statement 82, wherein the supplementary factor comprises at least one bone morphogenic protein, brain derived neurotrophic factor, ciliary neurotrophic factor, cytokine-induced neutrophil chemotactic factor 1, cytokine-induced neutrophil chemotactic factor 2α, cytokine-induced neutrophil chemotactic factor 2β, β endothelial cell growth factor, endothelin 1, epidermal growth factor, epithelial-derived neutrophil attractant, fibroblast growth factor, growth related protein, heparin binding epidermal growth factor, hepatocyte growth factor, insulin-like growth factor, keratinocyte growth factor, leukemia inhibitory factor, neurotrophin, placenta growth factor, platelet-derived endothelial cell growth factor, platelet derived growth factor, pre-B cell growth stimulating factor, stem cell factor, transforming growth factor, latent transforming growth factor, transforming growth factor β binding protein, vascular endothelial growth factor or any combination thereof.
84. The kit of any of statements 80-83, further comprising one or more cells that comprise Oct RNA, Oct polypeptide, or a combination thereof.
85. The kit of any of statements 80-84, further comprising one or more cells that comprise an introduced RNA.
86. The kit of any of statements 80-85, further comprising one or more cells that comprise an introduced RNA comprising an open reading frame (ORF) for the Oct polypeptide flanked by a 5' untranslated region (UTR) containing a translational initiation signal.
87. The kit of any of statements 80-86, further comprising a container of microRNA-302, an expression cassette encoding microRNA-302, an expression vector encoding microRNA-302, or a combination thereof.
88. The kit of any of statements 80-87, further comprising one or more cells wherein the one or more cells are non-cardiac cells.
89. The kit of any of statements 80-88, further comprising one or more cells wherein the one or more cells are differentiated cells.
90. The kit of any of statements 80-89, further comprising one or more cells wherein the one or more cells are somatic cells.
91. The kit of any of statements 80-90, further comprising one or more cells wherein the one or more cells are adult cells.
92. The kit of any of statements 80-91, further comprising one or more cells wherein the one or more cells are multipotent, unipotent, or progenitor cells.
93. The kit of any of statements 80-92, wherein the one or more cells are newborn cord blood cells, or newborn stem cells.
94. The kit of any of statements 80-93, wherein the one or more cells are allogenic or autologous cells.
95. The kit of any of statements 80-94, further comprising a population of cardiac cells, cardiomyocytes, cardiac cells, or a combination thereof generated by contacting one or more selected cells with the composition.
96. The kit of any of statements 80-95, further comprising a diluent, a pharmaceutically acceptable carrier, a syringe, a catheter, or a device for delivery of cells or of the composition.

All patents and publications referenced or mentioned herein are indicative of the levels of skill of those skilled in the art to which the invention pertains, and each such referenced patent or publication is hereby specifically incorporated by reference to the same extent as if it had been incorporated by reference in its entirety individually or set forth herein in its entirety. Applicants reserve the right to physically incorporate into this specification any and all materials and information from any such cited patents or publications.

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. The methods and processes illustratively described herein suitably may be practiced in differing orders of steps, and the methods and processes are not necessarily restricted to the orders of steps indicated herein or in the claims.

As used herein and in the appended claims, the singular forms "a," "an," and "the" include plural reference unless the context clearly dictates otherwise. Thus, for example, a reference to "a compound," "a cell," "a nucleic acid" or "a polypeptide" includes a plurality of such compounds, cells, nucleic acids or polypeptides (for example, a solution of cells, nucleic acids or polypeptides, a suspension of cells, or a series of compound, cell, nucleic acid or polypeptide preparations), and so forth. Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims and statements of the invention.

What is claimed is:

1. A method of converting a fibroblast into a cardiomyocyte or cardiomyocyte-like cell comprising:
   contacting a fibroblast with an agent that induces Oct4 polypeptide expression; and
   contacting a fibroblasts with at least four of the following agents: a WNT agonist, a GSK3 inhibitor, a TGF-beta inhibitor, an epigenetic modifier, or an adenylyl cyclase agonist.

2. The method of claim 1, wherein the fibroblast is contacted with an agent that induces Oct4 polypeptide expression and with a TGF-beta inhibitor, a GSK3 inhibitor, an epigenetic modifier, and an adenylyl cyclase agonist.

3. The method of claim 1, wherein the fibroblast is contacted with an agent that induces Oct4 polypeptide expression and with an ALK4/5/7 inhibitor, a GSK3 inhibitor, a LSD1/KDM1 inhibitor and an adenylyl cyclase agonist.

4. A method of converting a mammalian fibroblast into a cardiomyocyte or cardiomyocyte-like cell, comprising:
   contacting a mammalian fibroblast with an agent that induces Oct4 polypeptide expression; and
   contacting the mammalian fibroblast with at least four of the following agents: a WNT agonist, a GSK3 inhibitor, a TGF-beta inhibitor, an epigenetic modifier, or an adenylyl cyclase agonist.

5. The method of claim 4, wherein the mammalian fibroblast is contacted with an agent that induces Oct4 polypeptide expression and with a TGF-beta inhibitor, a GSK3 inhibitor, an epigenetic modifier, and an adenylyl cyclase agonist.

6. The method of claim 4, wherein the mammalian fibroblast is contacted with an agent that induces Oct4 polypeptide expression and with an ALK4/5/7 inhibitor, a GSK3 inhibitor, a LSD1/KDM1 inhibitor and an adenylyl cyclase agonist.

7. The method of claim 4, wherein the mammalian fibroblast is contacted with a vector for expression of Oct4 polypeptides.

8. The method of claim 4, wherein the mammalian fibroblast is contacted with Oct4 RNA molecules.

9. The method of claim 4, wherein the mammalian fibroblast comprises an introduced RNA comprising an open reading frame (ORF) for the Oct4 polypeptide flanked by a 5' untranslated region (UTR) containing a translational initiation signal.

10. The method of claim 4, wherein the mammalian fibroblast expresses an Oct4 polypeptide from a heterologous promoter.

11. The method of claim 10, wherein a heterologous Oct4 nucleic acid is not integrated into the mammalian fibroblast's genome.

12. The method of claim 4, wherein the mammalian fibroblast transiently expresses an Oct4 polypeptide.

13. The method of claim 4, wherein the mammalian fibroblast can express an Oct4 polypeptide from a replication-defective expression vector.

14. The method of claim 4, further comprising administering one or more of the cells produced according to the method of claim 4 to a subject.

15. The method of claim 14, furthering comprising administering at least about 100 of the cells produced according to the method of claim 4 to a subject.

16. The method of claim 14, wherein the subject suffers or is suspected of suffering from a heart condition or disease.

17. The method of claim 14, wherein the subject's heart is abnormally enlarged, thickened and/or stiffened.

18. The method of claim 14, wherein the subject suffers from, or is suspected of suffering from, congestive heart failure.

19. The method of claim 14, wherein the subject suffers from, or is suspected of suffering from, myocardial infarction.

20. The method of claim 1, wherein the fibroblast is contacted with a vector for expression of Oct4 polypeptides.

21. The method of claim 1, wherein the fibroblast is contacted with Oct4 RNA molecules.

22. The method of claim 1, wherein the fibroblast comprises an introduced RNA comprising an open reading frame (ORF) for the Oct4 polypeptide flanked by a 5' untranslated region (UTR) containing a translational initiation signal.

23. The method of claim 20, wherein the fibroblast expresses an Oct4 polypeptide from a heterologous promoter.

24. The method of claim 20, wherein the fibroblast transiently expresses an Oct4 polypeptide.

25. The method of claim 20, wherein a heterologous Oct4 nucleic acid is not integrated into the fibroblast's genome.

26. The method of claim 20, wherein the fibroblast can express an Oct4 polypeptide from a replication-defective expression vector.

27. The method of claim 1, furthering comprising administering one or more of the cells produced according to the method of claim 1 to a subject.

28. The method of claim 27, furthering comprising administering at least about 100 of the cells produced according to the method of claim 1 to a subject.

29. The method of claim 28, wherein the subject suffers or is suspected of suffering from a heart condition or disease.

30. The method of claim 28, wherein the subject's heart is abnormally enlarged, thickened and/or stiffened.

31. The method of claim 28, wherein the subject suffers from, or is suspected of suffering from, congestive heart failure.

32. The method of claim 28, wherein the subject suffers from, or is suspected of suffering from, myocardial infarction.

* * * * *